US012662687B2

(12) United States Patent
Lynch et al.

(10) Patent No.: US 12,662,687 B2
(45) Date of Patent: Jun. 23, 2026

(54) METHODS AND COMPOSITIONS FOR THE PRODUCTION OF XYLITOL FROM XYLOSE UTILIZING DYNAMIC METABOLIC CONTROL

(71) Applicant: Duke University, Durham, NC (US)

(72) Inventors: Michael David Lynch, Durham, NC (US); Shuai Li, Durham, NC (US)

(73) Assignee: Duke University, Durham, NC (US)

( * ) Notice: Subject to any disclaimer, the term of this patent is extended or adjusted under 35 U.S.C. 154(b) by 31 days.

(21) Appl. No.: 17/995,360

(22) PCT Filed: Apr. 2, 2021

(86) PCT No.: PCT/US2021/025487
§ 371 (c)(1),
(2) Date: Oct. 3, 2022

(87) PCT Pub. No.: WO2021/242408
PCT Pub. Date: Dec. 2, 2021

(65) Prior Publication Data
US 2023/0183757 A1 Jun. 15, 2023

Related U.S. Application Data

(60) Provisional application No. 63/004,740, filed on Apr. 3, 2020, provisional application No. 63/056,085, filed on Jul. 24, 2020.

(51) Int. Cl.
| | |
|---|---|
| *C12P 7/18* | (2006.01) |
| *C12N 1/20* | (2026.01) |
| *C12N 9/02* | (2006.01) |
| *C12N 9/04* | (2006.01) |
| *C12N 9/90* | (2006.01) |
| *C12N 15/113* | (2010.01) |
| *C12N 15/70* | (2006.01) |

(52) U.S. Cl.
CPC .................. *C12P 7/18* (2013.01); *C12N 1/20* (2013.01); *C12N 9/0006* (2013.01); *C12N 9/001* (2013.01); *C12N 9/90* (2013.01); *C12N 15/113* (2013.01); *C12N 15/70* (2013.01); *C12N 2500/34* (2013.01); *C12Y 101/01049* (2013.01); *C12Y 101/01307* (2013.01); *C12Y 103/0101* (2013.01); *C12Y 503/01005* (2013.01)

(58) Field of Classification Search
CPC ........... C12P 7/18; C12N 1/20; C12N 9/0006; C12N 9/001; C12N 9/90; C12N 15/113; C12N 15/70; C12N 2500/34; C12N 15/1137; C12N 2310/14; C12N 9/92; C12N 15/52; C12Y 101/01049; C12Y 101/01307; C12Y 103/0101; C12Y 503/01005; C12R 2001/19
See application file for complete search history.

(56) References Cited

U.S. PATENT DOCUMENTS

| | | | |
|---|---|---|---|
| 5,747,281 | A | 5/1998 | Shuler et al. |
| 7,745,177 | B2 | 6/2010 | Kim et al. |
| 7,960,152 | B2 | 6/2011 | Taylor et al. |
| 7,977,083 | B1 | 7/2011 | Sakakibara et al. |
| 8,663,962 | B2 | 3/2014 | Zhang et al. |
| 9,169,468 | B2 | 10/2015 | Zhang et al. |
| 9,611,515 | B2 | 4/2017 | Alviso et al. |
| 10,494,614 | B2 | 12/2019 | Schaefer et al. |
| 2003/0186402 | A1 | 10/2003 | Londesborough et al. |
| 2004/0132074 | A1 | 7/2004 | Verho et al. |
| 2006/0110805 | A1 | 5/2006 | Fotheringham |
| 2006/0110809 | A1 | 5/2006 | Taylor et al. |
| 2007/0259407 | A1 | 11/2007 | Verho et al. |
| 2008/0206821 | A1 | 8/2008 | Kim et al. |
| 2009/0209016 | A1 | 8/2009 | Londesborough et al. |
| 2011/0212458 | A1 | 9/2011 | Taylor et al. |
| 2012/0252074 | A1 | 10/2012 | Zhang et al. |
| 2012/0329109 | A1 | 12/2012 | Chua et al. |
| 2014/0127780 | A1 | 5/2014 | Zhang et al. |
| 2014/0322779 | A1 | 10/2014 | Burgard et al. |
| 2015/0073163 | A1 | 3/2015 | Chua et al. |
| 2015/0337340 | A1 | 11/2015 | Alvizo et al. |
| 2016/0040139 | A1 | 2/2016 | Zhang et al. |
| 2019/0390232 | A1 | 12/2019 | Lynch et al. |
| 2020/0032224 | A1 | 1/2020 | Schaefer et al. |

FOREIGN PATENT DOCUMENTS

| | | |
|---|---|---|
| CN | 104593308 B | 7/2017 |
| JP | 2007-510411 A | 4/2007 |
| JP | 2017-517268 A5 | 5/2018 |
| JP | 2020-508050 B2 | 3/2020 |

(Continued)

OTHER PUBLICATIONS

Whisstock et al. Quaterly Reviews of Biophysics, 2003, "Prediction of protein function from protein sequence and structure", 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10:8-9. (Year: 2002).*

Olubolaji Akinterinwa (Improving the efficiency of NADPH-dependent xylitol production in engineered *Escherichia coli*. PhD Thesis, Pennsylvania State University (2010, p. 1-237) (Year: 2010).*

(Continued)

*Primary Examiner* — Iqbal H Chowdhury

(74) *Attorney, Agent, or Firm* — Benesch Friedlander Coplan & Aronoff LLP

(57) ABSTRACT

The present disclosure is related to genetically engineered microbial strains and related bioprocesses for the production of xylitol. Specifically, the use of dynamically controlled synthetic metabolic valves to reduce the activity of certain enzymes, leads to increased xylitol production in a two-stage process.

22 Claims, 19 Drawing Sheets

Specification includes a Sequence Listing.

(56) References Cited

FOREIGN PATENT DOCUMENTS

| NO | 2018112634 A1 | 6/2018 |
|---|---|---|
| WO | 2002066616 A2 | 8/2002 |
| WO | 2005026339 A1 | 3/2005 |
| WO | 2005113759 A2 | 12/2005 |
| WO | 2005113774 A2 | 12/2005 |
| WO | 2012135110 A1 | 10/2012 |
| WO | 2012154626 A1 | 11/2012 |
| WO | 2014081605 A1 | 5/2014 |
| WO | 2016/053397 A2 | 4/2016 |
| WO | 2016/084963 A1 | 6/2016 |
| WO | 2018156646 A1 | 8/2018 |
| WO | 2019246488 A1 | 12/2019 |

OTHER PUBLICATIONS

Hasper et al. (The Aspergillus niger transcriptional activator XInR, which is involved in the degradation of the polysaccharides xylan and cellulose, also regulates D-xylose reductase gene expression. Molecular Microbiology (2000), 36(1): 193-200) (Year: 2000).*

Witteveen et al. L-Arabinose and D-Xylose catabolismin Aspergillus niger. Microbiology (1989), 135(8): 2163-2171. (Year: 1989).*

International Search Report and Written Opinion issued in PCT application No. PCT/US21/25487, mailing date Feb. 18, 2022.

Chin et al., Analysis of NADPH Supply During Xylitol Production by Engineered *Escherichia coli*. Biotechnology and Bioengineering. Jan. 1, 2009, vol. 102, No. 1, pp. 209-220; abstract; p. 209, para 1; p. 212, col. 2, para 1; p. 214, col. 2, para 2.

Hasper et al., The Aspergillus niger transcriptional activator XInR, which is involved in the degradation of the polysaccharides xylan and cellulose, also regulates D-xylose reductase gene expression. Molecular Microbiology. Apr. 2000, vol. 36, No. 1, pp. 193-200; abstract.

Gao et al., Programmable biomolecular switches for rewiring flux in *Escherichia coli*. Nature. Aug. 21, 2019, vol. 10, article 3751, pp. 1-12; abstract; p. 10, col. 1, para 3.

International Preliminary Report on Patentability issued in PCT application No. PCT/US21/25487, dated Dec. 17, 2022.

Xu, Y. R., et al., "Biosynthetic strategies to produce xylitol: an economical venture", Appl. Microbiol. Biotechnol. 2019, 103 (13), 5143-5160.

De Albuquerque, T. L., et al., "Biotechnological production of xylitol from lignocellulosic wastes: A review", Process Biochemistry 2014, 49 (11), 1779-1789.

Hallborn, J., et al., "Xylitol Production by Recombinant *Saccharomyces cerevisiae*", Bio/Technology 1991, 9 (11), 1090-1095.

Prakash, G., et al., "Microbial production of xylitol from D-xylose and sugarcane bagasse hemicellulose using newly solated thermotolerant yeast *Debaryomyces hansenii*", Bioresource Technology 2011, 102 (3), 3304-3308.

Wiebe, M. G., et al., A novel aldose-aldose oxidoreductase for co-production of D-xylonate and xylitol from D-xylose with *Saccharomyces cerevisiae*, Appl. Microbiol. Biotechnol. 2015, 99 (22), 9439-9447.

Saito, K., et al., "Production of lactic acid from xylose and wheat straw by Rhizopus oryzae", Journal of Bioscience and Bioengineering 2012, 114 (2), 166-169.

Qureshi, N., et al., "Genetically engineered *Escherichia coli* for ethanol production from xylose—Substrate and product inhibition and kinetic parameters", Food and Bioproducts Processing 2006, 84 (C2), 114-122.

Ong, K. L., et al., "Co-fermentation of glucose and xylose from sugarcane bagasse into succinic acid by Yarrowia lipolytica", Biochemical Engineering Journal 2019, 148, 108-115.

Chen, X., et al., "Microbial and Bioconversion Production of D-xylitol and Its Detection and Application", International Journal of Biological Sciences 2010, 6 (7), 834-844.

Liavoga, A. B., "D-Xylose produced from wheat straw by acid and enzyme catalyzed hydrolysis, and the purification of xylitol", Ph.D., Kansas State University, Ann Arbor, 2006.

Rao, R. S., et al., "Xylitol production from corn fiber and sugarcane bagasse hydrolysates by Candida tropicalis", Bioresource Technology 2006, 97 (15), 1974-1978.

Jin, L.-Q., et al., "Efficient Biosynthesis of Xylitol from Xylose by Coexpression of Xylose Reductase and Glucose Dehydrogenase in *Escherichia coli*", Applied Biochemistry and Biotechnology 2019, 187 (4), 1143-1157.

Kim, S.-H., et al., "Production of xylitol from d-xylose and glucose with recombinant Corynebacterium glutamicum", Enzyme and Microbial Technology 2010, 46 (5), 366-371.

Nyyssola, A., et al., "Production of xylitol from d-xylose by recombinant Lactococcus lactis", Journal of Biotechnology 2005, 118 (1), 55-66.

Burg, J. M., et al., "Large-scale bioprocess competitiveness: the potential of dynamic metabolic control in two-stage fermentations", Current Opinion in Chemical Engineering 2016, 14, 121-136.

Chen, Z., et al., "Metabolic engineering of Corynebacterium glutamicum for the production of 3-hydroxypropionic acid from glucose and xylose", Metabolic Engineering 2017, 39, 151-158.

Shiue, E., et al., "Improving d-glucaric acid production from myo-inositol in *E. coli* by increasing MIOX stability and myo-inositol transport", Metabolic Engineering 2014, 22, 22-31.

Luo, M. L., et al., "Repurposing endogenous type I CRISPR-Cas systems for programmable gene repression", Nucleic Acids Research 2014, 43 (1), 674-681.

Mcginness, K. E., et al., "Engineering Controllable Protein Degradation", Molecular Cell 2006, 22 (5), 701-707.

Moreb, E. A., et al., "Robustness testing and scalability of phosphate regulated promoters useful for two-stage autoinduction in <em>E. coli</em>", bioRxiv 2020, 2020.01.26.920280.

Menacho-Melgar, R., et al., "Improved, scalable, two-stage, autoinduction of recombinant protein expression in <em>E. coli</em> utilizing phosphate depletion", bioRxiv 2020, 820787.

Sauer, U., et al., "The soluble and membrane-bound transhydrogenases UdhA and PntAB have divergent functions In NADPH metabolism of *Escherichia coli*", Journal of Biological Chemistry 2004, 279 (8), 6613-6619.

Park, S. J., et al., "Regulation of the citrate synthase (gltA) gene of *Escherichia coli* in response to anaerobiosis and carbon supply: role of the arcA gene product", Journal of Bacteriology 1994, 176 (16), 5086-5092.

Zhao, J., et al., "Effect of zwf gene knockout on the metabolism of *Escherichia coli* grown on glucose or acetate", Metabolic Engineering 2004, 6 (2), 164-174.

Sharan, S. K., et al., "Recombineering: a homologous recombination-based method of genetic engineering", Nature Protocols 2009, 4 (2), 206-223.

Suzuki, T., et al., "Expression of xyrA gene encoding for d-Xylose reductase of Candida tropicalis and production of xylitol in *Escherichia coli*", Journal of Bioscience and Bioengineering 1999, 87 (3), 280-284.

European Search Report issued in European patent application No. 21811936.0, dated Aug. 16, 2023.

Examination Report issued in European patent application No. 21811936.0, dated Aug. 29, 2023.

Lynch Michael et al: "Standarized two-stage bioprocess development using synthetic metabolic valves and dynamic metabolic control", abstracts of papers ; ACS National Meeting & Exposition; 249th National Meeting and Exposition of the American-Chemical-Society (ACS), American Chemical Society, US; Denver, CO, USA, vol. 249, Mar. 22, 2015 (Mar. 22, 2015), p. BIOT418, XP009502426.

Li Shuai et al: "Dynamic control over feedback regulatory mechanisms improves NADPH flux and xylitol biosynthesis in engineered *E. coli*", Metabolic Engineering, vol. 64, Mar. 1, 2021 (Mar. 1, 2021), pp. 26-40, XP093070873,Amsterdam, NLISSN: 1096-7176, DOI:10.1016/j.ymben.2021.01.005.

Ye Zhixia et al: "*Escherichia coli* Casl/2 Endonuclease Complex Modifies Self-Targeting CRISPR/Cascade Spacers Reducing Silencing Guide Stability", ACS Synthetic Biology, vol. 10, No. 1, Dec.

(56)        References Cited

OTHER PUBLICATIONS 17, 2020 (Dec. 17, 2020), pp. 29-37, XP093054808,Washington DC ,USAISSN: 2161-5063, DOI:10.1021/acssynbio.0c00398.

Li Shuai et al: "Dynamic control over feedback regulation identifies pyruvate-ferredoxin oxidoreductase as a central metabolic enzyme in stationary phase *E. coli*" , bioRxiv, Aug. 10, 2020 (Aug. 10, 2020), XP093071135, DOI: 10.1101/2020.07.26.219949 Retrieved from the Internet: URL:https://www.biorxiv.org/content/10.1101/2020.07.26.219949v2.

Corrected International Preliminary Report on Patentability issued in PCT/US2021/025487, dated Feb. 5, 2023.

Office Action issued in Canadian Patent Application No. 3,179,180, dated Apr. 2, 2024.

Examination Report issued in European Patent Application No. 21811936.0, dated Jun. 26, 2024.

Examination Report issued in European Patent Application No. 21811936.0, dated Nov. 18, 2024.

Office Action issued in Japanese Patent Application No. 2022-560304, dated Mar. 28, 2025.

Su, B., et al., "Efficient production of xylitol from hemicellulosic hydrolysate using engineered *Escerichia coli*", Metabolic Engineering 31 (2015) 112-122.

Wei, L., et al., "Effect of NADPH availability on free fatty acid production in *Escherichia coli*", Biotechnology and Bioengineering, 2018; 155: 444-452.

Examination Report issued in Indonesian Application No. P00202212179, issued May 28, 2025.

Substantive Examination Report issued in Indonesian Patent Application No. P00202212179, dated Oct. 9, 2025.

Examination Report issued in Australian Patent Application No. 2021278792 dated Nov. 27, 2025.

Substantive Examination Report and Search Report issued in Malaysian Patent Application No. PI2022005484, dated Dec. 5, 2025.

Decision of Refusal issued in Japanese Patent Application No. 2022-560304, dated Dec. 16, 2025.

* cited by examiner

| | Vmax(U) | Kcat(s⁻¹) | Km(uM) | Source |
|---|---|---|---|---|
| 1 | 75 | | 39 | 1 |
| 2 | 23.2 | 13 | 96 | 2 |
| 3 | | 13.5 | 42 | 3 |
| 4 | 22.6 | | 35 | This Study |

A)

B)

A)

B)

A)

B)

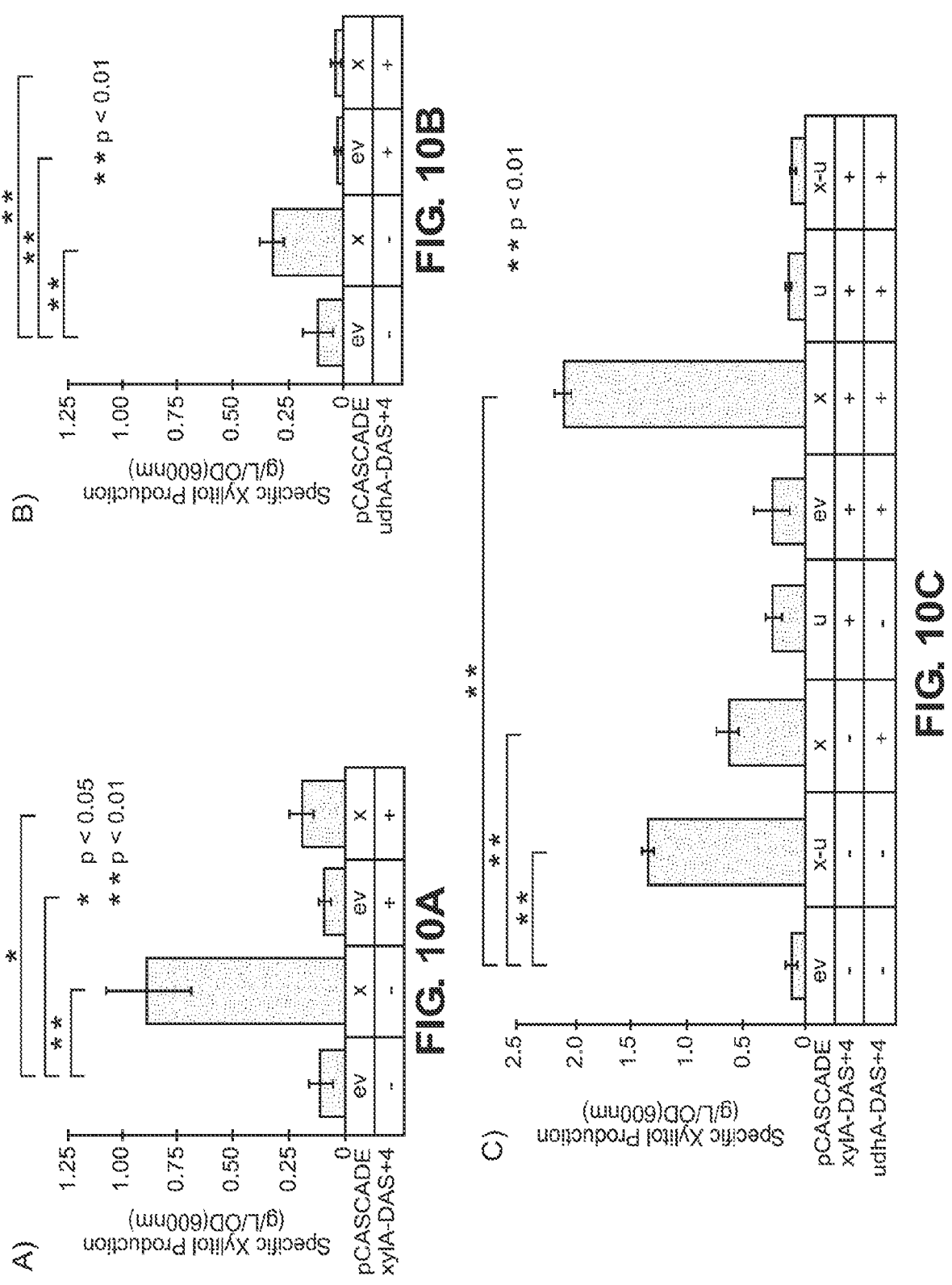

A)
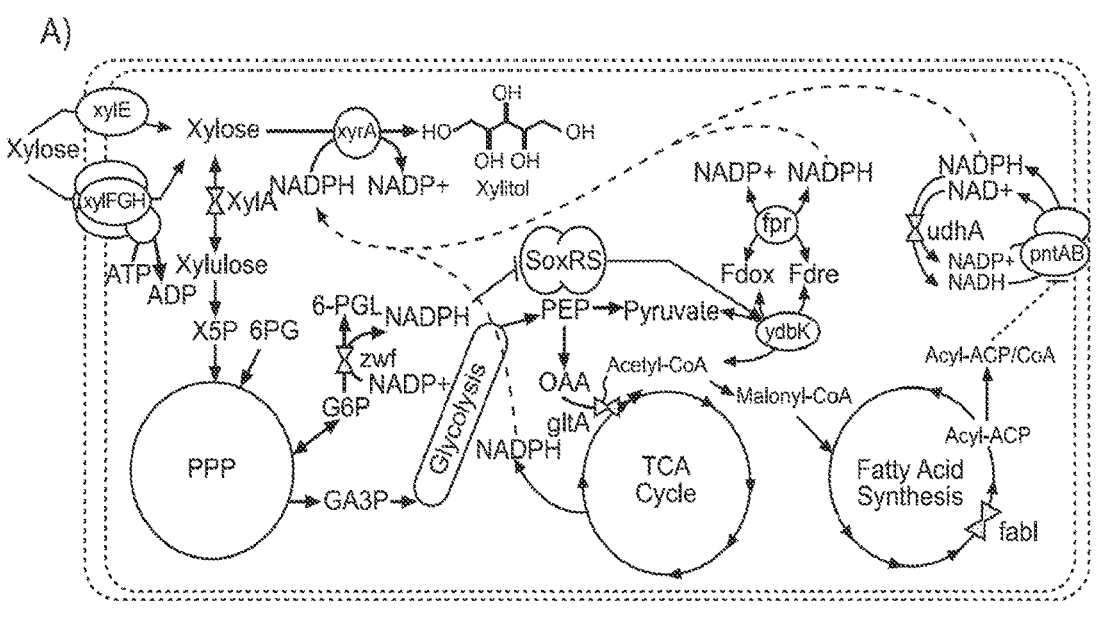
FIG. 12A
B)
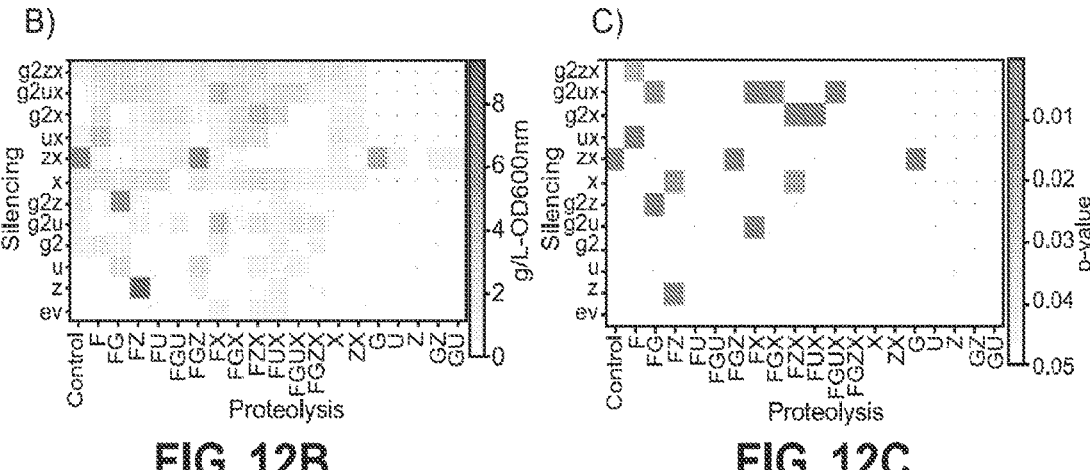
FIG. 12B
C)
FIG. 12C
D)
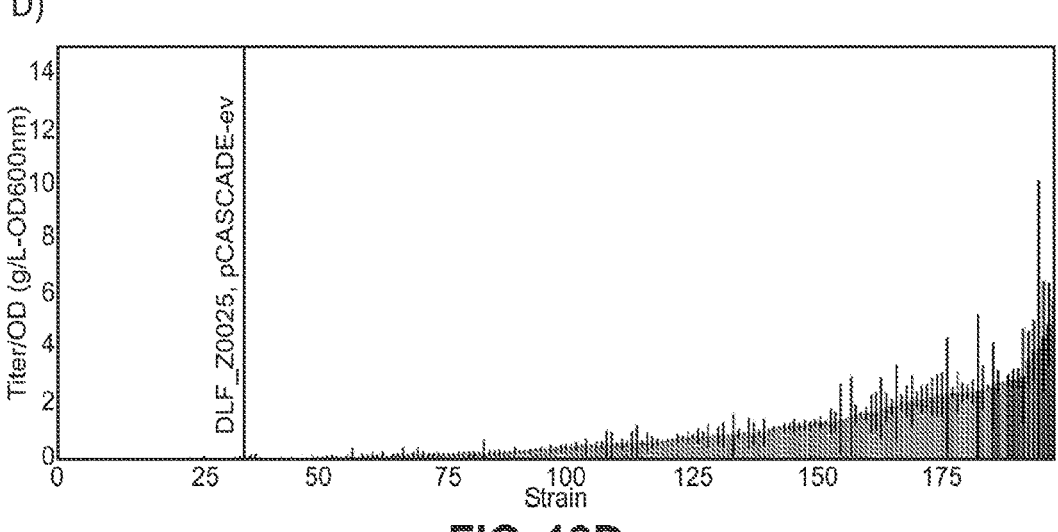
FIG. 12D

A)

B)

SEQUENCE LISTING

```
<160> NUMBER OF SEQ ID NOS: 31

<210> SEQ ID NO 1
<211> LENGTH: 1487
<212> TYPE: DNA
<213> ORGANISM: Artificial Sequence
<220> FEATURE:
<223> OTHER INFORMATION: Synthetic

<400> SEQUENCE: 1
gatacgatgg cactggcgct gaaaattgca gcgcgcatga ttgaagatgg cgagctggat        60
aaacgcatcg cgcagcgtta ttccggctgg aatagcgaat tgggccagca aatcctgaaa       120
ggccaaatgt cactggcaga tttagccaaa tatgctcagg aacatcattt gtctccggtg       180
catcagagtg gtcgccagga acaactggaa aatctggtaa accattatct gttcgacaaa       240
gcggccaacg atgaaaacta ttctgaaaac tatgcggatg cgtcttaatg ataaggaccg       300
tgttgacaat taatcatcgg catagtatat cggcatagta taatacgaca aggtgaggaa       360
ctaaaccatg agtattcaac atttccgtgt cgcccttatt cccttttttg cggcattttg       420
ccttcctgtt tttgctcacc cagaaacgct ggtgaaagta aaagatgctg aagatcagtt       480
gggtgcacga gtgggttaca tcgaactgga tctcaacagc ggtaagatcc ttgagagttt       540
acgccccgaa gaacgttttc caatgatgag cacttttaaa gttctgctat gtggcgcggt       600
attatcccgt attgacgccg ggcaagagca actcggtcgc cgcatacact attctcagaa       660
tgacttggtt gagtactcac cagtcacaga aaagcatctc acggatggca tgacagtaag       720
agaattatgc agtgctgcca taaccatgag tgataacact gcggccaact tacttctggc       780
aacgatcgga ggaccgaagg agctaaccgc tttttttgcac aacatggggg atcatgtaac       840
tcgccttgat cgttgggaac cggagctgaa tgaagccata ccaaacgacg agcgtgacac       900
cacgatgcct gtagcaatgg caacaacgtt gcgcaaacta ttaactggcg aactacttac       960
tctagcttcc cggcaacaat taatagactg gatggaggcg gataaagttg caggatcact      1020
```

```
tctgcgctcg gccctcccgg ctggctggtt tattgctgat aaatctggag ccggtgagcg     1080
tgggtctcgc ggtatcattg cagcactggg gccagatggt aagccctccc gcatcgtagt     1140
tatctacacg acggggagtc aggcaactat ggatgaacga aatagacaga tcgctgagat     1200
aggtgcctca ctgattaagc attggtagta agtagggata acagggtaat cggctaactg     1260
tgcagtccgt tggcccggtt atcggtagcg ataccgggca ttttttttaag gaacgatcga    1320 tatgtatatc gggatagatc ttggcacctc gggcgtaaaa gttattttgc tcaacgagca     1380
gggtgaggtg gttgctgcgc aaacggaaaa gctgaccgtt tcgcgcccgc atccactctg     1440
gtcggaacaa gacccggaac agtggtggca ggcaactgat cgcgcaa                    1487

<210> SEQ ID NO 2
<211> LENGTH: 970
<212> TYPE: DNA
<213> ORGANISM: Artificial Sequence
<220> FEATURE:
<223> OTHER INFORMATION: Synthetic

<400> SEQUENCE: 2
ctattgaaga tgtgggtaac tctgcggcat tcctgtgctc cgatctctct gccggtatct       60
ccggtgaagt ggtccacgtt gacggcggtt tcagcattgc tgcaatgaac gaactcgaac      120
tgaaagcggc caacgatgaa aactattctg aaaactatgc ggatgcgtct taataggaag      180
ttcctattct ctagaaagta taggaacttc cgaatccatg tgggagttta ttcttgacac      240
agatatttat gatataataa ctgagtaagc ttaacataag gaggaaaaac atatgttacg      300
cagcagcaac gatgttacgc agcagggcag tcgccctaaa acaaagttag gtggctcaag      360
tatgggcatc attcgcacat gtaggctcgg ccctgaccaa gtcaaatcca tgcgggctgc      420
tcttgatctt ttcggtcgtg agttcggaga cgtagccacc tactcccaac atcagccgga      480
ctccgattac ctcgggaact tgctccgtag taagacattc atcgcgcttg ctgccttcga      540
ccaagaagcg gttgttggcg ctctcgcggc ttacgttctg cccaagtttg agcagccgcg      600
tagtgagatc tatatctatg atctcgcagt ctccggcgag caccggaggc agggcattgc      660
caccgcgctc atcaatctcc tcaagcatga ggccaacgcg cttggtgctt atgtgatcta      720
cgtgcaagca gattacggtg acgatcccgc agtggctctc tatacaaagt tgggcatacg      780
ggaagaagtg atgcactttg tatcgaccc aagtaccgcc acctaagaag ttcctattct      840
ctagaaagta taggaacttc cgttctgttg gtaaagatgg gcggcgttct gccgcccgtt      900
atctctgtta tacctttctg atatttgtta tcgccgatcc gtctttctcc ccttcccgcc      960
ttgcgtcagg                                                              970

<210> SEQ ID NO 3
<211> LENGTH: 869
<212> TYPE: DNA
<213> ORGANISM: Artificial Sequence
<220> FEATURE:
<223> OTHER INFORMATION: Synthetic

<400> SEQUENCE: 3
gtattccgtc ttccatgttc accgtcattt tcgcaatggc acgtaccgtt ggctggatcg        60
cccactggag cgaaatgcac agtgacggta tgaagattgc ccgtccgcgt cagctgtata      120
caggatatga aaacgcgac tttaaaagcg atatcaagcg tgcggccaac gatgaaaact       180
attctgaaaa ctatgcggat gcgtcttaat agttgacaat taatcatcgg catagtatat      240
cggcatagta taatacgact cactatagga gggccatcat ggccaagttg accagtgccg      300
```

-continued

```
ttccggtgct caccgcgcgc gacgtcgccg gagcggtcga gttctggacc gaccggctcg      360
ggttctcccg ggacttcgtg gaggacgact tcgccggtgt ggtccgggac gacgtgaccc      420
tgttcatcag cgcggtccag gaccaggtgg tgccggacaa caccctggcc tgggtgtggg      480
tgcgcggcct ggacgagctg tacgccgagt ggtcggaggc cgtgtccacg aacttccggg      540
acgcctccgg gccggccatg accgagatcg gcgagcagcc gtgggggcgg gagttcgccc      600
tgcgcgaccc ggccggcaac tgcgtgcact ttgtggcaga ggagcaggac tgaggataag      660
taatggttga ttgctaagtt gtaaatattt aacccgccg ttcatatggc gggttgattt       720
ttatatgcct aaacacaaaa aattgtaaaa ataaaatcca ttaacagacc tatatagata      780
tttaaaaaga atagaacagc tcaaattatc agcaacccaa tactttcaat taaaaacttc      840
atggtagtcg catttataac cctatgaaa                                         869
```

```
<210> SEQ ID NO 4
<211> LENGTH: 852
<212> TYPE: DNA
<213> ORGANISM: Artificial Sequence
<220> FEATURE:
<223> OTHER INFORMATION: Synthetic

<400> SEQUENCE: 4
```

```
tctgggtatt cactgctttg gcgagcgcgc tgccgaaatt attcatatcg gtcaggcgat       60
tatggaacag aaaggtggcg gcaacactat tgagtacttc gtcaacacca cctttaacta      120
cccgacgatg gcggaagcct atcgggtagc tgcgttaaac ggtttaaacc gcctgtttgc      180
ggccaacgat gaaaactatt ctgaaaacta tgcggatgcg tcttaatagt tgacaattaa      240
tcatcggcat agtatatcgg catagtataa tacgactcac tataggaggg ccatcatgaa      300
gaccttcaac atctctcagc aggatctgga gctggtggag gtcgccactg agaagatcac      360
catgctctat gaggacaaca agcaccatgt cggggcggcc atcaggacca agactgggga      420
gatcatctct gctgtccaca ttgaggccta cattggcagg gtcactgtct gtgctgaagc      480
cattgccatt gggtctgctg tgagcaacgg gcagaaggac tttgacacca ttgtggctgt      540
caggcacccc tactctgatg aggtggacag atccatcagg gtggtcagcc cctgtggcat      600
gtgcagagag ctcatctctg actatgctcc tgactgcttt gtgctcattg agatgaatgg      660
caagctggtc aaaaccacca ttgaggaact catcccctc aagtacacca ggaactaaag       720
taaaacttta tcgaaatggc catccattct tgcgcggatg gcctctgcca gctgctcata      780
gcggctgcgc agcggtgagc caggacgata aaccaggcca atagtgcggc gtggttccgg      840
cttaatgcac gg                                                          852
```

```
<210> SEQ ID NO 5
<211> LENGTH: 898
<212> TYPE: DNA
<213> ORGANISM: Artificial Sequence
<220> FEATURE:
<223> OTHER INFORMATION: Synthetic

<400> SEQUENCE: 5
```

```
gaagtggaag aagcctggaa atgggtagac tccattactg aggcgtgggc gatggacaat       60
gatgcgccga aaccgtatca ggccggaacc tggggacccg ttgcctcggt ggcgatgatt      120
acccgtgatg gtcgttcctg gaatgagttt gaggcggcca acgatgaaaa ctattctgaa      180
aactatgcgg atgcgtctta atagttgaca attaatcatc ggcatagtat atcggcatag      240
```

-continued

```
tataatacga ctcactatag gagggccatc atgaagacct tcaacatctc tcagcaggat      300
ctggagctgg tggaggtcgc cactgagaag atcaccatgc tctatgagga caacaagcac      360
catgtcgggg cggccatcag gaccaagact ggggagatca tctctgctgt ccacattgag      420
gcctacattg gcagggtcac tgtctgtgct gaagccattg ccattgggtc tgctgtgagc      480
aacgggcaga aggactttga caccattgtg gctgtcaggc acccctactc tgatgaggtg      540
gacagatcca tcagggtggt cagcccctgt ggcatgtgca gagagctcat ctctgactat      600
gctcctgact gctttgtgct cattgagatg aatggcaagc tggtcaaaac caccattgag      660
gaactcatcc ccctcaagta caccaggaac taaagtaata tctgcgctta tcctttatgg      720
ttattttacc ggtaacatga tcttgcgcag attgtagaac aatttttaca ctttcaggcc      780
tcgtgcggat tcacccacga ggctttttt attacactga ctgaaacgtt tttgccctat      840
gagctccggt tacaggcgtt tcagtcataa atcctctgaa tgaaacgcgt tgtgaatc      898
```

```
<210> SEQ ID NO 6
<211> LENGTH: 93
<212> TYPE: DNA
<213> ORGANISM: Artificial Sequence
<220> FEATURE:
<223> OTHER INFORMATION: Synthetic

<400> SEQUENCE: 6
tcgagttccc cgcgccagcg gggataaacc gaaaagcata taatgcgtaa aagttatgaa       60
gttcgagttc cccgcgccag cggggataaa ccg                                    93
```

```
<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
ccggatgagc attcatcagg cgggcaag                                          28
```

```
<210> SEQ ID NO 8
<211> LENGTH: 47
<212> TYPE: DNA
<213> ORGANISM: Artificial Sequence
<220> FEATURE:
<223> OTHER INFORMATION: Synthetic

<400> SEQUENCE: 8
cggtttatcc ccgctggcgc ggggaactcg aacttcataa cttttac                    47
```

```
<210> SEQ ID NO 9
<211> LENGTH: 63
<212> TYPE: DNA
<213> ORGANISM: Artificial Sequence
<220> FEATURE:
<223> OTHER INFORMATION: Synthetic

<400> SEQUENCE: 9
tattgaccaa ttcattcggg acagttatta gttcgagttc cccgcgccag cggggataaa       60
ccg                                                                     63
```

```
<210> SEQ ID NO 10
<211> LENGTH: 28
<212> TYPE: DNA
<213> ORGANISM: Artificial Sequence
```

```
<220> FEATURE:
<223> OTHER INFORMATION: Synthetic

<400> SEQUENCE: 10
ccggatgagc attcatcagg cgggcaag                                    28

<210> SEQ ID NO 11
<211> LENGTH: 44
<212> TYPE: DNA
<213> ORGANISM: Artificial Sequence
<220> FEATURE:
<223> OTHER INFORMATION: Synthetic

<400> SEQUENCE: 11
cggtttatcc ccgctggcgc ggggaactcg aactaataac tgtc                  44

<210> SEQ ID NO 12
<211> LENGTH: 61
<212> TYPE: DNA
<213> ORGANISM: Artificial Sequence
<220> FEATURE:
<223> OTHER INFORMATION: Synthetic

<400> SEQUENCE: 12
ttaccattct gttgctttta tgtataagaa tcgagttccc cgcgccagcg gggataaacc   60
g                                                                 61

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
ccggatgagc attcatcagg cgggcaag                                    28

<210> SEQ ID NO 14
<211> LENGTH: 48
<212> TYPE: DNA
<213> ORGANISM: Artificial Sequence
<220> FEATURE:
<223> OTHER INFORMATION: Synthetic

<400> SEQUENCE: 14
cggtttatcc ccgctggcgc ggggaactcg attcttatac ataaaagc              48

<210> SEQ ID NO 15
<211> LENGTH: 61
<212> TYPE: DNA
<213> ORGANISM: Artificial Sequence
<220> FEATURE:
<223> OTHER INFORMATION: Synthetic

<400> SEQUENCE: 15
ctcgtaaaag cagtacagtg caccgtaaga tcgagttccc cgcgccagcg gggataaacc   60
g                                                                 61

<210> SEQ ID NO 16
<211> LENGTH: 28
<212> TYPE: DNA
<213> ORGANISM: Artificial Sequence
<220> FEATURE:
<223> OTHER INFORMATION: Synthetic
```

```
<400> SEQUENCE: 16
ccggatgagc attcatcagg cgggcaag                                       28

<210> SEQ ID NO 17
<211> LENGTH: 49
<212> TYPE: DNA
<213> ORGANISM: Artificial Sequence
<220> FEATURE:
<223> OTHER INFORMATION: Synthetic

<400> SEQUENCE: 17
cggtttatcc ccgctggcgc ggggaactcg atcttacggt gcactgtac               49

<210> SEQ ID NO 18
<211> LENGTH: 61
<212> TYPE: DNA
<213> ORGANISM: Artificial Sequence
<220> FEATURE:
<223> OTHER INFORMATION: Synthetic

<400> SEQUENCE: 18
ggagtgccca atattacgac atcatccatc tcgagttccc cgcgccagcg gggataaacc   60
g                                                                   61

<210> SEQ ID NO 19
<211> LENGTH: 34
<212> TYPE: DNA
<213> ORGANISM: Artificial Sequence
<220> FEATURE:
<223> OTHER INFORMATION: Synthetic

<400> SEQUENCE: 19
ccagcgggga taaaccggga gtgcccaata ttac                               34

<210> SEQ ID NO 20
<211> LENGTH: 28
<212> TYPE: DNA
<213> ORGANISM: Artificial Sequence
<220> FEATURE:
<223> OTHER INFORMATION: Synthetic

<400> SEQUENCE: 20
cttgcccgcc tgatgaatgc tcatccgg                                      28

<210> SEQ ID NO 21
<211> LENGTH: 1655
<212> TYPE: DNA
<213> ORGANISM: Artificial Sequence
<220> FEATURE:
<223> OTHER INFORMATION: Synthetic

<400> SEQUENCE: 21
aaagacttcc gcaaaatgct ggctcattgc gaagccgtta ccccgattcg ccgtaccgtt   60
actattgaag atgtgggtaa ctctgcggca ttcctgtgct ccgatctctc tgccggtatc   120
tccggtgaag tggtccacgt tgacggcggt ttcagcattg ctgcaatgaa cgaactcgaa   180
ctgaaagggg gttcaggcgg gtcgggtggc gtgagcaagg gcgaggagct gttcaccggg   240
gtggtgccca tcctggtcga gctggacggc gacgtaaacg gccacaagtt cagcgtgcgc   300
ggcgagggcg agggcgatgc caccaacggc aagctgaccc tgaagttcat ctgcaccacc   360
ggcaagctgc ccgtgccctg gcccaccctc gtgaccaccc tgacctacgg cgtgcagtgc   420
ttcagccgct accccgacca catgaagcgc cacgacttct tcaagtccgc catgcccgaa   480
```

-continued

```
ggctacgtcc aggagcgcac catcagcttc aaggacgacg gcacctacaa gacccgcgcc      540
gaggtgaagt tcgagggcga caccctggtg aaccgcatcg agctgaaggg catcgacttc      600
aaggaggacg gcaacatcct ggggcacaag ctggagtaca acttcaacag ccacaacgtc      660
tatatcaccg ccgacaagca gaagaacggc atcaaggcca acttcaagat ccgccacaac      720
gtggaggacg gcagcgtgca gctcgccgac cactaccagc agaacacccc catcggcgac      780
ggccccgtgc tgctgcccga caaccactac ctgagcaccc agtccgtgct gagcaaagac      840
cccaacgaga gcgcgatca catggtcctg ctggagttcg tgaccgccgc cgggatcact       900
cacggcatgg acgagctgta caagtaatga cgaatccatg tgggagttta ttcttgacac      960
agatatttat gatataataa ctgagtaagc ttaacataag gaggaaaaac atatgttgcg     1020
tagctctaac gatgtgacgc aacaaggttc gcgtccaaag acaaaattgg gaggcagtag     1080
catggggatc attcgcactt gtcgcctggg gccagaccag gtgaagtcaa tgcgtgcggc     1140
tctggactta ttcgggcgcg aatttggaga tgtagccact tactcacagc accaaccgga     1200
cagtgattac ttggggaatt tacttcgcag taaaactttt atcgctttgg ccgctttcga     1260
ccaggaggct gtagtaggtg cgttggcagc ctatgttctt cctaaattcg agcaaccgcg     1320
tagcgaaatt tacatctatg atcttgcagt ctccggcgaa catcgccgtc aggggatcgc     1380
cacagcttta atcaaccttt tgaagcatga ggctaatgca cttggagcgt acgtgattta     1440
tgtgcaggct gactacggtg atgatcctgc agtcgctctg tacaccaaac tgggtatccg     1500
cgaggaggtc atgcactttg atattgaccc gtcgacggct acctaagttc tgttggtaaa     1560
gatgggcggc gttctgccgc ccgttatctc tgttatacct ttctgatatt tgttatcgcc     1620
gatccgtctt tctcccctc ccgccttgcg tcagg                                 1655
```

```
<210> SEQ ID NO 22
<211> LENGTH: 1730
<212> TYPE: DNA
<213> ORGANISM: Artificial Sequence
<220> FEATURE:
<223> OTHER INFORMATION: Synthetic

<400> SEQUENCE: 22
aaagacttcc gcaaaatgct ggctcattgc gaagccgtta ccccgattcg ccgtaccgtt       60
actattgaag atgtgggtaa ctctgcggca ttcctgtgct ccgatctctc tgccggtatc      120
tccggtgaag tggtccacgt tgacggcggt ttcagcattg ctgcaatgaa cgaactcgaa      180
ctgaaagggg gttcaggcgg gtcgggtggc gtgagcaagg gcgaggagct gttcaccggg      240
gtggtgccca tcctggtcga gctggacggc gacgtaaacg gccacaagtt cagcgtgcgc      300
ggcgagggcg agggcgatgc caccaacggc aagctgaccc tgaagttcat ctgcaccacc      360
ggcaagctgc ccgtgccctg gcccaccctc gtgaccaccc tgacctacgg cgtgcagtgc      420
ttcagccgct accccgacca catgaagcgc acgacttct tcaagtccgc catgcccgaa       480
ggctacgtcc aggagcgcac catcagcttc aaggacgacg gcacctacaa gacccgcgcc      540
gaggtgaagt tcgagggcga caccctggtg aaccgcatcg agctgaaggg catcgacttc      600
aaggaggacg gcaacatcct ggggcacaag ctggagtaca acttcaacag ccacaacgtc      660
tatatcaccg ccgacaagca gaagaacggc atcaaggcca acttcaagat ccgccacaac      720
gtggaggacg gcagcgtgca gctcgccgac cactaccagc agaacacccc catcggcgac      780
ggccccgtgc tgctgcccga caaccactac ctgagcaccc agtccgtgct gagcaaagac      840
```

-continued

```
cccaacgaga agcgcgatca catggtcctg ctggagttcg tgaccgccgc cgggatcact    900
cacggcatgg acgagctgta caagggtggg ggtgggagcg gcggcggtgg ctccgcggcc    960
aacgatgaaa actattctga aaactatgcg gatgcgtctt aatgacgaat ccatgtggga   1020
gtttattctt gacacagata tttatgatat aataactgag taagcttaac ataaggagga   1080
aaaacatatg ttgcgtagct ctaacgatgt gacgcaacaa ggttcgcgtc caaagacaaa   1140
attgggaggc agtagcatgg ggatcattcg cacttgtcgc ctggggccag accaggtgaa   1200
gtcaatgcgt gcggctctgg acttattcgg gcgcgaattt ggagatgtag ccacttactc   1260
acagcaccaa ccggacagtg attacttggg gaatttactt cgcagtaaaa cttttatcgc   1320
tttggccgct ttcgaccagg aggctgtagt aggtgcgttg gcagcctatg ttcttcctaa   1380
attcgagcaa ccgcgtagcg aaatttacat ctatgatctt gcagtctccg gcgaacatcg   1440
ccgtcagggg atcgccacag ctttaatcaa cctttgaag catgaggcta atgcacttgg   1500
agcgtacgtg atttatgtgc aggctgacta cggtgatgat cctgcagtcg ctctgtacac   1560
caaactgggt atccgcgagg aggtcatgca ctttgatatt gacccgtcga cggctaccta   1620
agttctgttg gtaaagatgg gcggcgttct gccgcccgtt atctctgtta tacctttctg   1680
atatttgtta tcgccgatcc gtctttctcc ccttcccgcc ttgcgtcagg               1730
```

```
<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
gcaaaatgct ggctcattg                                                   19

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
gcgatgaatg tcttactacg ga                                               22

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
tatcatcctg aaagcgatgg                                                  20

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
actgaagccc agacgatc                                                    18
```

-continued

```
<210> SEQ ID NO 27
<211> LENGTH: 17
<212> TYPE: DNA
<213> ORGANISM: Artificial Sequence
<220> FEATURE:
<223> OTHER INFORMATION: Synthetic

<400> SEQUENCE: 27
ctgctggaaa ccatgcg                                                          17

<210> SEQ ID NO 28
<211> LENGTH: 24
<212> TYPE: DNA
<213> ORGANISM: Artificial Sequence
<220> FEATURE:
<223> OTHER INFORMATION: Synthetic

<400> SEQUENCE: 28
caaaagagat tctgggtatt cact                                                  24

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
gagcatggtg atcttctcag t                                                     21

<210> SEQ ID NO 30
<211> LENGTH: 17
<212> TYPE: DNA
<213> ORGANISM: Artificial Sequence
<220> FEATURE:
<223> OTHER INFORMATION: Synthetic

<400> SEQUENCE: 30
agatggcgag ctggata                                                          17

<210> SEQ ID NO 31
<211> LENGTH: 22
<212> TYPE: DNA
<213> ORGANISM: Artificial Sequence
<220> FEATURE:
<223> OTHER INFORMATION: Synthetic

<400> SEQUENCE: 31
agtactcaac caagtcattc tg                                                    22
```

METHODS AND COMPOSITIONS FOR THE PRODUCTION OF XYLITOL FROM XYLOSE UTILIZING DYNAMIC METABOLIC CONTROL

CROSS-REFERENCE TO RELATED APPLICATIONS

This application claims priority to U.S. Provisional Patent Application Nos. 63/004,740 filed Apr. 3, 2020, and 63/056,085 filed Jul. 24, 2020, both of which is incorporated by reference herein in its entirety.

FEDERALLY SPONSORED RESEARCH OR DEVELOPMENT

This invention was made with government support under Federal Grant No EE0007563 awarded by the Department of Energy; Federal Contract No. HR0011-14-C-0075 awarded by the United States Department of Defense; Federal Grant No. ONR YIP 12043956 awarded by the United States Department of Defense; DARPA #HR0011-14-C-0075; ONR YIP #N00014-16-1-2558; DOE EERE grant #EE0007563; N00014-16-1-2558 awarded by NAVY/ONR, and NIH Biotechnology Training Grant (T32GM008555). The government has certain rights in the invention.

FIELD OF THE INVENTION

This invention relates to metabolically engineered microorganisms, such as bacterial strains, and bioprocesses utilizing such strains. These strains provide dynamic control of metabolic pathways resulting in the production of xylitol from xylose.

SEQUENCE LISTING

The instant application contains a Sequence Listing which has been filed electronically in ASCII format as 49196-46_ST25 created Mar. 29, 2021 that is 17051 bytes in size and is hereby incorporated by reference in its entirety.

BACKGROUND OF THE INVENTION

Xylitol is an industrial sugar alcohol primarily used as a sweetener, having a similar sweetness but fewer calories than sucrose. Annual production of Xylitol is ~125.000 tons and is produced via the reduction of xylose. Xylose is the second most abundant natural sugar (after glucose), therefore it is an attractive feedstock. Many studies have demonstrated the use of xylose as a feedstock for the biosynthesis of numerous products ranging from biofuels (ethanol) to chemicals, including lactic acid, succinic acid, xylonate, 1,2,4-butanetriol, and xylitol.

The industrial production of xylitol relies on traditional chemistry, and the process has remained relatively unchanged for decades. This conversion requires expensive catalysts and requires relatively pure xylose as a feedstock. Efforts have been made to identify more economical ways to produce xylitol from lower cost, cellulosic sugar streams, including the development of biosynthetic processes. Biosynthetic production has the potential to decrease costs, utilize lower quality feedstocks, avoid the use of organic solvents, eliminate the need for expensive reduction catalysts. However, most previous biosynthetic studies producing xylitol from xylose rely on a bioconversion requiring an additional sugar (usually glucose) as an electron donor.

Oxidation of glucose (producing the byproduct gluconic acid) generates NAD (P) H which is then used for xylose reduction. While these processes offer high xylitol titers and a good yield when just considering xylose, the requirement for glucose at equimolar levels to xylose is a significant inefficiency.

Perhaps the simplest conversion is xylose to xylitol, which requires only a single enzyme, a xylose reductase. Biosynthetic production of xylitol, over chemical conversion, has the potential to decrease costs, while avoiding the use of organic solvents, eliminating the need for expensive reduction catalysts, and improving product purity.

SUMMARY OF THE INVENTION

We rationally designed genetically modified microorganism strains to optimize xylitol production from xylose utilizing two stage dynamic metabolic control. As illustrated in FIG. 1, this design included overexpression of xylose reductase and the dynamic reduction in xylose isomerase (xylA) activity to reduce xylose metabolism which competes with xylitol production. Toward this goal we constructed strains and plasmids to enable the dynamic induction of xyrA, and dynamic reduction in XylA activity upon phosphate depletion, or other causative event, either through gene silencing, proteolysis of XylA or a combination of both functions. Provided herein are microbial strains for scalable biofermentation processes the use synthetic metabolic valves (SMVs) to decouple growth from product formation. The described strains provide dynamic control of metabolic pathways, including pathways that, when altered, have negative effects on microorganism growth under certain inducible conditions.

We also fully describe improved NADPH flux coincident with xylitol biosynthesis in engineered E. coli. Xylitol is produced from xylose via an NADPH dependent reductase. We utilize two-stage dynamic metabolic control to compare two approaches to optimize xylitol biosynthesis, a stoichiometric approach, wherein competitive fluxes are decreased, and a regulatory approach wherein the levels of key regulatory metabolites are reduced. The stoichiometric and regulatory approaches lead to a 16 fold and 100 fold improvement in xylitol production, respectively. Strains with reduced levels of enoyl-ACP reductase and glucose-6-phosphate dehydrogenase, led to altered metabolite pools resulting in the activation of the membrane bound transhydrogenase and a new NADPH generation pathway, namely pyruvate ferredoxin oxidoreductase coupled with NADPH dependent ferredoxin reductase, leading to increased NADPH fluxes, despite a reduction in NADPH pools. These strains produced titers of 200 g/L of xylitol from xylose at 86% of theoretical yield in instrumented bioreactors. Dynamic control over enoyl-ACP reductase and glucose-6-phosphate dehydrogenase will broadly enable improved NADPH dependent bioconversions.

Also provided herein are multi-stage bioprocesses for xylitol production that use the described genetically modified microorganism containing one or more synthetic metabolic valves that provide dynamic flux control and result in improved xylitol production. In certain embodiments, carbon feedstocks can include xylose, or a combination of xylose and glucose, arabinose, mannose, lactose, or alternatively carbon dioxide, carbon monoxide, methane, methanol, formaldehyde, or oils. Additional genetic modifications may be added to a microorganism to provide further conversion of xylitol to additional chemical or fuel products.

Other methods, features and/or advantages is, or will become, apparent upon examination of the following Figures and detailed description. It is intended that all such additional methods, features, and advantages be included within this description and be protected by the accompanying claims.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are used, and the accompanying drawings of which:

FIG. 2A, Expression of XyrA in BL21 using media combination of SM10++ (for growth) and SM10-No phos (for expression). After the expression, the postproduction cells were lysed by freeze-thawing cycle. Next, the xyrA protein was extracted by N-N Resin because of the His-tag on XyrA which was design into plasmid sequence. FIG. 2B, Activity of xyrA with NADPH as co-factor. Reaction velocity is plotted as function of xylose concentration. In these assays, NADPH was held at a constant initial level of 50 $\mu$M. FIG. 2C. Kinetic Parameters for XyrA from this project and from other research sources as comparison.

4 proteolysis valves while the y-axis represents the different pCASCADE silencing. The DLF_25 empty valve control is in the red circle. The gray dots indicate combinations that are not assayed or have no proper cell growth for all replicates. According to the heatmap result, for the combinations which the titer/OD>3, 6 replications were performed to avoid the false positive results.

Figure 5A:
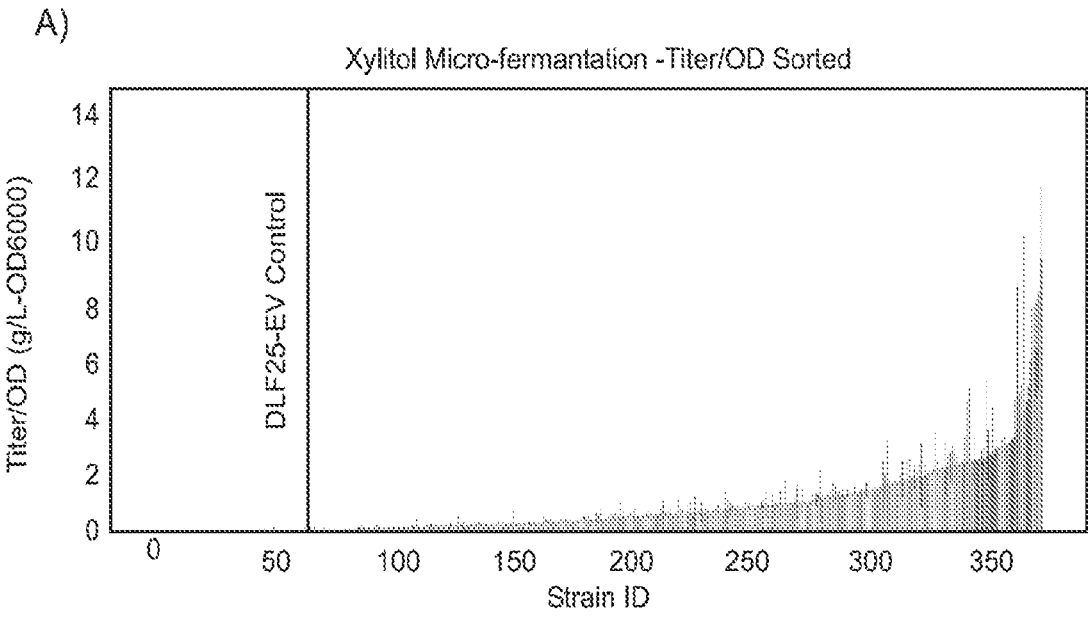
FIG. 5A-B depicts (SA) Rank order plot for average xylitol titer of all valve strains examined in 2-stage micro fermentation, as well as with standard deviation. Xylitol production in the control strain was colored in red. A post hoc Dunnett test shows combinations that differ from the DLF025-Empty vector control significantly at p<0.05, which are indicated as darkened (instead of gray bar, meaning non-significant) in the sorted titer per unit OD plot. (5B) Heatmap of xylitol titer in 2-stage production in response to different proteolysis and silencing combinations, from 0 g/L (white) to 12 g/L (darker). The x-axis stands for different
Figure 5B:
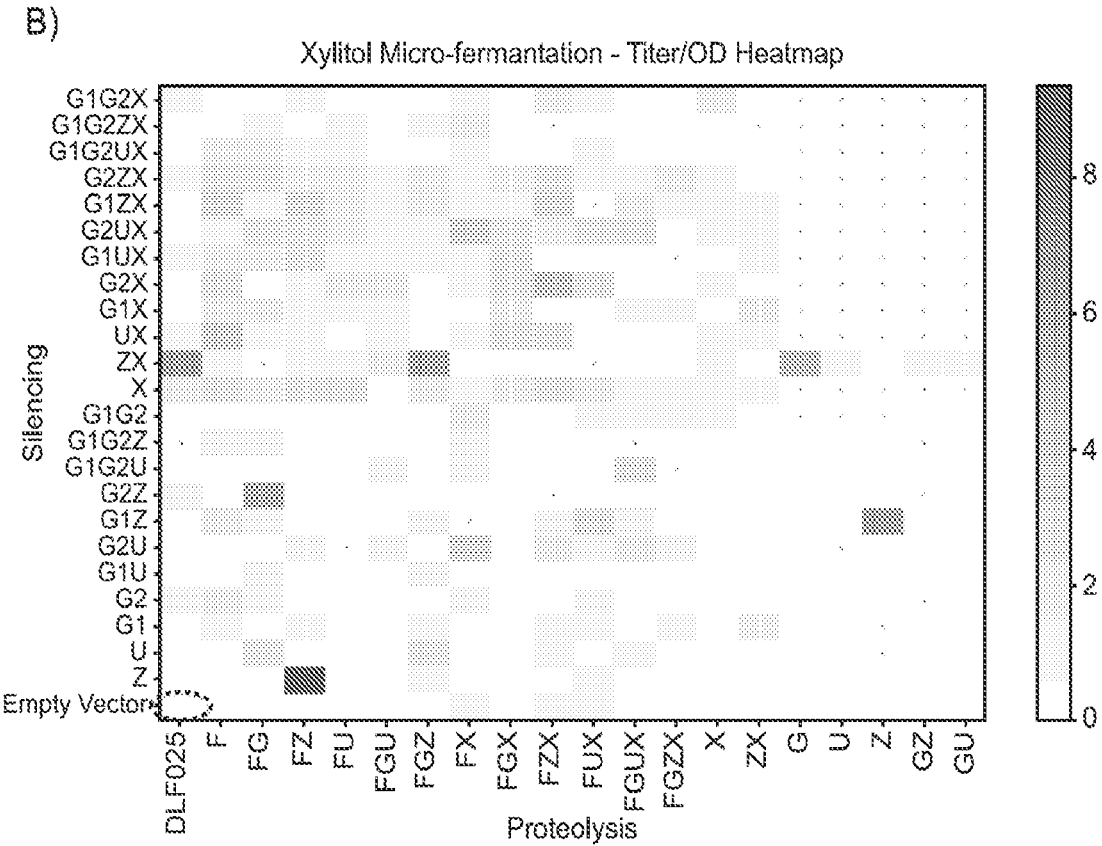
Figure 6:
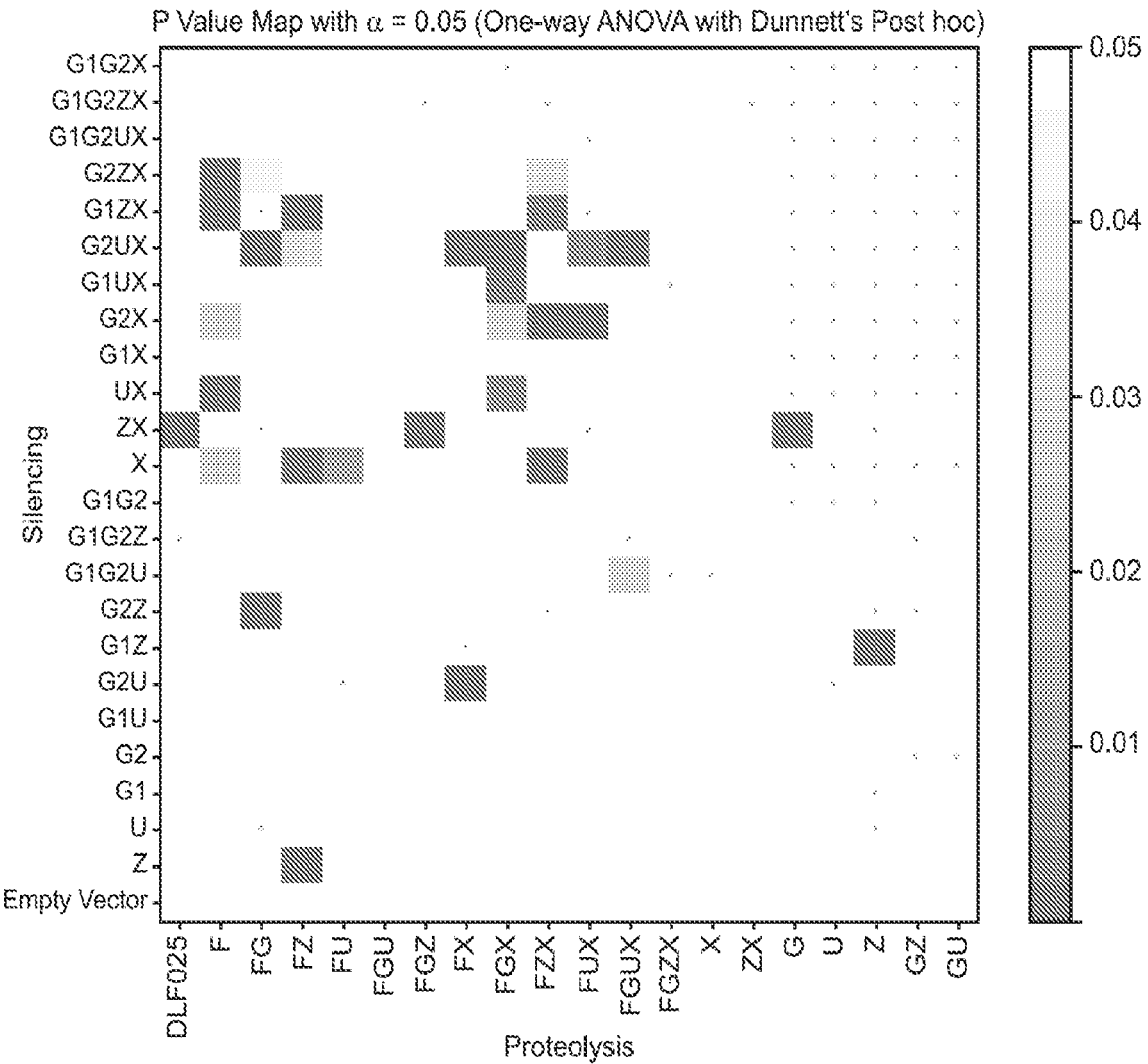

FIG. 6 depicts p-value map of micro-fermentation results of FIG. 5.

Figure 7A:
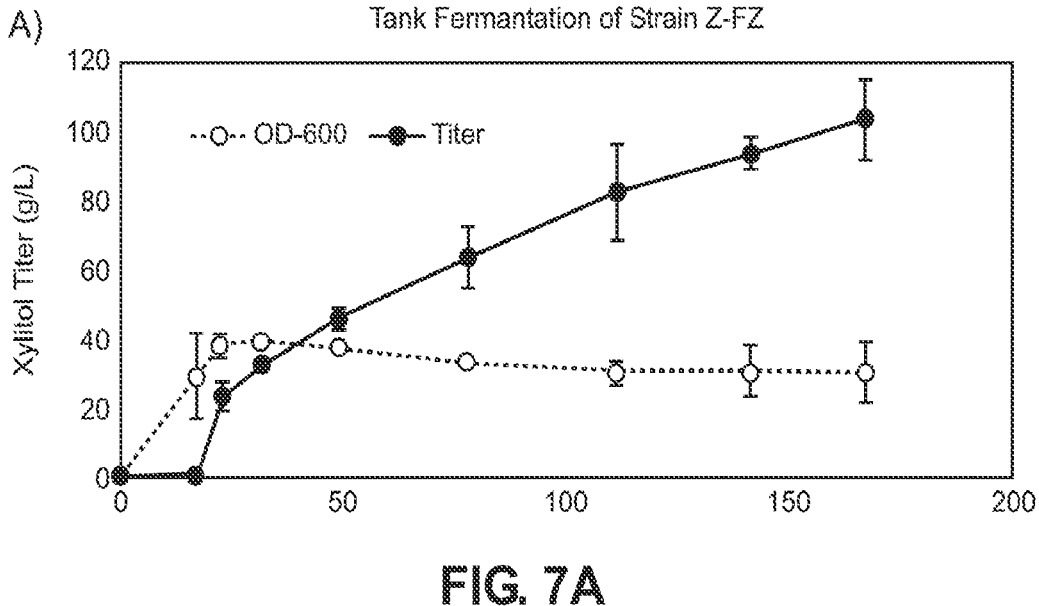
Figure 7B:
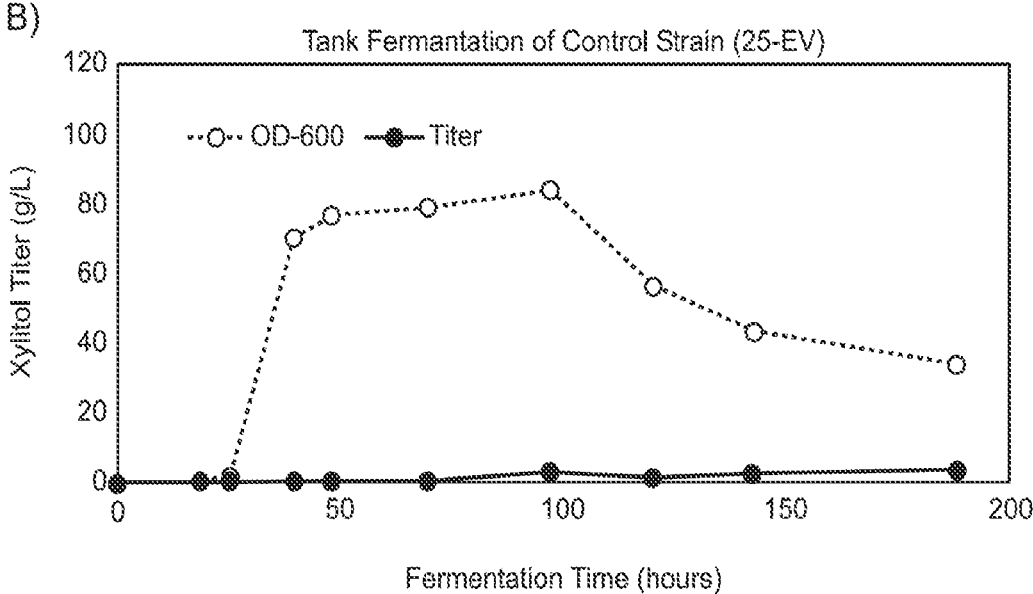

FIG. 7A-B depicts plots of instrumented fermentation of (7A) an exemplary production strain Z-FZ (Silencing of zwf ("Z"), proteolysis of fabI and zwf ("FZ")) and (7B) the control strain (DLF-0025-EV) to 1 L bioreactors. The Blue lines indicate the OD600 values and orange lines represents the xylitol titer at various time points. The Z-FZ combination resulted in a titer of 104+/−11.31 g/L after 160 hours of production, while the control strain (DLF_0025-EV) only produced-3 g/L at the same production time. We replicated the Z-FZ tank fermentation using the same seed and fermentation conditions, the results here are the average of these two replicated tanks and standard deviation was noted in the plot sample points.

Figure 8:
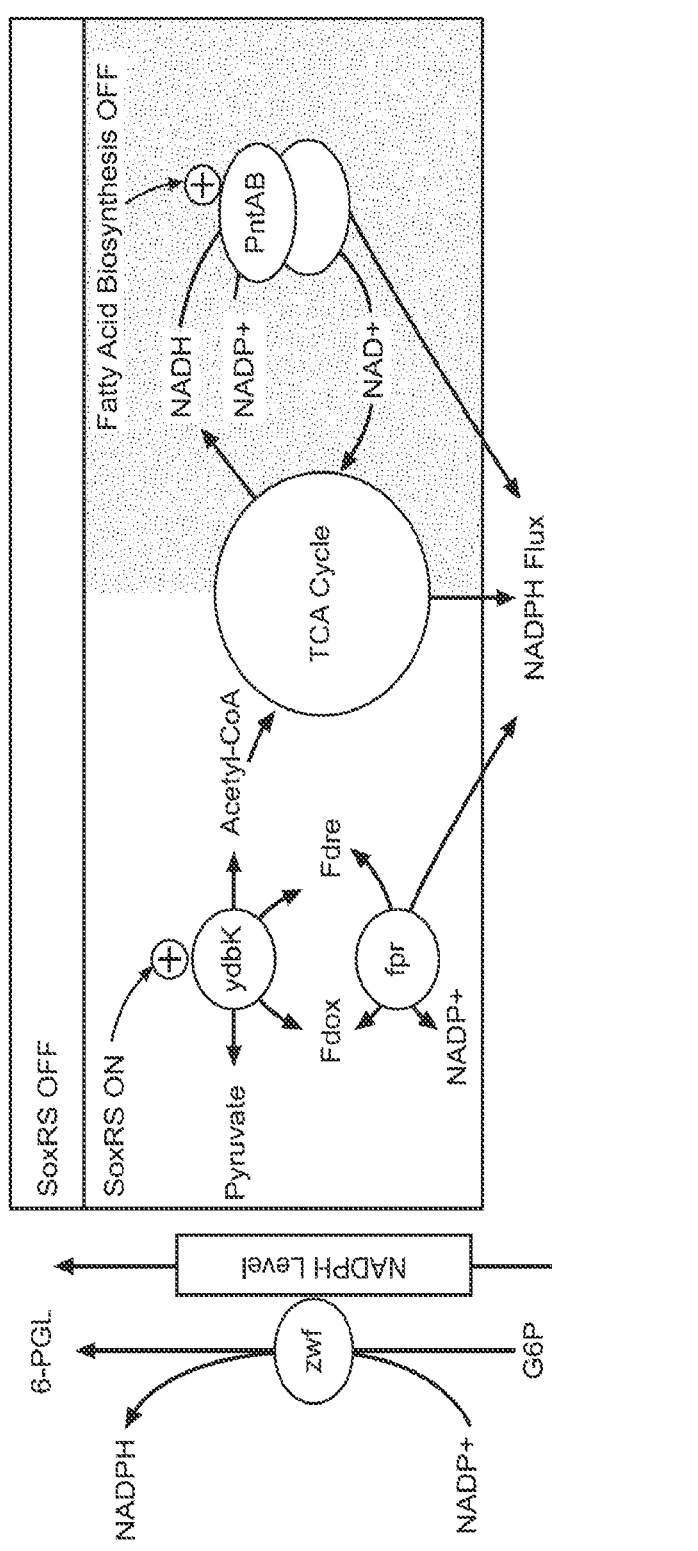

FIG. 8 depicts a conceptual model of two-stage NADPH production in our engineered system. Glucose-6-phosphate dehydrogenase (encoded by the zwf gene) is normally responsible for the biosynthesis of a majority of NADPH. This irreversible reaction drives an NADPH set point, in which the SoxRS oxidative stress response is OFF (gray area). Dynamic reduction in Zwf levels reduces NADPH pools activating the SoxRS response, which in turn activates expression of Pyruvate ferredoxin oxidoreductase (Pfo, encoded by the ydbK gene) and NADPH dependent ferredoxin reductase (Fpr). Together Pfo and Fpr (operating in reverse) constitute a new pathway to generate NADPH as well as allow for continued pyruvate oxidation and generation of acetyl-CoA for entry into the tricarboxylic acid cycle (TCA cycle). NADPH flux is further enhanced by reducing fatty acid biosynthesis whose products inhibit the membrane bound transhydrogenase (encoded by the pntAB genes). Activated PntAB uses the proton motive force to convert NADH from the TCA cycle to NADPH. NADPH can be used for bioconversions such as for xylitol production.

Figure 9A:
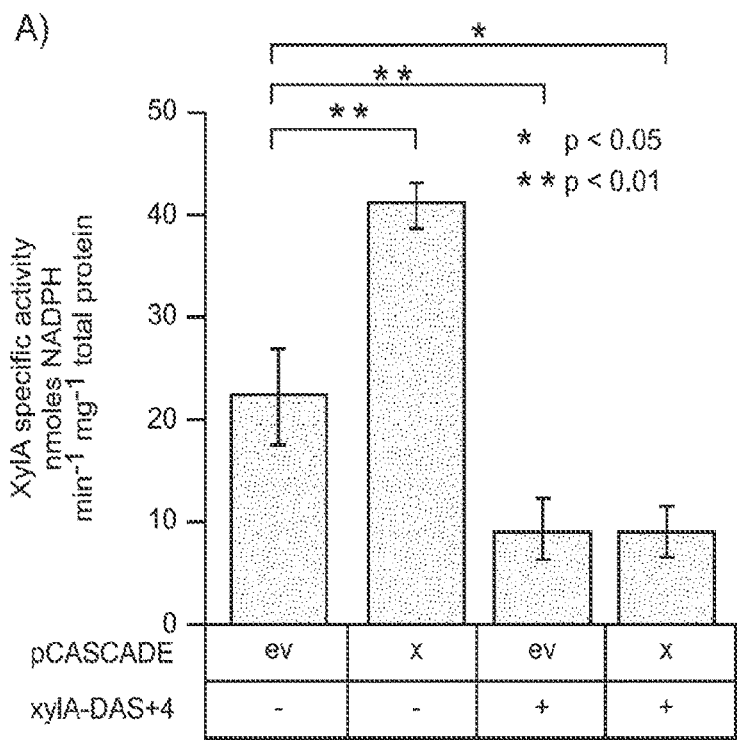
Figure 9B:
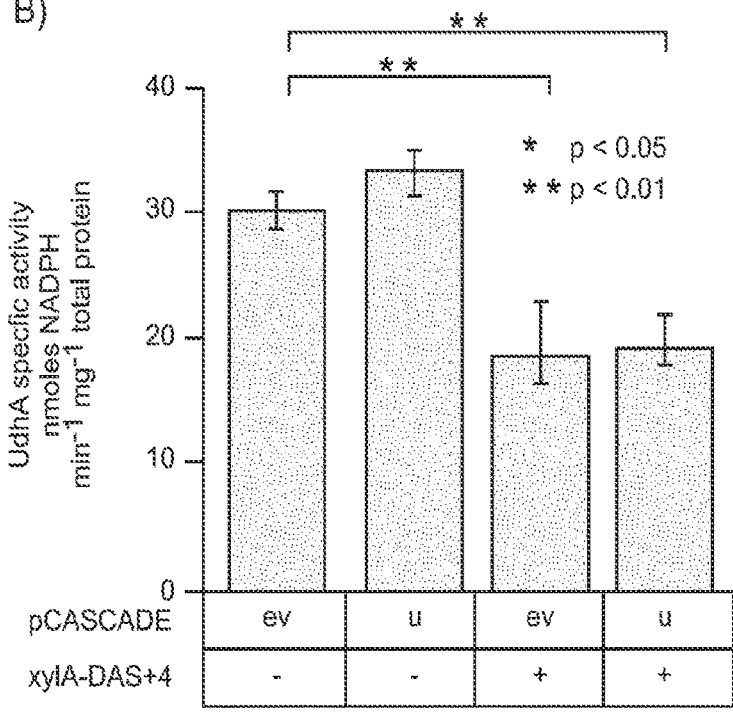

FIG. 9A-B depict enzyme levels of 9A) XylA and 9B) UdhA in response to inducible proteolysis and/or gene silencing in a phosphate depleted stationary phase, ev-empty vector, x-xylA promoter, u-udhA promoter.

FIG. 10A-C: Specific xylitol production in strains engineered for dynamic control over levels of 10A) xylose isomerase (XylA), 10B) soluble transhydrogenase (UdhA) and 10C) the combined control over xylose isomerase soluble transhydrogenase, ev-empty vector, x-xylA promoter, u-udhA promoter. All results were obtained from microfermentations.

Figure 11:
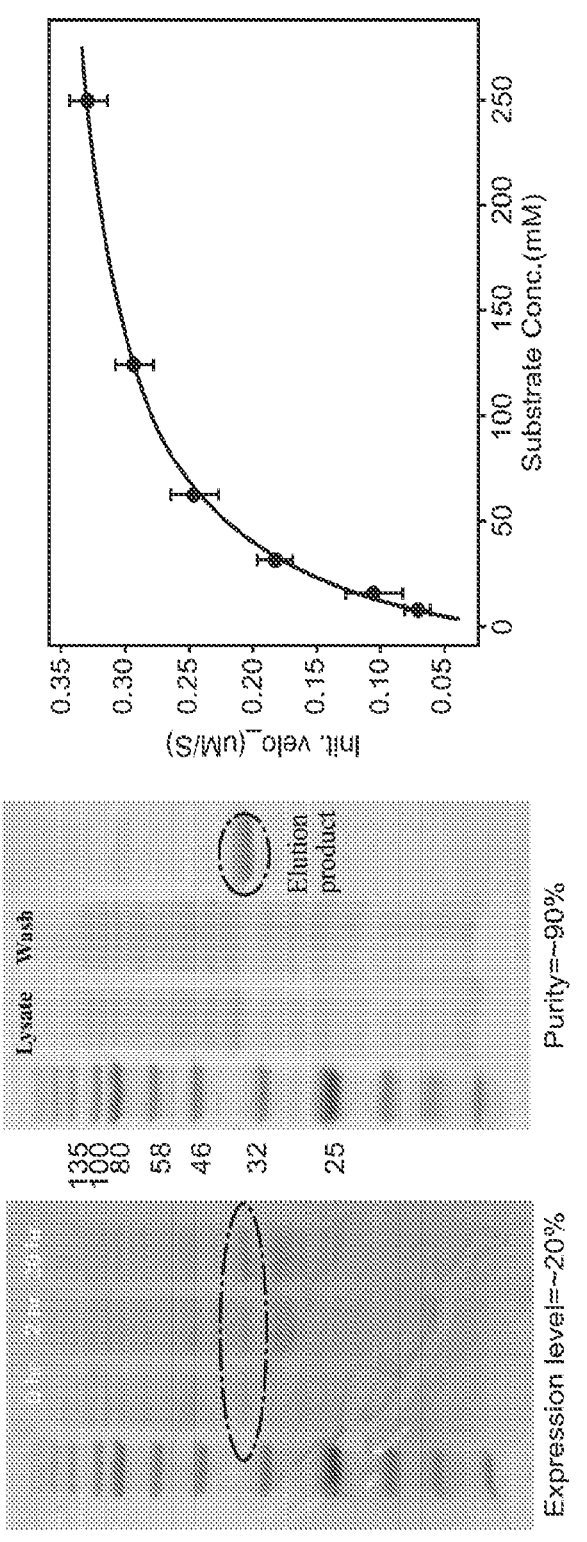
Figure 13A:
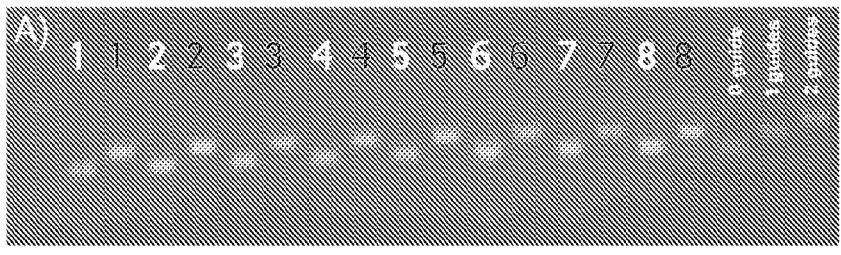
Figure 13B:
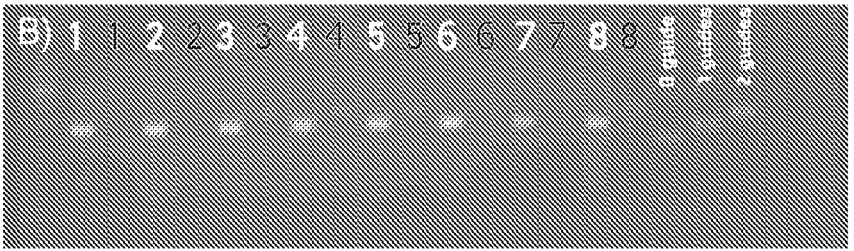
Figure 13C:
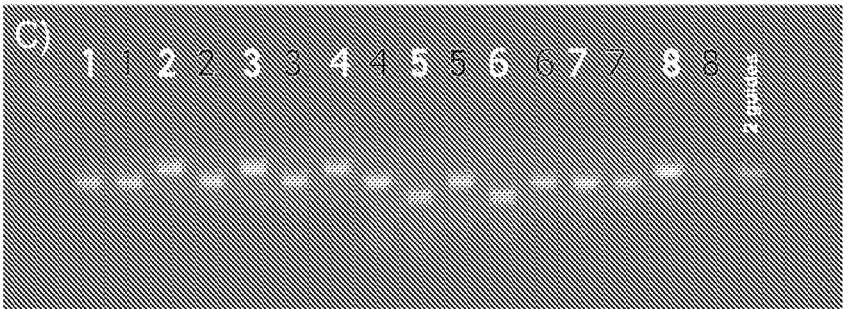
Figure 13D:
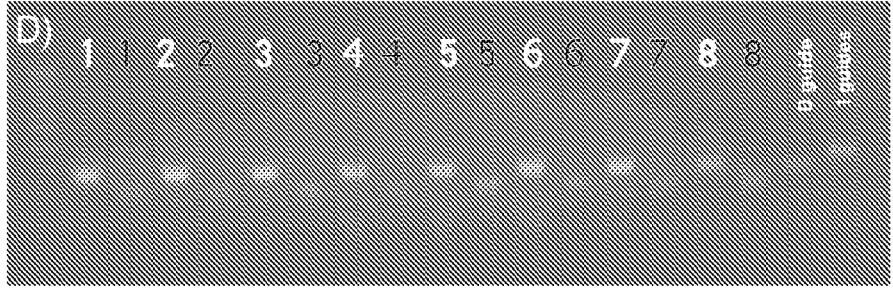

FIG. 11: XyrA expression and purification from BL21 (DE3). Left: A time course of expression post phosphate depletion, whole cell lysates demonstrate expression of XyrA. Densitometry indicates an expression level of ~20%. Middle: Purification of XyrA (which contains an N-terminal 6×histidine tag) via IMAC. Right Kinetic analysis of purified XyrA. Initial velocity ($\mu$M/s) is plotted as a function of substrate (xylose) concentration.

FIG. 12A-D: 12A) An overview of xylitol production and the location of metabolic valves in central metabolism. Xylitol is produced from xylose by a xylose reductase (xyTA). Valves comprise inducible proteolysis and/or silencing of 5 enzymes: citrate synthase (gltA), xylose isomerase (xylA), glucose-6-phosphate dehydrogenase (zwf), enoyl-ACP reductase (fabI) and soluble transhydrogenase (udhA). The membrane bound transhydrogenase (pntAB) is also shown. 12B) Specific xylitol production (g/L-OD600 nm) in microfermentations as a function of silencing and or proteolysis. 12C) P-values for the data in 12B, comparing each strain to the no-valve control using a Welchs t-test. 12D) a rank order plot of the data from panel. Bars indicate a p-value<0.05. Abbreviations: xylE:xylose permease, xylFGH:xylose ABC transporter, PPP: pentose phosphate pathway, PDH: pyruvate dehydrogenase multienzyme complex, TCA: tricarboxylic acid, G6P: glucose-6-phosphate, 6-PGL: 6-phosphogluconolactone, 6PG: 6-phosphogluconate, GA3P: glyceraldehyde-3-phosphate, PEP: phosphoenolpyrvate, OAA: oxaloacetic acid, X5P: xylulose-5-phosphate, Fd: ferredoxin, Silencing: ev: empty vector, g2: gltAp2 promoter, z: zwf promoter, x: xylA promoter, u: udhA promoter, Proteolysis: F: fabI-DAS+4, G: gltA-DAS+4, Z: zwf-DAS+4, U: udha_DAS+4, X: xylA-DAS+4. All results were obtained from microfermentations.

FIG. 13A-D: Agarose gel electrophoretic analysis of gRNA array stability. Colony PCR was used to amplify and size gRNA arrays from 8 clones after transformation into host strains engineered for dynamic metabolic control. "Guide" indicates PCR products are taken from sequence confirmed gRNA arrays with 0, 1, or 2 gRNAs respectively. 13A) Strain DLF_Z0025, white labels: pCASCADE-ev, yellow labels: pCASCADE-g2, 13B) Strain DLF_Z0025, white labels: pCASCADE-z, yellow labels: pCASCADE-fg2, 13C) White labels: Strain DLF_Z0044, pCASCADE-fg2, yellow labels: DLF_Z0025, pCASCADE-fg2, 13D) White labels: Strain DLF_Z0046, pCASCADE-g2, gray labels: DLF_Z1002 pCASCADE-fg2.

Figure 14:
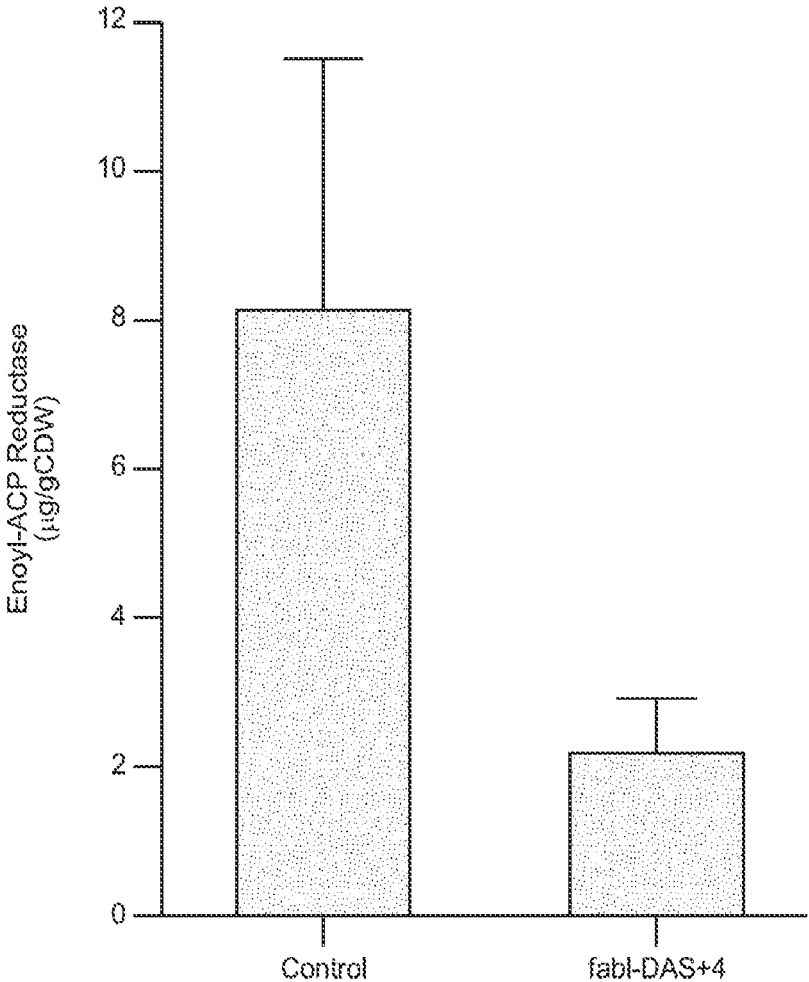

FIG. 14: Dynamic Control over FabI (enoyl-ACP reductase) levels due to inducible proteolysis with a DAS+4 degron tag. The chromosomal fabI gene was tagged with a C-terminal sfGFP. Protein levels were measured by ELISA, 24 hour post induction by phosphate depletion in microfermentations.

FIG. 15A-D: Identification of pathways responsible for NADPH and xylitol production in the "FZ" valve strain 15A) the impact of deletions of ydbK and fpr on specific xylitol production, 15B) the impact of pntAB overexpression on xylitol production. (15C-D) "FZ" valve strains further modified for dynamic control over 15C) GltA levels and 15D) UdhA levels, ev-empty vector, z-zwf promoter, g2-gltAp2 promoter, u-udhA promoter. All results were obtained from microfermentations.

Figures 16A, 16B:
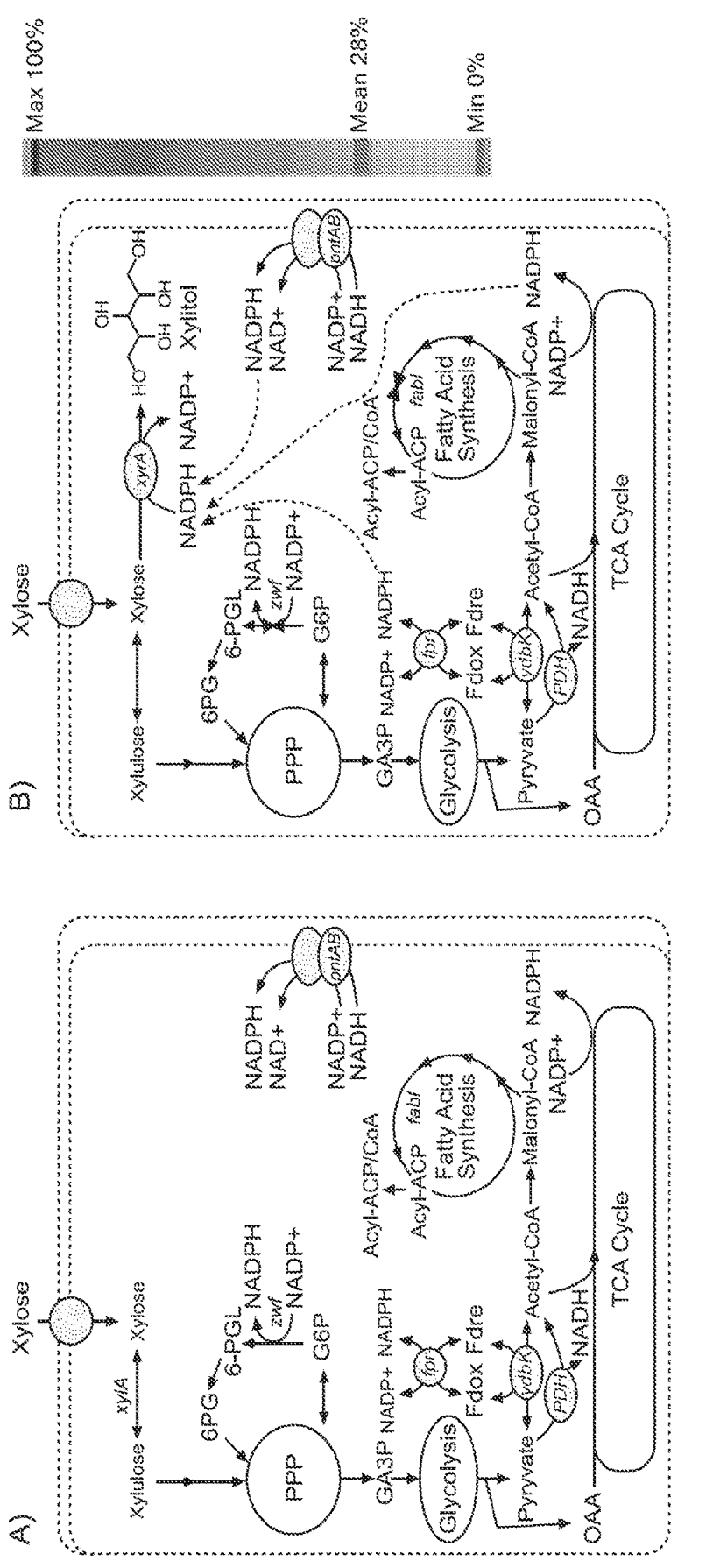

FIG. 16A-B: Stoichiometric flux models of 16A) cellular growth and 16B) stationary phase xylitol production in "FZ" valve strains. Pathway flux is relative to xylose uptake rates. During growth the majority of flux is through the pentose phosphate pathway (PPP), pyruvate dehydrogenase multienzyme complex (PDH) with minimal flux through the pentose membrane bound transhydrogenase. Upon dynamic control, a 4-fold increase in membrane bound transhydrogenase flux is accompanied by increased flux through Pfo (ydbK) and FPr. Abbreviations: G6P: glucose-6-phosphate, 6-PGL: 6-phosphogluconolactone, 6PG: 6-phosphogluconate, GA3P: glyceraldehyde-3-phosphate, OAA: oxaloacetic acid.

Figure 17A:
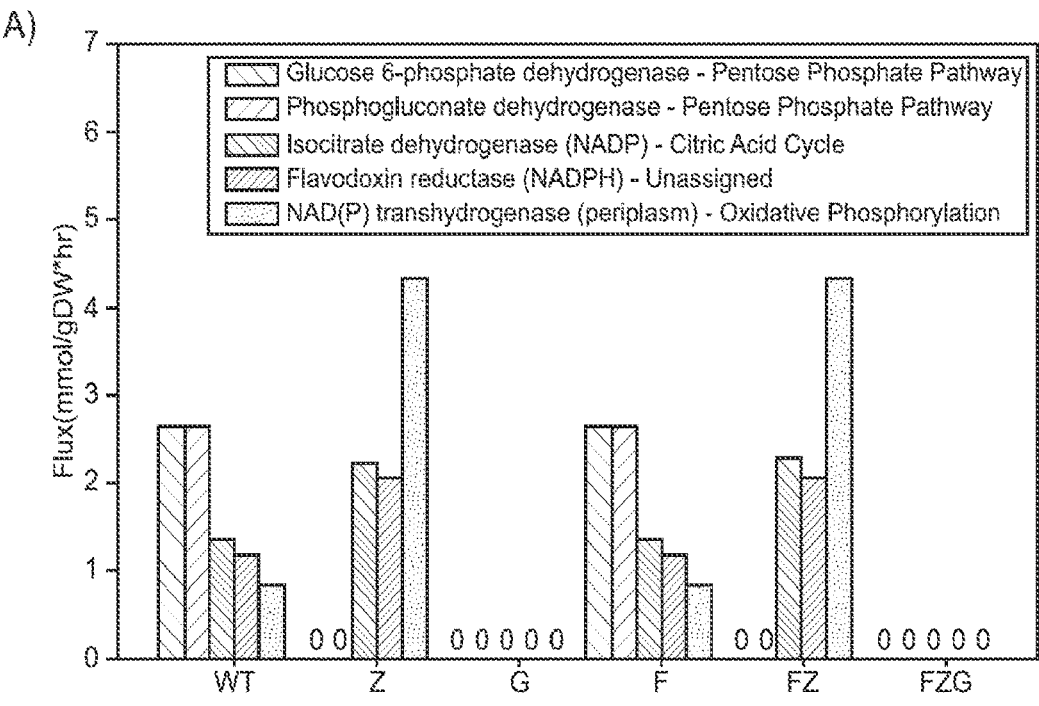
Figure 17B:
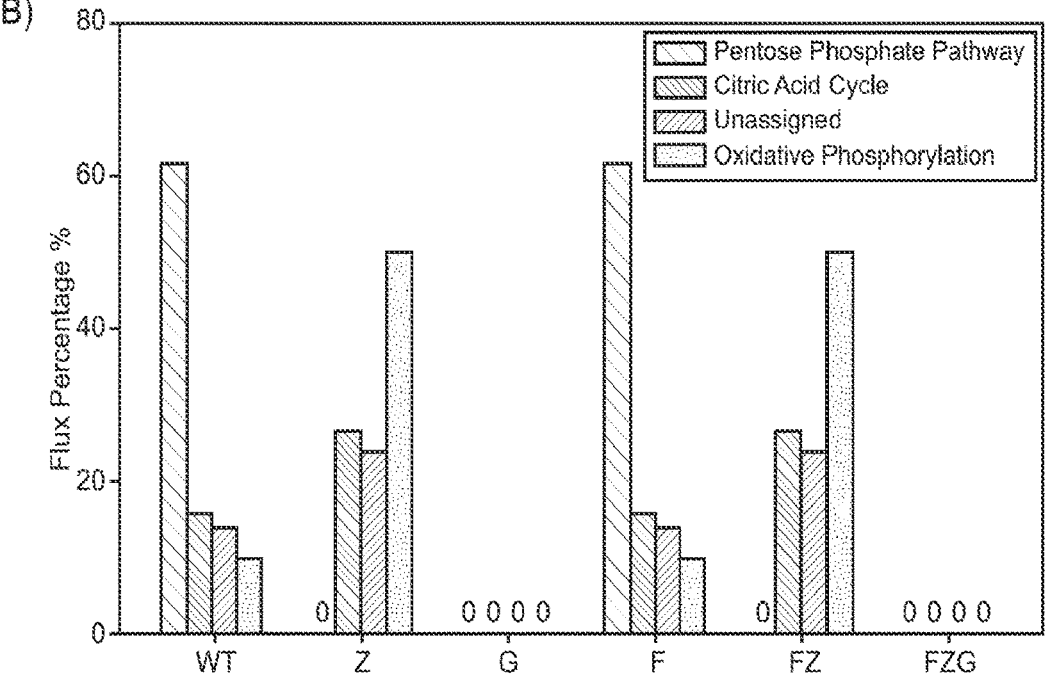

FIG. 17A-B Modeled NADPH producing reactions and pathways for xylitol production in different production strains. 17A) Specific reactions fluxes during xylitol production. 17B) Pathway percentage fluxes for xylitol production.

Figure 18A:
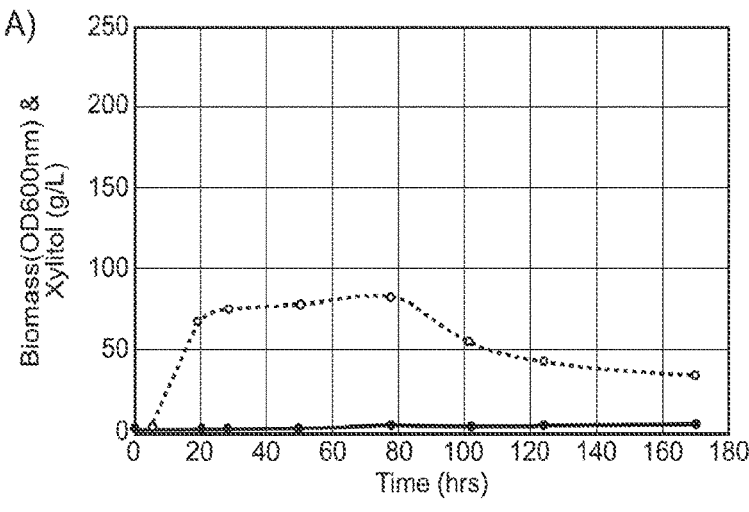
Figure 18B:
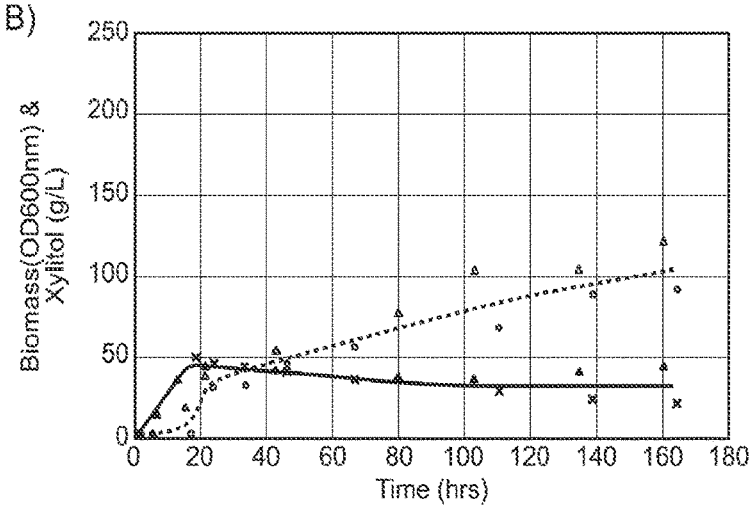
Figure 18C:
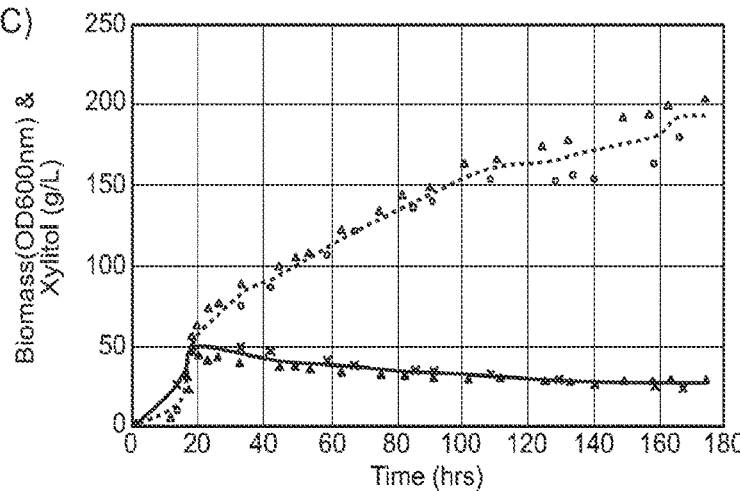

FIG. 18A-C: Xylitol production in minimal media fed batch fermentations in instrumented bioreactors by 18A) the control strain expressing xylose reductase (DLF_Z0025, pCASCADE-ev, pHCKan-xyrA), 18B) the "FZ" valve strain (DLF_Z0025-fabI-DAS+4-zwf-DAS+4, pCASCADE-z, pHCKan-xyrA), 18C) the "FZ" valve strain also overexpressing the membrane bound transhydrogenase pntAB (DLF_Z0025-fabI-DAS+4-zwf-DAS+4, pCASCADE-z, pHCKan-xyrA, pCDF-pntAB). Biomass (black) and xylitol (blue) are given as a function of time. For FIGS. 18B and 18C, x's and triangles represent the measured values of two duplicate runs.

Figure 19:
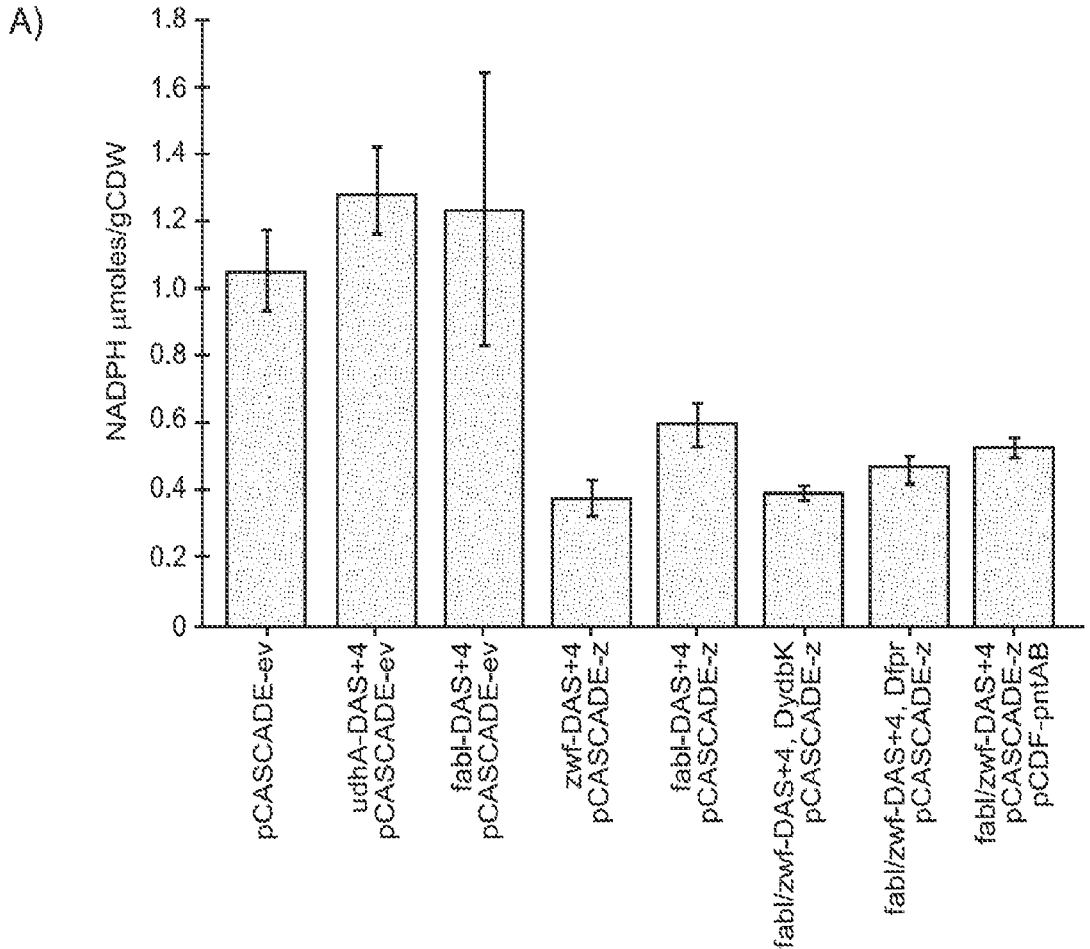

FIG. 19 depicts stationary phase NADPH pools in engineered strain. Pools were measured 24 hours post phosphate depletion.

DETAILED DESCRIPTION OF THE INVENTION

The present invention is related to various genetically modified microorganisms that have utility for production of xylitol or a related chemical products to methods of making such chemical products using these microorganisms.

Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms, and the like.

The term "heterologous DNA." "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression. The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome). As used herein, chromosomal, and native and endogenous refer to genetic material of the host microorganism.

The term "synthetic metabolic valve," and the like as used herein refers to either the use of controlled proteolysis, gene silencing or the combination of both proteolysis and gene silencing to alter metabolic fluxes.

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production, Micro-fermentation (microfermentation) or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a UniProt identification number, which would be well known to one skilled in the art. The UniProt database can be accessed at UniProt.org. When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, DCW means dry cell weight. "s" means second(s), "min" means minute(s), "h," "hr," or "hrs" means hour(s), "psi" means pounds per square inch, "nm" means nanometers, "d" means day(s), "μL" or "uL" or "ul" means microliter(s), "mL" means milliliter(s), "L" means liter(s), "mm" means millimeter(s), "nm" means nanometers, "mM" means millimolar. "μM" or "UM" means micromolar, "M" means molar, "mmol" means millimole(s), "μmol" or "uMol" means micromole(s)", "g" means gram(s), "μg" or "ug" means microgram(s) and "ng" means nanogram(s), "PCR" means polymerase chain reaction, "OD" means optical density, "OD$_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-μ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

I. Carbon Sources

Bio-production media, which is used in the present invention with recombinant microorganisms must contain suitable carbon sources or substrates for both growth and production stages. Suitable substrates may include but are not limited to xylose or a combination of xylose and glucose, sucrose, xylose, mannose, arabinose, oils, carbon dioxide, carbon monoxide, methane, methanol, formaldehyde, or glycerol. It is contemplated that all of the above mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

More particularly, based on the various criteria described herein, suitable microbial hosts for the bio-production of a chemical product generally may include, but are not limited to the organisms described in the Methods Section.

The host microorganism or the source microorganism for any gene or protein described here may be selected from the following list of microorganisms: *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces*, and *Pseudomonas*. In some aspects the host microorganism is an *E. coli* microorganism.

III. Media and Culture Conditions

In addition to an appropriate carbon source, such as selected from one of the herein-disclosed types, bio-production media must contain suitable minerals, salts, cofactors, buffers and other components, known to those skilled in the art, suitable for the growth of the cultures and promotion of chemical product bio-production under the present invention.

Another aspect of the invention regards media and culture conditions that comprise genetically modified microorganisms of the invention and optionally supplements.

Typically cells are grown at a temperature in the range of about 25° C., to about 40° C., in an appropriate medium, as well as up to 70° C., for thermophilic microorganisms. Suitable growth media are well characterized and known in the art. Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges. Bio-productions may be performed under aerobic, microaerobic or anaerobic conditions with or without agitation.

IV. Bio-Production Reactors and Systems

Fermentation systems utilizing methods and/or compositions according to the invention are also within the scope of the invention. Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications. Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as E. coli, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may include a manipulation directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected culture conditions. Genetic manipulation of nucleic acid sequences may increase copy number and/or comprise use of mutants of an enzyme related to product production. Specific methodologies and approaches to achieve such genetic modification are well known to one skilled in the art.

In various embodiments, to function more efficiently, a microorganism may comprise one or more gene deletions. For example, in E. coli, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in E. coli may be designed as synthetic metabolic valves to alter metabolism and improve product formation. Representative genes in E. coli may include but are not limited to the following: fabI, zwf, gltA, ppe, udhA, lpd, sucD, aceA, pfkA, lon, rpoS, pykA, pykF, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various embodiments genetic modifications, including synthetic metabolic valves also are provided to increase the pool and availability of the cofactor NADPH and/or NADH which may be consumed in the production of a product.

VI. Synthetic Metabolic Valves

Use of synthetic metabolic valves allows for simpler models of metabolic fluxes and physiological demands during a production phase, turning a growing cell into a stationary phase biocatalyst. These synthetic metabolic valves can be used to turn off essential genes and redirect carbon, electrons, and energy flux to product formation in a multi-stage fermentation process. One or more of the following provides the described synthetic valves: 1) transcriptional gene silencing or repression technologies in combination with 2) inducible and selective enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In particular, the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis.

VI.A Gene Silencing

In particular, the invention describes the use of controlled gene silencing to provide the control over metabolic fluxes in controlled multi-stage fermentation processes. There are several methodologies known in the art for controlled gene silencing, including but not limited to mRNA silencing or RNA interference, silencing via transcriptional repressors and CRISPR interference Methodologies and mechanisms for RNA interference are taught by Agrawal et al. "RNA Interference: Biology, Mechanism, and Applications" Microbiology and Molecular Biology Reviews, December 2003; 67(4) p 657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152(5) p 1173-1183. DOI: 10.1016/j.cell.2013.02.022. In addition, methodologies, and mechanisms for CRISRPR interference using the native E. coli CASCADE system are taught by Luo et al. "Repurposing endogenous type I CRISPR-Cas systems for programmable gene repression" NAR. October 2014; DOI; 10.1093. In additional numerous transcriptional repressor systems are well known in the art and can be used to turn off gene expression.

VI.B Controlled Proteolysis

In particular, the invention describes the use of controlled protein degradation or proteolysis to provide the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the E. coli clpXP protease for controlled protein degradation are taught by McGinness et al, "Engineering controllable protein degradation", Mol Cell. June 2006; 22(5) p 701-707. This methodology relies upon adding a specific C-terminal peptide tag such as a DAS4 (or DAS+4) tag. Proteins with this tag are not degraded by the clpXP protease until the specificity enhancing chaperone sspB is expressed sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments, the cleavage can be expected lead to protein inactivation or degradation. For example Schmidt et al ("ClpS is the recognition component for Escherichia coli substrates of the N-end rule degradation pathway" Molecular Microbiology March 2009, 72(2), 506-517, doi:10.1111), teaches that an N-terminal sequence can be added to a protein of interest in providing clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to provide the control over metabolic fluxes in controlled multi-stage fermentation processes, in E. coli. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example Grilly et al, "A synthetic gene network for tuning protein degradation in Saccharomyces cerevisiae" Molecular Systems Biology 3, Article 127, doi: 10.1038, teaches the expression and use of the E. coli clpXP protease in the yeast Saccharomyces cerevisiae. Such approaches can be used to transfer the methodology for synthetic metabolic valves to any genetically tractable host.

VI.C Synthetic Metabolic Valve Control

In particular the invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well-known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur, and magnesium. Natural gene expression systems that respond to these nutrient limitations can be used to operably link the control of gene expression silencing and/or controlled proteolysis to the transition between growth and production phases in multi-stage fermentation processes.

Within the scope of the invention are genetically modified microorganism, wherein the microorganism is capable of producing xylitol at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr. greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

Within the scope of the invention are genetically modified microorganism, wherein the microorganism is capable of producing xylitol from xylose or another sugar source at a yield greater than 0.5 g product/g xylose, greater than 0.6 g product/g xylose, greater than 0.7 g product/g xylose, greater than 0.8 g product/g xylose, greater than 0.9 g product/g xylose, greater than 0.95 g product/g xylose, or greater than 0.98 g product/g xylose.

In various embodiments, the invention includes a culture system comprising a carbon source in an aqueous medium and a genetically modified microorganism according to any one of claims herein, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10.000 L, greater than 50.000 L, greater than 100,000 L or greater than 200,000 L, and such as when the volume of the aqueous medium is greater than 250 L and contained within a steel vessel.

Overview of Invention Aspects

In one aspect, a genetically modified microorganism for producing xylitol comprising is provided. The genetically modified microorganism characterized by inducible modification of expression of xylose reductase (xyrA) and an inducible synthetic metabolic valve. The synthetic metabolic valve characterized by a gene expression-silencing synthetic metabolic valve characterized by silencing gene expression of one or more genes encoding one or more enzymes; or an enzymatic degradation synthetic metabolic valve characterized by inducing enzymatic degradation of one or more enzymes, or a combination thereof.

In one aspect the xylose reductase of the genetically modified microorganism is an NADPH dependent xylose reductase or the xylose reductase maybe the xyrA gene of *A. niger.*

In one aspect, the genetically modified microorganism produces xylitol from a xylose feedstock. Of course the genetically modified microorganism may use a feedstock comprising xylose and a second sugar blending in any ratio.

In one aspect the gene-silencing synthetic metabolic valve or the enzyme degradation synthetic metabolic valve of the genetically modified microorganism maybe directed to control of the gene encoding xylose isomerase or the xylose isomerase enzyme; or the gene encoding glucose-6-phosphate dehydrogenase (zwf) or the glucose-6-phosphate dehydrogenase (zwf) enzyme.

In one aspect the gene-silencing synthetic metabolic valve or the enzyme degradation synthetic metabolic valve of the genetically modified microorganism maybe directed to control more than one gene, for example a gene encoding glucose-6-phosphate dehydrogenase (zwf) or the glucose-6-phosphate dehydrogenase (zwf) enzyme; and a gene encoding xylose isomerase or the xylose isomerase enzyme.

In yet another aspect, In one aspect the gene-silencing synthetic metabolic valve or the enzyme degradation synthetic metabolic valve of the genetically modified microorganism maybe directed to control more than one gene, for example a gene encoding glucose-6-phosphate dehydrogenase (zwf) or the glucose-6-phosphate dehydrogenase (zwf) enzyme; and a gene encoding enoyl-ACP reductase (fabI) or the enoyl-ACP reductase (fabI) enzyme.

In yet another aspect. In one aspect the gene-silencing synthetic metabolic valve or the enzyme degradation synthetic metabolic valve of the genetically modified microorganism may be directed to control silencing of a gene encoding glucose-6-phosphate dehydrogenase (zwf) and enzyme degradation of glucose-6-phosphate dehydrogenase (zwf) enzyme; and enoyl-ACP reductase (fabI) enzyme.

In another aspect, expression of xylose reductase, gene expression-silencing synthetic metabolic valve, and the enzymatic degradation synthetic metabolic valve are induced under conditions of a transition phrase of a multi-stage biofermentation process. The induction may occur via nutrient depletion or via phosphate depletion.

In one aspect, the genetically modified microorganism may further comprise a chromosomal deletion.

In one aspect, the silencing of gene expression comprises CRISPR interference and the genetically modified microorganism also expresses a CASCADE guide array, the array comprising two or more genes encoding small guide RNAs each specific for targeting a different gene for simultaneous silencing of multiple genes.

In one aspect, the genetically modified microorganism produces a xylitol product titer of greater than 0.08 g/L at twenty four in a biofermentation process.

In one aspect, the invention provides for a multi-stage fermentation bioprocess for producing xylitol from a genetically modified microorganism, including the steps of (a) providing a genetically modified microorganism. The genetically modified microorganism characterized by a modification of expression of xylose reductase and a synthetic metabolic valve comprising: a gene expression-silencing synthetic metabolic valve characterized by silencing gene expression of one or more genes encoding one or more enzymes: or an enzymatic degradation synthetic metabolic valve characterized by inducing enzymatic degradation of one or more enzymes, or a combination thereof. The one or more enzymes of each synthetic metabolic valve are the same or different. The method further includes the steps of growing the genetically modified microorganism in a media with a xylose feedstock and transitioning from a growth phase to a xylitol. The transition step includes inducing the synthetic metabolic valve(s) to slow or stop the growth of the microorganism; and inducing expression of xylose reductase, thereby producing xylitol.

In some aspects, the multi-stage fermentation bioprocess may use a genetically modified microorganism characterized by the gene-silencing synthetic metabolic valve or the enzyme degradation synthetic metabolic valve of the genetically modified microorganism are directed to control of at least two genes, including a gene encoding glucose-6-phosphate dehydrogenase (zwf) or the glucose-6-phosphate dehydrogenase (zwf) enzyme; and a gene encoding enoyl-ACP reductase (fabI) or the enoyl-ACP reductase (fabI) enzyme.

In some aspects, the multi-stage fermentation bioprocess will produce a xylitol product titer of greater than 0.08 g/L at twenty four in a biofermentation process.

In some aspects, the transition phase of the multi-stage fermentation bioprocess occurs via phosphate depletion of the growth media. In some aspects, the genetically modified microorganism of the multi-stage fermentation bioprocess is further characterized by a chromosomal deletion.

In one aspect the genetically modified microorganism for producing xylitol, the microorganism comprises: inducible reduction of xylose isomerase: inducible reduction of glucose-6-phosphate dehydrogenase activity so that the microorganism produces xylitol from the feedstock xylose upon induction. In another aspect the microorganism is an *E. coli* microorganism. In one aspect, the induction of the microorganism occurs by via nutrient depletion. In one aspect, the induction of the microorganism occurs via phosphate depletion.

In one aspect, the invention provides a multi-stage fermentation bioprocess for producing xylitol from a genetically modified microorganism including inducible reduction of xylose isomerase and inducible reduction of glucose-6-phosphate dehydrogenase activity. The bioprocess includes the steps of (a) providing a genetically modified microorganism, (b) growing the genetically modified microorganism in a media with a xylose feedstock: (c) transitioning from a growth phase to a xylitol producing stage by inducing the synthetic metabolic valve(s) to slow or stop the growth of the microorganism; and inducing expression of xylose isomerase, thereby (d) producing xylitol.

In one aspect the genetically modified microorganism for producing xylitol, the microorganism comprises: inducible reduction of xylose reductase: inducible reduction of glucose-6-phosphate dehydrogenase activity; inducible reduction of enoyl-ACP reductase; wherein the strain produces xylitol from the feedstock xylose upon induction. In one aspect, the microorganism is an *E. coli* microorganism. In some aspect, induction of the microorganism occurs by via nutrient depletion or phosphate depletion.

In one aspect, the invention provides a multi-stage fermentation bioprocess for producing xylitol from a genetically modified microorganism including inducible reduction of xylose reductase: inducible reduction of glucose-6-phosphate dehydrogenase activity: inducible reduction of enoyl-ACP reductase. The bioprocess includes the steps of (a) providing a genetically modified microorganism: (b) growing the genetically modified microorganism in a media with a xylose feedstock: (c) transitioning from a growth phase to a xylitol producing stage by inducing the synthetic metabolic valve(s) to slow or stop the growth of the microorganism; and inducing expression of xylose reductase, thereby (d) producing xylitol.

In one aspect the genetically modified microorganism for producing xylitol, the microorganism comprises: activity of a membrane bound transhydrogenase activity is increased; activity of a pyruvate ferredoxin oxidoreductase is increased: activity of a NADPH dependent ferredoxin reductase is increased; and wherein the microorganism produces at least one chemical product whose biosynthesis requires NADPH.

Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a FIGS. 1 and 4), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all subranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. See, e.g., Sambrook and Russell. "Molecular Cloning: A Laboratory Manual," Third Edition 2001 (volumes 1-3), Cold Spring Harbor Laboratory Press, Cold Spring Harbor, N.Y.; Animal Cell Culture. R. I. Freshney, ed., 1986. These published resources are incorporated by reference herein.

The following published resources are incorporated by reference herein for description useful in conjunction with the invention described herein, for example, methods of industrial bio-production of chemical product(s) from sugar sources, and also industrial systems that may be used to achieve such conversion (Biochemical Engineering Fundamentals, $2^{nd}$ Ed. J. E Bailey and D. F. Ollis, McGraw Hill. New York, 1986, e.g. Chapter 9, pages 533-657 for biological reactor design; Unit Operations of Chemical Engineering, $5^{th}$ Ed., W. L. McCabe et al., McGraw Hill, New York 1993, e.g., for process and separation technologies analyses; Equilibrium Staged Separations, P. C. Wankat. Prentice Hall. Englewood Cliffs, NJ USA, 1988, e.g., for separation technologies teachings).

All publications, patents, and patent applications mentioned in this specification are entirely incorporated by reference herein, including U.S. Provisional Application No. 62/010,574, filed Jun. 11, 2014, and 62/461,436, filed Feb. 21, 2017, and PCT/US2015/035306 filed Jun. 11, 2015 and PCT/US2018/019040, filed Feb. 21, 2018.

EXAMPLES

The examples herein provide some examples, not meant to be limiting. All reagents, unless otherwise indicated, are obtained commercially. Species and other phylogenic identifications are according to the classification known to a person skilled in the art of microbiology, molecular biology, and biochemistry.

Common Methods

Reagents and Media

All reagents and chemicals were obtained from Sigma Aldrich (St. Louis, MO) unless otherwise noted. MOPS (3-(N-morpholino) propanesulfonic acid) was obtained from BioBasic, Inc. (Amherst. NY). Crystalline xylose was obtained from Profood International (Naperville, IL). All media: SM10++, SM10 No Phosphate, and FGM25 were prepared as previously reported (Menacho-Melgar. R, et al. Scalable, two-stage, autoinduction of recombinant protein expression in *E. coli* utilizing phosphate depletion. *Biotechnol. Bioeng.* 26, 44 (2020)) except that xylose was substituted for glucose (1 gram xylose for 1 gram glucose) in all media formulations. LB. Lennox formulation, was used for routine strain propagation. Working antibiotic concentrations were as follows: kanamycin: 35 μg/mL, chloramphenicol: 35 μg/mL, gentamicin: 10 μg/mL, 10 zeocin: 100 μg/mL, blasticidin: 100 μg/mL, spectinomycin: 25 μg/ml, tetracycline: 5 μg/mL.

Strains & Plasmids Construction

Refer to Supplemental Table S1 for a list of strains and plasmids used in this study. Sequences of synthetic DNA used in this study are given in Supplemental Table S2. Chromosomal modifications were constructed using standard recombineering methodologies (Liochev, S. I. et al *Proc. Natl. Acad. Sci. U.S.A* 91, 1328-1331(1994)). The recombineering plasmid pSIM5 was a kind gift from Donald Court (NCI, redrecombineering.nciforf.gov/court-lab. 53.54 C-terminal DAS+4 tags were added by direct integration and selected through integration of antibiotic resistance cassettes 3' of the gene as previously described.24 All strains were confirmed by PCR, agarose gel electrophoresis and confirmed by sequencing. Refer to Table S3 for oligos used for strain confirmation and sequencing.

The xyrA gene from *Aspergillus niger* was codon optimized for expression in *E. coli* and the plasmid, pHCKan-xyrA (Addgene #58613), enabling the low phosphate induction of xylose reductase, was constructed by TWIST Biosciences (San Francisco, CA), pCDF-pntAB (Addgene #158609) was constructed using PCR and Gibson Assembly from pCDF-ev 30 to drive expression of the pntAB operon from the low phosphate inducible ugpBp promoter (Moreb, E. A, et al. Media Robustness and scalability of phosphate regulated promoters useful for two-stage autoinduction in *E. coli. ACS Synthetic Biology* (2020) doi:10.1021/acssynbio.0c00182), pCASCADE guide RNA array plasmids were prepared by the combination of PCR and Gibson assembly as previously described. Refer to Table S4 for oligos used for pCASCADE plasmid construction.

TABLE 1

Plasmids used in these Examples:

| Plasmids | Promoter | Ori | Res | Addgene Number | Source |
|---|---|---|---|---|---|
| pSMART-HC-Kan | None | colE1 | Kan | NA | Lucigen |
| pHC-Kan-yibDp-xyrA | yibDp | colE1 | Kan | TBD | Previous Lab Work |
| pCASCADE-EV | ugpBp | p15A | Cm | TBD | Previous Lab Work |
| pCASCADE-gltA1 | ugpBp | p15A | Cm | TBD | Previous Lab Work |

TABLE 1-continued

Plasmids used in these Examples:

| Plasmids | Promoter | Ori | Res | Addgene Number | Source |
|---|---|---|---|---|---|
| pCASCADE-gltA2 | ugpBp | p15A | Cm | 65817 | Previous Lab Work |
| pCASCADE-zwf | ugpBp | p15A | Cm | 65825 | Previous Lab Work |
| pCACADE-udhA | ugpBp | p15A | Cm | 65818 | Previous Lab Work |
| pCASCADE-xylA | ugpBp | p15A | Cm | TBD | Previous Lab Work |
| pCASCADE-gltA1-zwf | ugpBp | p15A | Cm | TBD | Previous Lab Work |
| pCASCADE-gltA2-zwf | ugpBp | p15A | Cm | TBD | Previous Lab Work |
| pCASCADE-gltA1-udhA | ugpBp | p15A | Cm | TBD | Previous Lab Work |
| pCACADE-gltA2-udhA | ugpBp | p15A | Cm | 65819 | Previous Lab Work |
| pCASCADE-gltA1-gltA2 | ugpBp | p15A | Cm | TBD | Previous Lab Work |
| pCASCADE-gltA1-gltA2-zwf | ugpBp | p15A | Cm | TBD | Previous Lab Work |
| pCASCADE-gltA1-gltA2-udhA | ugpBp | p15A | Cm | TBD | Previous Lab Work |
| pCASCADE-zwf-xylA | ugpBp | p15A | Cm | TBD | This study |
| pCASCADE-udhA-xylA | ugpBp | p15A | Cm | TBD | This study |
| pCASCADE-gltA1-xylA | ugpBp | p15A | Cm | TBD | This study |
| pCASCADE-gltA2-xylA | ugpBp | p15A | Cm | TBD | This study |
| pCASCADE-gltA1-zwf-xylA | ugpBp | p15A | Cm | TBD | This study |
| pCASCADE-gltA2-zwf-xylA | ugpBp | p15A | Cm | TBD | This study |
| pCASCADE-gltA1-udhA-xylA | ugpBp | p15A | Cm | TBD | This study |
| pCACADE-gltA2-udhA-xylA | ugpBp | p15A | Cm | TBD | This study |
| pCASCADE-gltA1-gltA2-xylA | ugpBp | p15A | Cm | TBD | This study |
| pCASCADE-gltA1-gltA2-zwf-xylA | ugpBp | p15A | Cm | TBD | This study |
| pCASCADE-gltA1-gltA2-udhA-xylA | ugpBp | p15A | Cm | TBD | This study |

TABLE S1

Additional plasmids used in the Examples:

| Plasmid | Insert | promoter | Ori | Res | Addgene | Source |
|---|---|---|---|---|---|---|
| pSMART-HC-Kan | None | None | colE1 | Kan | NA | Lucigen |
| pCDF-ev | None | None | cloDF13 | Sm | 89596 | Previous Lab Work https://paperpile.com/c/I5xOoz/U3k3Y |
| pHCKan-xyrA | xyrA | yibDp[2] | colE1 | Kan | 158610 | This study |
| pCDF-pntAB | pntAB | ugpBp[2] | cloDF13 | Sm | 158609 | This study |
| pCASCADE-ev | none | ugpBp[2] | p15 | Cm | 65821 | Previous Lab Work |
| pCASCADE-g2 | gltAp2 gRNA | ugpBp[2] | p15 | Cm | 65817 | Previous Lab Work |
| pCASCADE-f | fabIp gRNA | ugpBp[2] | p15 | Cm | 66635 | This study |
| pCASCADE-z | zwfp gRNA | ugpBp[2] | p15 | Cm | 65825 | Previous Lab Work |
| pCASCADE-u | udhAp gRNA | ugpBp[2] | p15 | Cm | 65818 | This study |
| pCASCADE-x | xylAp gRNA | ugpBp[2] | p15 | Cm | 158611 | This study |
| pCASCADE-g2z | gltAp2, zwfp gRNA array | ugpBp[2] | p15 | Cm | 71338 | Previous Lab Work |

TABLE S1-continued

Additional plasmids used in the Examples:

| Plasmid | Insert | promoter | Ori | Res | Addgene | Source |
|---------|--------|----------|-----|-----|---------|--------|
| pCASCADE-g2u | gltAp2 udhAp gRNA array | ugpBp² | p15 | Cm | 65819 | This study |
| pCASCADE-g2x | gltAp2, xylAp gRNA array | ugpBp² | p15 | Cm | 158613 | This study |
| pCASCADE-zx | zwfp xylAp gRNA array | ugpBp² | p15 | Cm | 158614 | This study |
| pCASCADE-ux | udhAp, xylAp gRNA array | ugpBp² | p15 | Cm | 158612 | This study |
| pCASCADE-fg2 | fabIp, gltAp2 gRNA array | ugpBp² | p15 | Cm | 71341 | This study |
| pCASCADE-fz | fabIp, zwf gRNA array | ugpBp² | p15 | Cm | 71335 | This study |

TABLE 2

Host strains used in these Examples:

| Strain | Proteolytic Abbreviation | Genotype | Source |
|--------|--------------------------|----------|--------|
| DLF_0025 | Control/None | F-, λ-, Δ(araD-araB)567, lacZ4787(del)(::rrnB-3), rph-1, Δ(rhaD-rhaB)568, hsdR514, ΔackA-pta, ΔpoxB, ΔpflB, ΔldhA, ΔadhE, ΔsspB, ΔiclR, ΔarcA, Δcas3::tm-ugpb-sspB-pro [casA*] | Previous Lab Work |
| DLF_0025-X | X | DLF_0025, xylA-DAS + 4-ampR | This Study |
| DLF_0025-F | F | DLF_0025, fabI-DAS + 4-gentR | Previous Lab Work |
| DLF_0025-G | G | DLF_0025, gltA-DAS + 4-zeoR | Previous Lab Work |
| DLF_0025-Z | Z | F_0025, zwf-DAS + 4-bsdR | Previous Lab Work |
| DLF_0025-U | U | DLF_0025, udhA-DAS + 4-bsdR | Previous Lab Work |
| DLF_0025-GU | GU | DLF_0025, gltA-DAS + 4-zeoR, udhA-DAS + 4-bsdR | Previous Lab Work |
| DLF_0025-GZ | GZ | DLF_0025, gltA-DAS + 4-zeoR, zwf-DAS + 4-bsdR | Previous Lab Work |
| DLF_0025-FG | FG | DLF_0025, fabI-DAS + 4-gentR, gltA-DAS + 4-zeoR | Previous Lab Work |
| DLF_0025-FZ | FZ | DLF_0025, fabI-DAS + 4-gentR, zwf-DAS + 4-bsdR | Previous Lab Work |
| DLF_0025-FU | FU | DLF_0025, fabI-DAS + 4-gentR, udhA-DAS + 4-bsdR | Previous Lab Work |
| DLF_0025-FGU | FGU | DLF_0025, fabI-DAS + 4-gentR, gltA-DAS + 4-zeoR, udhA-DAS + 4-bsdR | Previous Lab Work |
| DLF_0025-FGZ | FGZ | DLF_0025, fabI-DAS + 4-gentR, gltA-DAS + 4-zeoR, zwf-DAS + 4-bsdR | Previous Lab Work |
| DLF_0025-FX | FX | DLF_0025, fabI-DAS + 4-gentR, xylA-DAS + 4-ampR | This Study |
| DLF_0025-FGX | FGX | DLF_0025, fabI-DAS + 4-gentR, gltA-DAS + 4-zeoR, xylA-DAS + 4-ampR | This Study |
| DLF_0025-FZX | FZX | DLF_0025, fabI-DAS + 4-gentR, zwf-DAS + 4-bsdR, xylA-DAS + 4-ampR | This Study |
| DLF_0025-FUX | FUX | DLF_0025, fabI-DAS + 4-gentR, udhA-DAS + 4-bsdR, xylA-DAS + 4-ampR | This Study |
| DLF_0025-FGUX | FGUX | DLF_0025, fabI-DAS + 4-gentR, gltA-DAS + 4-zeoR, udhA-DAS + 4-bsdR, xylA-DAS + 4-ampR | This Study |
| DLF_0025-FGZX | FGZX | DLF_0025, fabI-DAS + 4-gentR, gltA-DAS + 4-zeoR, zwf-DAS + 4-bsdR, xylA-DAS + 4-ampR | This Study |
| DLF_0025-UX | UX | DLF_0025, udhA-DAS + 4-bsdR, xylA-DAS + 4-ampR | This Study |
| DLF_0025-ZX | ZX | DLF_0025, zwf-DAS + 4-bsdR, xylA-DAS + 4-ampR | This Study |

TABLE S2

Additional Strains used in the Examples:

| Strain | Genotype | Source |
|---|---|---|
| DLF_Z0025 | F-, λ-, Δ(araD-araB)567, lacZ4787(del)(::rrnB-3), rph-1, Δ(rhaD-rhaB)568, hsdR514, ΔackA-pta, ΔpoxB, ΔpflB, ΔldhA, ΔadhE, ΔiclR, ΔarcA, ΔsspB, Δcas3::tm-ugpb-sspB-pro-casA. | Previous Lab Work |
| DLF_Z0043 | DLF_Z0025, gltA-DAS + 4-zeoR | Previous Lab Work |
| DLF_Z1002 | DLF_Z0025, zwf-DAS + 4-bsdR | Previous Lab Work |
| DLF_Z0044 | DLF_Z0025, gltA-DAS + 4-zeoR, zwf-DAS + 4-bsdR | Previous Lab Work |
| DLF_Z0028 | DLF_Z0025, fabI-DAS + 4-gentR | This study |
| DLF_Z0028 G | DLF_Z0025, fabI-sfGFP-gentR | This study |
| DLF_Z0028 GD | DLF_Z0025, fabI-sfGFP-DAS + 4-gentR | This study |
| DLF_Z0763 | DLF_Z0025, udhA-DAS + 4-bsdR | This study |
| DLF_Z0039 | fDLF_Z0025, fabI-DAS + 4-gentR, gltA-DAS + 4-zeoR | This study |
| DLF_Z0040 | DLF_Z0025, fabI-DAS + 4-gentR, zwf-DAS + 4-bsdR | This study |
| DLFZ_0045 | DLF_Z0025, fabI-DAS + 4-gentR, udhA-DAS + 4-bsdR | This study |
| DLFZ_0046 | DLF_Z0025, fabI-DAS + 4-gentR, gltA-DAS + 4-zeoR, zwf-DAS + 4-bsdR | This study |
| DLFZ_0047 | DLF_Z0025, fabI-DAS + 4-gentR, gltA-DAS + 4-zeoR, udhA-DAS + 4-bsdR | This study |
| SL_0001 | DLF_Z0025, xylA-DAS + 4-ampR | This study |
| SL_0002 | DLF_Z0025, fabI-DAS + 4-gentR, xylA -DAS + 4-ampR | This study |
| SL_0003 | DLF_Z0025, fabI-DAS + 4-gentR, gltA-DAS + 4-zeoR, xylA -DAS + 4-ampR | This study |
| SL_0004 | DLF_Z0025, fabI-DAS + 4-gentR, zwf-DAS + 4-bsdR, xylA -DAS + 4-ampR | This study |
| SL_0005 | DLF_Z0025, fabI-DAS + 4-gentR, udhA-DAS + 4-bsdR, xylA -DAS + 4-ampR | This study |
| SL_0006 | DLF_Z0025, fabI-DAS + 4-gentR, gltA-DAS + 4-zeoR, udhA-DAS + 4-bsdR, xylA -DAS + 4-ampR | This study |
| SL_0007 | DLF_Z0025, fabI-DAS + 4-gentR, gltA-DAS + 4-zeoR, zwf-DAS + 4-bsdR, xylA -DAS + 4-ampR | This study |
| SL_0008 | DLF_Z0025, gltA-DAS + 4-zeoR, udhA-DAS + 4-bsdR | This study |
| SL_0009 | DLF_Z0025, zwf-DAS + 4, -bsdR xylA -DAS + 4-ampR | This study |
| SL_0010 | DLF_Z0025, fabI-DAS + 4-gentR, zwf-DAS + 4-bsdR, ΔydbK | This study |
| SL_0011 | DLF_Z0025, fabI-DAS + 4-gentR, zwf-DAS + 4-bsdR, Δfpr | This study |

Ori—origin of replication,
Res—resistance marker,
Sm—pectinomycin,
Cm—chloramphenicol,
Kan—kanamycin,
Amp—ampicillin Chromosomal modifications were constructed using standard recombineering methodologies. A C-terminal DAS+4 tag on the xylA gene was added by direct integration and selected through integration of antibiotic resistance cassettes 3' of the gene. All strains were confirmed by PCR, agarose gel electrophoresis and confirmed by sequencing.

TABLE 3

Sequences of synthetic DNA:

xylA-DAS4-ampR (SEQ ID NO: 1)

GATACGATGGCACTGGCGCTGAAAATTGCAGCGCG

CATGATTGAAGATGGCGAGCTGGATAAACGCATCG

CGCAGCGTTATTCCGGCTGGAATAGCGAATTGGGC

CAGCAAATCCTGAAAGGCCAAATGTCACTGGCAGA

TTTAGCCAAATATGCTCAGGAACATCATTTGTCTC

CGGTGCATCAGAGTGGTCGCCAGGAACAACTGGAA

TABLE 3-continued

Sequences of synthetic DNA:

AATCTGGTAAACCATTATCTGTTCGACAAAGCGGC

CAACGATGAAAACTATTCTGAAAACTATGCGGATG

CGTCTTAATGATAAGGACCGTGTTGACAATTAATC

ATCGGCATAGTATATCGGCATAGTATAATACGACA

AGGTGAGGAACTAAACCATGAGTATTCAACATTTC

CGTGTCGCCCTTATTCCCTTTTTTGCGGCATTTTG

CCTTCCTGTTTTTGCTCACCCAGAAACGCTGGTGA

AAGTAAAAGATGCTGAAGATCAGTTGGGTGCACGA

GTGGGTTACATCGAACTGGATCTCAACAGCGGTAA

GATCCTTGAGAGTTTACGCCCCGAAGAACGTTTTC

TABLE 3-continued

| Sequences of synthetic DNA: |
|---|
| CAATGATGAGCACTTTTAAAGTTCTGCTATGTGGC |
| GCGGTATTATCCCGTATTGACGCCGGGCAAGAGCA |
| ACTCGGTCGCCGCATACACTATTCTCAGAATGACT |
| TGGTTGAGTACTCACCAGTCACAGAAAAGCATCTC |
| ACGGATGGCATGACAGTAAGAGAATTATGCAGTGC |
| TGCCATAACCATGAGTGATAACACTGCGGCCAACT |
| TACTTCTGGCAACGATCGGAGGACCGAAGGAGCTA |
| ACCGCTTTTTTGCACAACATGGGGGATCATGTAAC |
| TCGCCTTGATCGTTGGGAACCGGAGCTGAATGAAG |
| CCATACCAAACGACGAGCGTGACACCACGATGCCT |
| GTAGCAATGGCAACAACGTTGCGCAAACTATTAAC |
| TGGCGAACTACTTACTCTAGCTTCCCGGCAACAAT |
| TAATAGACTGGATGGAGGCGGATAAAGTTGCAGGA |
| TCACTTCTGCGCTCGGCCCTCCCGGCTGGCTGGTT |
| TATTGCTGATAAATCTGGAGCCGGTGAGCGTGGGT |
| CTCGCGGTATCATTGCAGCACTGGGGCCAGATGGT |
| AAGCCCTCCCGCATCGTAGTTATCTACACGACGGG |
| GAGTCAGGCAACTATGGATGAACGAAATAGACAGA |
| TCGCTGAGATAGGTGCCTCACTGATTAAGCATTGG |
| TAGTAAGTAGGGATAACAGGGTAATCGGCTAACTG |
| TGCAGTCCGTTGGCCCGGTTATCGGTAGCGATACC |
| GGGCATTTTTTTAAGGAACGATCGATATGTATATC |
| GGGATAGATCTTGGCACCTCGGGCGTAAAAGTTAT |
| TTTGCTCAACGAGCAGGGTGAGGTGGTTGCTGCGC |
| AAACGGAAAAGCTGACCGTTTCGCGCCCGCATCCA |
| CTCTGGTCGGAACAAGACCCGGAACAGTGGTGGCA |
| GGCAACTGATCGCGCAA | fabI-DAS + 4-gentR (SEQ ID NO: 2)

| |
|---|
| CTATTGAAGATGTGGGTAACTCTGCGGCATTCCTG |
| TGCTCCGATCTCTCTGCCGGTATCTCCGGTGAAGT |
| GGTCCACGTTGACGGCGGTTTCAGCATTGCTGCAA |
| TGAACGAACTCGAACTGAAAGCGGCCAACGATGAA |
| AACTATTCTGAAAACTATGCGGATGCGTCTTAATA |
| GGAAGTTCCTATTCTCTAGAAAGTATAGGAACTTC |
| CGAATCCATGTGGGAGTTTATTCTTGACACAGATA |
| TTTATGATATAATAACTGAGTAAGCTTAACATAAG |
| GAGGAAAAACATATGTTACGCAGCAGCAACGATGT |
| TACGCAGCAGGGCAGTCGCCCTAAAACAAAGTTAG |
| GTGGCTCAAGTATGGGCATCATTCGCACATGTAGG |

TABLE 3-continued

| Sequences of synthetic DNA: |
|---|
| CTCGGCCCTGACCAAGTCAAATCCATGCGGGCTGC |
| TCTTGATCTTTTCGGTCGTGAGTTCGGAGACGTAG |
| CCACCTACTCCCAACATCAGCCGGACTCCGATTAC |
| CTCGGGAACTTGCTCCGTAGTAAGACATTCATCGC |
| GCTTGCTGCCTTCGACCAAGAAGCGGTTGTTGGCG |
| CTCTCGCGGCTTACGTTCTGCCCAAGTTTGAGCAG |
| CCGCGTAGTGAGATCTATATCTATGATCTCGCAGT |
| CTCCGGCGAGCACCGGAGGCAGGGCATTGCCACCG |
| CGCTCATCAATCTCCTCAAGCATGAGGCCAACGCG |
| CTTGGTGCTTATGTGATCTACGTGCAAGCAGATTA |
| CGGTGACGATCCCGCAGTGGCTCTCTATACAAAGT |
| TGGGCATACGGGAAGAAGTGATGCACTTTGATATC |
| GACCCAAGTACCGCCACCTAAGAAGTTCCTATTCT |
| CTAGAAAGTATAGGAACTTCCGTTCTGTTGGTAAA |
| GATGGGCGGCGTTCTGCCGCCCGTTATCTCTGTTA |
| TACCTTTCTGATATTTGTTATCGCCGATCCGTCTT |
| TCTCCCCTTCCCGCCTTGCGTCAGG | gltA-DAS + 4-zeoR (SEQ ID NO: 3)

| |
|---|
| GTATTCCGTCTTCCATGTTCACCGTCATTTTCGCA |
| ATGGCACGTACCGTTGGCTGGATCGCCCACTGGAG |
| CGAAATGCACAGTGACGGTATGAAGATTGCCCGTC |
| CGCGTCAGCTGTATACAGGATATGAAAAACGCGAC |
| TTTAAAAGCGATATCAAGCGTGCGGCCAACGATGA |
| AAACTATTCTGAAAACTATGCGGATGCGTCTTAAT |
| AGTTGACAATTAATCATCGGCATAGTATATCGGCA |
| TAGTATAATACGACTCACTATAGGAGGGCCATCAT |
| GGCCAAGTTGACCAGTGCCGTTCCGGTGCTCACCG |
| CGCGCGACGTCGCCGGAGCGGTCGAGTTCTGGACC |
| GACCGGCTCGGGTTCTCCCGGGACTTCGTGGAGGA |
| CGACTTCGCCGGTGTGGTCCGGGACGACGTGACCC |
| TGTTCATCAGCGCGGTCCAGGACCAGGTGGTGCCG |
| GACAACACCCTGGCCTGGGTGTGGGTGCGCGGCCT |
| GGACGAGCTGTACGCCGAGTGGTCGGAGGTCGTGT |
| CCACGAACTTCCGGGACGCCTCCGGGCCGGCCATG |
| ACCGAGATCGGCGAGCAGCCGTGGGGGCGGGAGTT |
| CGCCCTGCGCGACCCGGCCGGCAACTGCGTGCACT |
| TTGTGGCAGAGGAGCAGGACTGAGGATAAGTAATG |
| GTTGATTGCTAAGTTGTAAATATTTTAACCCGCCG |
| TTCATATGGCGGGTTGATTTTTATATGCCTAAACA |

TABLE 3-continued

Sequences of synthetic DNA:

CAAAAAATTGTAAAAATAAAATCCATTAACAGACC

TATATAGATATTTAAAAAGAATAGAACAGCTCAAA

TTATCAGCAACCCAATACTTTCAATTAAAAACTTC

ATGGTAGTCGCATTTATAACCCTATGAAA udhA-DAS + 4-bsdR
(SEQ ID NO: 4)
TCTGGGTATTCACTGCTTTGGCGAGCGCGCTGCCG

AAATTATTCATATCGGTCAGGCGATTATGGAACAG

AAAGGTGGCGGCAACACTATTGAGTACTTCGTCAA

CACCACCTTTAACTACCCGACGATGGCGGAAGCCT

ATCGGGTAGCTGCGTTAAACGGTTTAAACCGCCTG

TTTGCGGCCAACGATGAAAACTATTCTGAAAACTA

TGCGGATGCGTCTTAATAGTTGACAATTAATCATC

GGCATAGTATATCGGCATAGTATAATACGACTCAC

TATAGGAGGGCCATCATGAAGACCTTCAACATCTC

TCAGCAGGATCTGGAGCTGGTGGAGGTCGCCACTG

AGAAGATCACCATGCTCTATGAGGACAACAAGCAC

CATGTCGGGGCGGCCATCAGGACCAAGACTGGGGA

GATCATCTCTGCTGTCCACATTGAGGCCTACATTG

GCAGGGTCACTGTCTGTGCTGAAGCCATTGCCATT

GGGTCTGCTGTGAGCAACGGGCAGAAGGACTTTGA

CACCATTGTGGCTGTCAGGCACCCCTACTCTGATG

AGGTGGACAGATCCATCAGGGTGGTCAGCCCCTGT

GGCATGTGCAGAGAGCTCATCTCTGACTATGCTCC

TGACTGCTTTGTGCTCATTGAGATGAATGGCAAGC

TGGTCAAAACCACCATTGAGGAACTCATCCCCCTC

AAGTACACCAGGAACTAAAGTAAAACTTTATCGAA

ATGGCCATCCATTCTTGCGCGGATGGCCTCTGCCA

GCTGCTCATAGCGGCTGCGCAGCGGTGAGCCAGGA

CGATAAACCAGGCCAATAGTGCGGCGTGGTTCCGG

CTTAATGCACGG zwf-DAS + 4-bsdR
(SEQ ID NO: 5)
GAAGTGGAAGAAGCCTGGAAATGGGTAGACTCCAT

TACTGAGGCGTGGGCGATGGACAATGATGCGCCGA

AACCGTATCAGGCCGGAACCTGGGGACCCGTTGCC

TCGGTGGCGATGATTACCCGTGATGGTCGTTCCTG

GAATGAGTTTGAGGCGGCCAACGATGAAAACTATT

CTGAAAACTATGCGGATGCGTCTTAATAGTTGACA

ATTAATCATCGGCATAGTATATCGGCATAGTATAA

TACGACTCACTATAGGAGGGCCATCATGAAGACCT

TABLE 3-continued

Sequences of synthetic DNA:

TCAACATCTCTCAGCAGGATCTGGAGCTGGTGGAG

GTCGCCACTGAGAAGATCACCATGCTCTATGAGGA

CAACAAGCACCATGTCGGGGCGGCCATCAGGACCA

AGACTGGGGAGATCATCTCTGCTGTCCACATTGAG

GCCTACATTGGCAGGGTCACTGTCTGTGCTGAAGC

CATTGCCATTGGGTCTGCTGTGAGCAACGGGCAGA

AGGACTTTGACACCATTGTGGCTGTCAGGCACCCC

TACTCTGATGAGGTGGACAGATCCATCAGGGTGGT

CAGCCCCTGTGGCATGTGCAGAGAGCTCATCTCTG

ACTATGCTCCTGACTGCTTTGTGCTCATTGAGATG

AATGGCAAGCTGGTCAAAACCACCATTGAGGAACT

CATCCCCCTCAAGTACACCAGGAACTAAAGTAATA

TCTGCGCTTATCCTTTATGGTTATTTTACCGGTAA

CATGATCTTGCGCAGATTGTAGAACAATTTTTACA

CTTTCAGGCCTCGTGCGGATTCACCCACGAGGCTT

TTTTTATTACACTGACTGAAACGTTTTTGCCCTAT

GAGCTCCGGTTACAGGCGTTTCAGTCATAAATCCT

CTGAATGAAACGCGTTGTGAATC

TABLE S3

Additional synthetic DNA:

xylA-DAS4-ampR
(SEQ ID NO: 1)
GATACGATGGCACTGGCGCTGAAAATTGCAGCGCGCATGA

TTGAAGATGGCGAGCTGGATAAACGCATCGCGCAGCGTTA

TTCCGGCTGGAATAGCGAATTGGGCCAGCAAATCCTGAAA

GGCCAAATGTCACTGGCAGATTTAGCCAAATATGCTCAGG

AACATCATTTGTCTCCGGTGCATCAGAGTGGTCGCCAGGA

ACAACTGGAAAATCTGGTAAACCATTATCTGTTCGACAAA

GCGGCCAACGATGAAAACTATTCTGAAAACTATGCGGATG

CGTCTTAATGATAAGGACCGTGTTGACAATTAATCATCGG

CATAGTATATCGGCATAGTATAATACGACAAGGTGAGGAA

CTAAACCATGAGTATTCAACATTTCCGTGTCGCCCTTATT

CCCTTTTTTGCGGCATTTTGCCTTCCTGTTTTTGCTCACC

CAGAAACGCTGGTGAAAGTAAAAGATGCTGAAGATCAGTT

GGGTGCACGAGTGGGTTACATCGAACTGGATCTCAACAGC

GGTAAGATCCTTGAGAGTTACGCCCCGAAGAACGTTTTC

CAATGATGAGCACTTTTAAAGTTCTGCTATGTGGCGCGGT

ATTATCCCGTATTGACGCCGGGCAAGAGCAACTCGGTCGC

CGCATACACTATTCTCAGAATGACTTGGTTGAGTACTCAC

TABLE S3-continued

Additional synthetic DNA:

CAGTCACAGAAAAGCATCTCACGGATGGCATGACAGTAAG

AGAATTATGCAGTGCTGCCATAACCATGAGTGATAACACT

GCGGCCAACTTACTTCTGGCAACGATCGGAGGACCGAAGG

AGCTAACCGCTTTTTTGCACAACATGGGGGATCATGTAAC

TCGCCTTGATCGTTGGGAACCGGAGCTGAATGAAGCCATA

CCAAACGACGAGCGTGACACCACGATGCCTGTAGCAATGG

CAACAACGTTGCGCAAACTATTAACTGGCGAACTACTTAC

TCTAGCTTCCCGGCAACAATTAATAGACTGGATGGAGGCG

GATAAAGTTGCAGGATCACTTCTGCGCTCGGCCCTCCCGG

CTGGCTGGTTTATTGCTGATAAATCTGGAGCCGGTGAGCG

TGGGTCTCGCGGTATCATTGCAGCACTGGGGCCAGATGGT

AAGCCCTCCCGCATCGTAGTTATCTACACGACGGGGAGTC

AGGCAACTATGGATGAACGAAATAGACAGATCGCTGAGAT

AGGTGCCTCACTGATTAAGCATTGGTAGTAAGTAGGGATA

ACAGGGTAATCGGCTAACTGTGCAGTCCGTTGGCCCGGTT

ATCGGTAGCGATACCGGGCATTTTTTTAAGGAACGATCGA

TATGTATATCGGGATAGATCTTGGCACCTCGGGCGTAAAA

GTTATTTTGCTCAACGAGCAGGGTGAGGTGGTTGCTGCGC

AAACGGAAAAGCTGACCGTTTCGCGCCCGCATCCACTCTG

GTCGGAACAAGACCCGGAACAGTGGTGGCAGGCAACTGAT

CGCGCAA fabI-DAS + 4-gentR (SEQ ID NO: 2)

CTATTGAAGATGTGGGTAACTCTGCGGCATTCCTGTGCTC

CGATCTCTCTGCCGGTATCTCCGGTGAAGTGGTCCACGTT

GACGGCGGTTTCAGCATTGCTGCAATGAACGAACTCGAAC

TGAAAGCGGCCAACGATGAAAACTATTCTGAAAACTATGC

GGATGCGTCTTAATAGGAAGTTCCTATTCTCTAGAAAGTA

TAGGAACTTCCGAATCCATGTGGGAGTTTATTCTTGACAC

AGATATTTATGATATAATAACTGAGTAAGCTTAACATAAG

GAGGAAAAACATATGTTACGCAGCAGCAACGATGTTACGC

AGCAGGGCAGTCGCCCTAAAACAAAGTTAGGTGGCTCAAG

TATGGGCATCATTCGCACATGTAGGCTCGGCCCTGACCAA

GTCAAATCCATGCGGGCTGCTCTTGATCTTTTCGGTCGTG

AGTTCGGAGACGTAGCCACCTACTCCCAACATCAGCCGGA

CTCCGATTACCTCGGGAACTTGCTCCGTAGTAAGACATTC

ATCGCGCTTGCTGCCTTCGACCAAGAAGCGGTTGTTGGCG

CTCTCGCGGCTTACGTTCTGCCCAAGTTTGAGCAGCCGCG

TAGTGAGATCTATATCTATGATCTCGCAGTCTCCGGCGAG

CACCGGAGGCAGGGCATTGCCACCGCGCTCATCAATCTCC

TABLE S3-continued

Additional synthetic DNA:

TCAAGCATGAGGCCAACGCGCTTGGTGCTTATGTGATCTA

CGTGCAAGCAGATTACGGTGACGATCCCGCAGTGGCTCTC

TATACAAAGTTGGGCATACGGGAAGAAGTGATGCACTTTG

ATATCGACCCAAGTACCGCCACCTAAGAAGTTCCTATTCT

CTAGAAAGTATAGGAACTTCCGTTCTGTTGGTAAAGATGG

GCGGCGTTCTGCCGCCCGTTATCTCTGTTATACCTTTCTG

ATATTTGTTATCGCCGATCCGTCTTTCTCCCCTTCCCGCC

TTGCGTCAGG fabI-sfGFP-gentR (SEQ ID NO: 21)

AAAGACTTCCGCAAAATGCTGGCTCATTGCGAAGCCGTTA

CCCCGATTCGCCGTACCGTTACTATTGAAGATGTGGGTAA

CTCTGCGGCATTCCTGTGCTCCGATCTCTCTGCCGGTATC

TCCGGTGAAGTGGTCCACGTTGACGGCGGTTTCAGCATTG

CTGCAATGAACGAACTCGAACTGAAAGGGGGTTCAGGCGG

GTCGGGTGGCgtgagcaagggcgaggagctgttcaccggg gtggtgcccatcctggtcgagctggacggcgacgtaaacg gccacaagttcagcgtgcgcggcgagggcgagggcgatgc caccaacggcaagctgaccctgaagttcatctgcaccacc ggcaagctgcccgtgccctggcccaccctcgtgaccaccc tgacctacggcgtgcagtgcttcagccgctaccccgacca catgaagcgccacgacttcttcaagtccgccatgcccgaa ggctacgtccaggagcgcaccatcagcttcaaggacgacg gcacctacaagacccgcgccgaggtgaagttcgagggcga caccctggtgaaccgcatcgagctgaagggcatcgacttc aaggaggacggcaacatcctggggcacaagctggagtaca acttcaacagccacaacgtctatatcaccgccgacaagca gaagaacggcatcaaggccaacttcaagatccgccacaac gtggaggacggcagcgtgcagctcgccgaccactaccagc agaacacccccatcggcgacggccccgtgctgctgcccga caaccactacctgagcacccagtccgtgctgagcaaagac cccaacgagaagcgcgatcacatggtcctgctggagttcg tgaccgccgccgggatcactcacggcatggacgagctgta caagTAATGACGAATCCATGTGGGAGTTTATTCTTGACAC

AGATATTTATGATATAATAACTGAGTAAGCTTAACATAAG

GAGGAAAAACATATGTTGCGTAGCTCTAACGATGTGACGC

AACAAGGTTCGCGTCCAAAGACAAAATTGGGAGGCAGTAG

CATGGGGATCATTCGCACTTGTCGCCTGGGGCCAGACCAG

GTGAAGTCAATGCGTGCGGCTCTGGACTTATTCGGGCGCG

AATTTGGAGATGTAGCCACTTACTCACAGCACCAACCGGA

TABLE S3-continued

Additional synthetic DNA:

CAGTGATTACTTGGGGAATTTACTTCGCAGTAAAACTTTT

ATCGCTTTGGCCGCTTTCGACCAGGAGGCTGTAGTAGGTG

CGTTGGCAGCCTATGTTCTTCCTAAATTCGAGCAACCGCG

TAGCGAAATTTACATCTATGATCTTGCAGTCTCCGGCGAA

CATCGCCGTCAGGGGATCGCCACAGCTTTAATCAACCTTT

TGAAGCATGAGGCTAATGCACTTGGACGTACGTGATTTA

TGTGCAGGCTGACTACGGTGATGATCCTGCAGTCGCTCTG

TACACCAAACTGGGTATCCGCGAGGAGGTCATGCACTTTG

ATATTGACCCGTCGACGGCTACCTAAGTTCTGTTGGTAAA

GATGGGCGGCGTTCTGCCGCCCGTTATCTCTGTTATACCT

TTCTGATATTTGTTATCGCCGATCCGTCTTTCTCCCCTTC

CCGCCTTGCGTCAGG fabI-sfGFP-DAS + 4-gentR
                                   (SEQ ID NO: 22)
AAAGACTTCCGCAAATGCTGGCTCATTGCGAAGCCGTTA

CCCCGATTCGCCGTACCGTTACTATTGAAGATGTGGGTAA

CTCTGCGGCATTCCTGTGCTCCGATCTCTCTGCCGGTATC

TCCGGTGAAGTGGTCCACGTTGACGGCGGTTTCAGCATTG

CTGCAATGAACGAACTCGAACTGAAAGGGGGTTCAGGCGG

GTCGGGTGGCgtgagcaagggcgaggagctgttcaccggg gtggtgcccatcctggtcgagctggacggcgacgtaaacg gccacaagttcagcgtgcgcggcgagggcgagggcgatgc caccaacggcaagctgaccctgaagttcatctgcaccacc ggcaagctgcccgtgccctggcccaccctcgtgaccaccc tgacctacggcgtgcagtgcttcagccgctaccccgacca catgaagcgccacgacttcttcaagtccgccatgcccgaa ggctacgtccaggagcgcaccatcagcttcaaggacgacg gcacctacaagacccgcgcgaggtgaagttcgagggcga caccctggtgaaccgcatcgagctgaagggcatcgacttc aaggaggacggcaacatcctggggcacaagctggagtaca acttcaacagccacaacgtctatatcaccgccgacaagca gaagaacggcatcaaggccaacttcaagatccgccacaac gtggaggacggcagcgtgcagctcgccgaccactaccagc agaacacccccatcggcgacggccccgtgctgctgcccga caaccactacctgagcacccagtccgtgctgagcaaagac cccaacgagaagcgcgatcacatggtcctgctggagttcg tgaccgccgccgggatcactcacggcatggacgagctgta caagGGTGGGGGTGGGAGCGGCGGCGGTGGCTCCGCGGCC

AACGATGAAAACTATTCTGAAAACTATGCGGATGCGTCTT

AATGACGAATCCATGTGGGAGTTTATTCTTGACACAGATA

TTTATGATATAATAACTGAGTAAGCTTAACATAAGGAGGA

AAAACATATGTTGCGTAGCTCTAACGATGTGACGCAACAA

GGTTCGCGTCCAAAGACAAAATTGGGAGGCAGTAGCATGG

GGATCATTCGCACTTGTCGCCTGGGGCCAGACCAGGTGAA

GTCAATGCGTGCGGCTCTGGACTTATTCGGGCGCGAATTT

GGAGATGTAGCCACTTACTCACAGCACCAACCGGACAGTG

ATTACTTGGGGAATTTACTTCGCAGTAAAACTTTTATCGC

TTTGGCCGCTTTCGACCAGGAGGCTGTAGTAGGTGCGTTG

GCAGCCTATGTTCTTCCTAAATTCGAGCAACCGCGTAGCG

AAATTTACATCTATGATCTTGCAGTCTCCGGCGAACATCG

CCGTCAGGGGATCGCCACAGCTTTAATCAACCTTTTGAAG

CATGAGGCTAATGCACTTGGAGCGTACGTGATTTATGTGC

AGGCTGACTACGGTGATGATCCTGCAGTCGCTCTGTACAC

CAAACTGGGTATCCGCGAGGAGGTCATGCACTTTGATATT

GACCCGTCGACGGCTACCTAAGTTCTGTTGGTAAAGATGG

GCGGCGTTCTGCCGCCCGTTATCTCTGTTATACCTTTCTG

ATATTTGTTATCGCCGATCCGTCTTTCTCCCCTTCCCGCC

TTGCGTCAGG udhA-DAS + 4-bsdR
                                   (SEQ ID NO: 4)
TCTGGGTATTCACTGCTTTGGCGAGCGCGCTGCCGAAATT

ATTCATATCGGTCAGGCGATTATGGAACAGAAAGGTGGCG

GCAACACTATTGAGTACTTCGTCAACACCACCTTTAACTA

CCCGACGATGGCGGAAGCCTATCGGGTAGCTGCGTTAAAC

GGTTTAAACCGCCTGTTTGCGGCCAACGATGAAAACTATT

CTGAAAACTATGCGGATGCGTCTTAATAGTTGACAATTAA

TCATCGGCATAGTATATCGGCATAGTATAATACGACTCAC

TATAGGAGGGCCATCATGAAGACCTTCAACATCTCTCAGC

AGGATCTGGAGCTGGTGGAGGTCGCCACTGAGAAGATCAC

CATGCTCTATGAGGACAACAAGCACCATGTCGGGGCGGCC

ATCAGGACCAAGACTGGGGAGATCATCTCTGCTGTCCACA

TTGAGGCCTACATTGGCAGGGTCACTGTCTGTGCTGAAGC

CATTGCCATTGGGTCTGCTGTGAGCAACGGGCAGAAGGAC

TTTGACACCATTGTGGCTGTCAGGCACCCCTACTCTGATG

AGGTGGACAGATCCATCAGGGTGGTCAGCCCCTGTGGCAT

GTGCAGAGAGCTCATCTCTGACTATGCTCCTGACTGCTTT

GTGCTCATTGAGATGAATGGCAAGCTGGTCAAAACCACCA

TTGAGGAACTCATCCCCCCTCAAGTACACCAGGAACTAAAG

TABLE S3-continued

| Additional synthetic DNA: |
| --- |
| TAAAACTTTATCGAAATGGCCATCCATTCTTGCGCGGATG |
| GCCTCTGCCAGCTGCTCATAGCGGCTGCGCAGCGGTGAGC |
| CAGGACGATAAACCAGGCCAATAGTGCGGCGTGGTTCCGG |
| CTTAATGCACGG |

The xyrA gene from *Aspergillus niger* was codon optimized for *E. coli* and the plasmid, pHCKan-INS: yibDp-6× his-xyrA, enabling the low phosphate induction of xylose reductase, was constructed by TWIST Biosciences, pCAS-CADE guide RNA array plasmids were prepared by the combination of PCR and Gibson assembly as previously described.

| Plasmids/<br>primers<br>name | sequences |
| --- | --- |
| gltA1 | TCGAGTTCCCCGCGCCAGCGGGGATA<br>AACCGAAAAGCATATAATGCGTAAAA<br>GTTATGAAGTTCGAGTTCCCCGCGCC<br>AGCGGGGATAAACCG<br>(SEQ ID NO: 6) |
| gltA1-FOR | CCGGATGAGCATTCATCAGGCGGGCAAG<br>(SEQ ID NO: 7) |
| gltA1-REV | CGGTTTATCCCCGCTGGCGCGGGGAA<br>CTCGAACTTCATAACTTTTAC<br>(SEQ ID NO: 8) |
| gltA2 | TATTGACCAATTCATTCGGGACAGTTA<br>TTAGTTCGAGTTCCCCGCGCCAGCGGG<br>GATAAACCG (SEQ ID NO: 9) |
| gltA2-FOR | CCGGATGAGCATTCATCAGGCGGGCAAG<br>(SEQ ID NO: 10) |
| gltA2-REV | CGGTTTATCCCCGCTGGCGCGGGGAACT<br>CGAACTAATAACTGTC<br>(SEQ ID NO: 11) |
| udhA | TTACCATTCTGTTGCTTTTATGTATAAG<br>AATCGAGTTCCCCGCGCCAGCGGGGATA<br>AACCG (SEQ ID NO: 12) |
| udhA-FOR | CCGGATGAGCATTCATCAGGCGGGCAAG<br>(SEQ ID NO: 13) |
| udhA-REV | CGGTTTATCCCCGCTGGCGCGGGGAACT<br>CGATTCTTATACATAAAAGC<br>(SEQ ID NO: 14) |
| zwf | CTCGTAAAAGCAGTACAGTGCACCGTAA<br>GATCGAGTTCCCCGCGCCAGCGGGGATA<br>AACCG (SEQ ID NO: 15) |
| zwf-FOR | CCGGATGAGCATTCATCAGGCGGGCAAG<br>(SEQ ID NO: 16) |
| zwf-REV | CGGTTTATCCCCGCTGGCGCGGGGAACT<br>CGATCTTACGGTGCACTGTAC<br>(SEQ ID NO: 17) |
| xylA | GGAGTGCCCAATATTACGACATCATCCA<br>TCTCGAGTTCCCCGCGCCAGCGGG<br>GATAAACCG<br>(SEQ ID NO: 18) |
| xylA-FOR | CCAGCGGGGATAAACCGGGAGTGCCCAA<br>TATTAC (SEQ ID NO: 19) |

-continued

| Plasmids/<br>primers<br>name | sequences |
| --- | --- |
| xylA-REV | CTTGCCCGCCTGATGAATGCTCATCCGG<br>(SEQ ID NO: 20) |

TABLE S4

| Additional oligonucleotides: | |
| --- | --- |
| Plasmids/<br>primers<br>name | Sequences |
| fablintF | GCAAAATGCTGGCTCATTG<br>(SEQ ID NO: 23) |
| gentR_intR | GCGATGAATGTCTTACTACGGA<br>(SEQ ID NO: 24) |
| gltA_int_F | TATCATCCTGAAAGCGATGG<br>(SEQ ID NO: 25) |
| zeointR | ACTGAAGCCCAGACGATC<br>(SEQ ID NO: 26) |
| zwfintF | CTGCTGGAAACCATGCG<br>(SEQ ID NO: 27) |
| udhAintF | CAAAAGAGATTCTGGGTATTCACT<br>(SEQ ID NO: 28) |
| bsdRintR | GAGCATGGTGATCTTCTCAGT<br>(SEQ ID NO: 29) |
| xylAintF | AGATGGCGAGCTGGATA<br>(SEQ ID NO: 30) |
| ampRintR | AGTACTCAACCAAGTCATTCTG<br>(SEQ ID NO: 31) |
| gltA2 | TATTGACCAATTCATTCGGGACAG<br>TTATTAGTTCGAGTTCCCCGCGC<br>CAGCGGGGATAAACCG<br>(SEQ ID NO: 6) |
| gltA2-FOR | CCGGATGAGCATTCATCAGGCGGG<br>CAAG<br>(SEQ ID NO: 7) |
| gltA2-REV | CGGTTTATCCCCGCTGGCGCGGGG<br>AACTCGAACTAATAACTGTC<br>(SEQ ID NO: 8) |
| udhA | TTACCATTCTGTTGCTTTTATGTA<br>TAAGAATCGAGTTCCCCGCGCCA<br>GCGGGGATAAACCG<br>(SEQ ID NO: 12) |
| udhA-FOR | CCGGATGAGCATTCATCAGGCGGG<br>CAAG<br>(SEQ ID NO: 13) |
| udhA-REV | CGGTTTATCCCCGCTGGCGCGGGG<br>AACTCGATTCTTATACATAAAA<br>GC(SEQ ID NO: 14) |
| xylA | GGAGTGCCCAATATTACGACATCA<br>TCCATCTCGAGTTCCCCGCGCCA<br>GCGGGGATAAACCG<br>(SEQ ID NO: 18) |

33

TABLE S4-continued

Additional oligonucleotides:

| Plasmids/ primers name | Sequences |
|---|---|
| xylA-FOR | CCAGCGGGGATAAACCGGGAGTGC CCAATATTAC (SEQ ID NO: 19) |
| xylA-REV | CTTGCCCGCCTGATGAATGCTCAT CCGG (SEQ ID NO: 20) |

Micro and 1 L Fermentations

Micro-fermentations and 1 L fermentations in instrumented bioreactors were performed as previously reported, except that xylose was substituted for glucose (1 gram xylose for 1 gram glucose) in all media formulations. Guide array stability was confirmed after transformation of pCAS-CADE vector by PCR prior to evaluation in 96 well plate micro-fermentations.

Xylose and Xylitol Quantification

In micro-fermentations, xylose and xylitol were quantified by commercial bioassays from Megazyme (Wicklow, Ireland, Catalog #K-XYLOSE and K-SORB), according to the manufacturer's instructions. All the results were tested by measuring the absorbance at 492 nm. For the quantification of tank fermentations, an HPLC method coupled with a refractive index detector was used to measure both xylose as well as xylitol. At 55° C., a Rezex ROA-Organic Acid H+ (8%) Analysis HPLC Column (CAT #: #00H-0138-K0, Phenomenex, Inc., Torrance, CA, 300×7.8 mme) was employed for the compound's separation. According to reference, we chose sulfuric acid as the isocratic eluent solvents, and the flow rate was set at 0.5 mL/min Waters Acquity H-Class UPLC integrated with a Waters 2414 Refractive Index (RI) detector (Waters Corp., Milford. MA. USA) was used for the chromatographic detection. Injection volume of sample and standard was set as 10 μL. Samples were diluted in 20 times using filtered ultrapure water to make all the sample points appear within the standards linear range. The standard variation range was between 0.01 to 20 g/L. MassLynx v4.1 software was used for all the peak integration and concentration analysis.

Fermentations.

Minimal media microfermentations were performed as previously reported (Moreb, E. A, et al. Media Robustness and scalability of phosphate regulated promoters useful for two-stage autoinduction in E. coli. ACS Synthetic Biology (2020) doi:10.1021/acssynbio.0c00182 and Menacho-Melgar. R, et al. Scalable, two-stage, autoinduction of recombinant protein expression in E. coli utilizing phosphate depletion. Biotechnol. Bioeng. 26, 44 (2020)) except that xylose was substituted for glucose (1 gram xylose for 1 gram glucose) in all media formulations. Guide array stability was confirmed after transformation of pCASCADE plasmids by PCR prior to evaluation according to Li et al.[24] Fed batch fermentations were performed as previously reported, again with xylose instead of glucose (Menacho-Melgar, R, et al. Scalable, two-stage, autoinduction of recombinant protein expression in E. coli utilizing phosphate depletion. Biotechnol. Bioeng. 26, 44 (2020). Xylose feeding was as modified as follows. The starting batch glucose concentration was 25 g/L. Concentrated sterile filtered xylose feed (500 g/L) was added to the tanks at an initial rate of 10 g/h when cells entered mid-exponential growth. This rate was then increased exponentially, doubling every 1.083 hours (65 min) until 40 g total glucose had been added, after which the feed was maintained at 1.75 g/hr. The feed was reduced to 0.875 g/hr due to xylose accumulation at 85 hrs post inoculation, and stopped at 120 hrs post inoculation.

(XyrA) Xylose Reductase Purification and Activity Assays

E. coli BL21 (DE3) (New England Biolabs, Ipswich, MA) with plasmid pHCKan-xyrA (bearing a 6×his tag) was cultured overnight in Luria Broth (Lenox formulation). The overnight culture was used to inoculate SM10++ media (with xylose as a carbon source instead of glucose) with appropriate antibiotics. Cells were cultured at 37° C., for 16 hours, then cells were centrifuged, and the pellet was washed with SM10 No phosphate media. Next, the washed pellet was resuspended and cultured in SM10 No Phosphate media again with the appropriate antibiotics. After the expression, the postproduction cells were lysed by a freeze-thaw cycle. XyrA protein was purified using Ni-NTA Resin (G-Biosciences, Cat #786-939) according to manufacturer's instructions. Kinetics assays for XyrA were performed in a reaction buffer composed of 50 mM sodium phosphate (pH 7.6, 5 mM MgCl2) with NADPH as cofactor (Suzuki, T, et al. Expression of xyrA gene encoding for D-Xylose reductase of Candida tropicalis and production of xylitol in Escherichia coli. J. Biosci. Bioeng. 87, 280-284 (1999)). In these assays, NADPH was held at a constant initial level of 50 μM. Results of the assay were measured through monitoring the absorbance of NADPH at 340 nm for 1.5 hours (15 s per read) using a SpectraMax Plus 384 microplate reader (Molecular Devices). Reaction velocity is plotted as a function of xylose concentration. Using the Eadie-hofstee equation, we got the parameters: Vmax=22.6±1.01 U, kcat=13.56=3.05 s$^{-1}$ and Km: 35.12±3.05 mM.

(XylA) Xylose Isomerase Quantification

Xylose isomerase activities from cell extracts were quantified with a D-xylose reductase coupled enzyme assay, similar to methods previously described, and following a decrease in absorbance of NADPH at 340 nm (Guamán, L. P, et al, xylA and xylB overexpression as a successful strategy for improving xylose utilization and poly-3-hydroxy butyrate production in Burkholderia sacchari, J. Ind. Microbiol. Biotechnol. 45, 165-173 (2018) and Lee, S.-M., Jellison, T. & Alper, H. S. Directed evolution of xylose isomerase for improved xylose catabolism and fermentation in the yeast Saccharomyces cerevisiae. Appl. Environ. Microbiol. 78, 5708-5716 (2012)). Cultures were grown in shake flasks in SM10++ media and harvested in mid exponential phase, washed and resuspended in SM 10 No phosphate media. After 16 hours of phosphate depletion, cells were pelleted by 10 minutes of centrifugation (4122 RCF, 4 degrees C.) and lysed with BugBuster protein extraction reagent (Millipore Sigma. Catalog #70584) according to the manufacturer's protocol. Cell debris was removed by two rounds of centrifugation, 20 minutes (4122 RCF, 4 degrees C.) followed by a 20 minute hard spin (14000 RCF, 4 degrees C.). The lysate was filtered with Amicon 30MWCO filters (Millipore Sigma, Catalog #UFC8030) according to the manufacturer's protocol and washed three times to exchange the buffer with the reaction buffer (45 mM sodium phosphate, 10 mM MgCl$_2$, pH 7.6) and remove metabolites. Samples were assayed in triplicate in a 96 well plate with 100 μL of the filtered cell extract per well containing 31.25 mM xyulose, 0.5 mM NADPH, and 1 ug/mL of purified D-xylose reductase (see above). The absorbance at 340 nm was measured every 15 seconds for 1.5 hours and the slope of the linear region was used to quantify XylA activity. Total protein concentration of each sample was determined with a standard Bradford assay. Kinetic parameters were as follows: kcat: 13.56±3.05 s$^{-1}$, Km: 35 12±3.05 mM.

(UdhA) Soluble Transhydrogenase Quantification

The activity of the soluble transhydrogenase was quantified by method previously reported (Chou, H.-H., Marx, C. J. & Sauer, U. Transhydrogenase promotes the robustness and evolvability of *E. coli* deficient in NADPH production. *PLOS Genet.* 11, e1005007 (2015) and Sauer, U., Canonaco, F., Heri. S., Perrenoud, A. & Fischer, E. The soluble and membrane-bound transhydrogenases UdhA and PntAB have divergent functions in NADPH metabolism of *Escherichia coli. J. Biol. Chem.* 279, 6613-6619 (2004)). The process of UdhA expression and cell lysis was carried out using the same method as the XyrA expression mentioned above. The lysates were centrifuged for 15 minutes (4200 RPM, 4° C.) to remove large debris. A second hard spin was performed for 30 minutes (14000 RPM, 4° C.) to remove remaining debris and further separate the membrane fraction from the soluble transhydrogenase. Lysates were diluted 1:5 with the assay reaction buffer (50 mM Tris-HCl, 2 mM MgCl, pH 7.6) and transferred to an Amicon Ultra centrifugal filter (10 kDa MWCO). The samples were centrifuged for 30 minutes (4200 RPM, 4° C.) and this step was repeated 3 times to remove metabolites and exchange the lysis buffer for the assay buffer. After filtration the protein concentrations of the samples were quantified with a standard Bradford assay.

Then soluble transhydrogenase activity was assayed at room temperature. Assays were performed in black 96 well plates by mixing equal volumes of lysate and reaction buffer for a final volume of 100 μL per well and a final concentration of 0.5 mM NADPH and 1 mM 3-acetylpyridine adenine dinucleotide (APAD$^+$). Changes in absorbance at 400 nm and 310 nm due to the reduction of APAD$^+$ and the oxidation of NADPH, respectively, were monitored simultaneously by Spectramax Plus 384 microplate reader at 30 second intervals for 30 minutes. A standard curve was used to calculate the molar absorptivity of NADPH (3.04*10$^3$ M$^{-1}$ cm$^{-1}$). The molar absorptivity was used to convert the measured slope of the linear region to the change in concentration per minute. The specific activity (Units per mg of total protein) was determined by dividing the change in concentration per minute by the protein concentration.

FabI Quantification

Quantification of FabI via a C-terminal GFP tags was performed using a GFP quantification kit from AbCam (Cambridge, UK, Cat #ab171581) according to manufacturer's instructions.

Xylose and Xylitol Quantification

In micro-fermentations, xylose and xylitol were quantified by commercial bioassays from Megazyme (Wicklow, Ireland, Cat #K-XYLOSE and K-SORB), according to the manufacturer's instructions. An HPLC method coupled with a refractive index detector was used to quantify both xylose as well as xylitol from instrumented fermentations. Briefly, a Rezex ROA-Organic Acid H (8%) Analysis HPLC Column (Cat #: #00H-0138-K0, Phenomenex, Inc., Torrance, CA, 300×7.8 mme) was employed for the separation of xylose and xylitol, 5 mM Sulfuric acid as the isocratic mobile phase at a flow rate of 0.5 mL/min, at 55° C., A Waters Acquity H-Class UPLC integrated with a Waters 2414 Refractive Index (RI) detector (Waters Corp., Milford, MA. USA) was used for detection. The injection volume of samples and standards was 10 μL. Samples were diluted 20 fold in water in order to be in the linear range (0.01 to 20 g/L). MassLynx v4.1 software was used for all the peak integration and analyses.

NADPH Pool Quantification

NADPH pools were measured t using an NADPH Assay Kit (AbCam, Cambridge, UK, Cat #ab186031) according to manufacturer's instructions. Cultures and phosphate depletion were performed as described above for XyrA expression (except there was no xyrA plasmid in the cell). Cells were lysed using the lysis buffer in the assay kit.

Metabolic Modeling

In silico analyses were performed implementing Constraint-based (COBRA) models for *E. coli*, developed employing the COBRApy Python package with a previously reported reconstruction as a starting point. This curated *E. coli* K-12 MG1655 reconstruction includes 2,719 metabolic reactions and 1,192 unique metabolites. This model was adapted as follows. First, missing reactions and metabolites for xylitol production and export were added as shown in Table S5:

TABLE S5

| Xylitol Specific reactions added to the metabolic model | | |
|---|---|---|
| Name | Reaction | Identifier |
| Xylose reductase | h_c + nadph_c + xyl_D_c ⇌ nadp_c + xylt_c | XYLR |
| Xylitol exchange | xylt_e ⇌ | EX_xylt_e |
| Xylitol transport via passive diffusion | xylt_e ⇌ xylt_c | XYLTt |
| Flavodoxin reductase (NADPH) | 2.0 flxso_c + nadph_c ⇌ 2.0flxr_c + h_c + nadp_c | FLDR2 |

All reactions, metabolites stoichiometry and identificators were extracted from the BIGG Models database. The resulting model was validated for mass balances and metabolite compartment formulas with COBRApy validation methods. Once properly balanced, a growth model was created and analyzed. Specific evaluated conditions and biomass fluxes are shown in Table S6.

TABLE S6

| Metabolic model validation with different carbon sources and oxygen levels. (All flux values are expressed in nmol/gDW * hr). | | | | |
|---|---|---|---|---|
| Only Carbon Source | C.S Flux | Oxygen Flux | Biomass Flux obtained from model | Previously reported Biomass Flux* |
| Glucose | −8.8 | −30 (Aerobic) | 0.771914 | 0.70 ± 0.01 |
| Glucose | −8.8 | 0 (Anaerobic) | 0.253285 | 0.33 ± 0.02 |
| Xylose | −9.5 | −30 (Aerobic) | 0.645282 | 0.50 ± 0.02 |
| Xylose | −9.5 | 0 (Anaerobic) | 0.115445 | 0.13 ± 0.02 |

*Numbers from (Prasad, S., Singh, A. & Joshi, H. C. Ethanol as an alternative fuel from agricultural, industrial and urban residues. *Resour. Conserv. Recycl.* 50, 1-39 (2007)).

Next, experimental data obtained from the xylitol micro-fermentations was used to constrain the model. Specific constraints included: i) setting the ratio for pyruvate consumption through Pyruvate Dehydrogenase (PDH) and Pyruvate-flavodoxin Oxidoreductase (vbdk), with 10% and 90% of total flux respectively and ii) setting Ferredoxin/flavodoxin reductase to a reversible reaction and iii) using xylose as a sole carbon source with an input flux of 10 mmol/gCDW*hr under minimal media conditions. Finally a set of specific xylitol production strains were constructed and evaluated in silico using Flux Balance Analysis (FBA) to obtain xylitol yields, analyze cofactor and/or metabolites of interest as well as production and consumption fluxes. Specific cases that were analyzed included reduction or increased activity of: Zwf, FabI, GltA, XylA, PntAB and UdhA as shown in Table S7. For each case/condition the following data was obtained: Xylitol yield, NADPH producing and consuming g reaction fluxes and escher maps of central metabolism for flux distribution visualization. Finally, major changes in fluxes between the most relevant strains were analyzed.

TABLE S7

| Strains modeled | | | |
| --- | --- | --- | --- |
| Individual Valves | | Combinations of Valves | |
| Strain | Valves Silencing | Strain | Valves Silencing |
| WT | — | Z-F | zwf & fabI |
| Z | zwf | Z-G | zwf & gltA |
| F | fabI | Z-X | zwf & xylA |
| G | gltA | Z-pAB | zwf & pntAB |
| X | xylA | Z-F-G | zwf, fabI & gltA |
| pAB | pntAB | Z-G-U | zwf, gltA & udhA |
| U | udhA | Z-F-pAB | zwf, fabI & pntAB |

Example 1: Characterization of XyrA Xylose Reductase

Figures 2A, 2B, 2C:
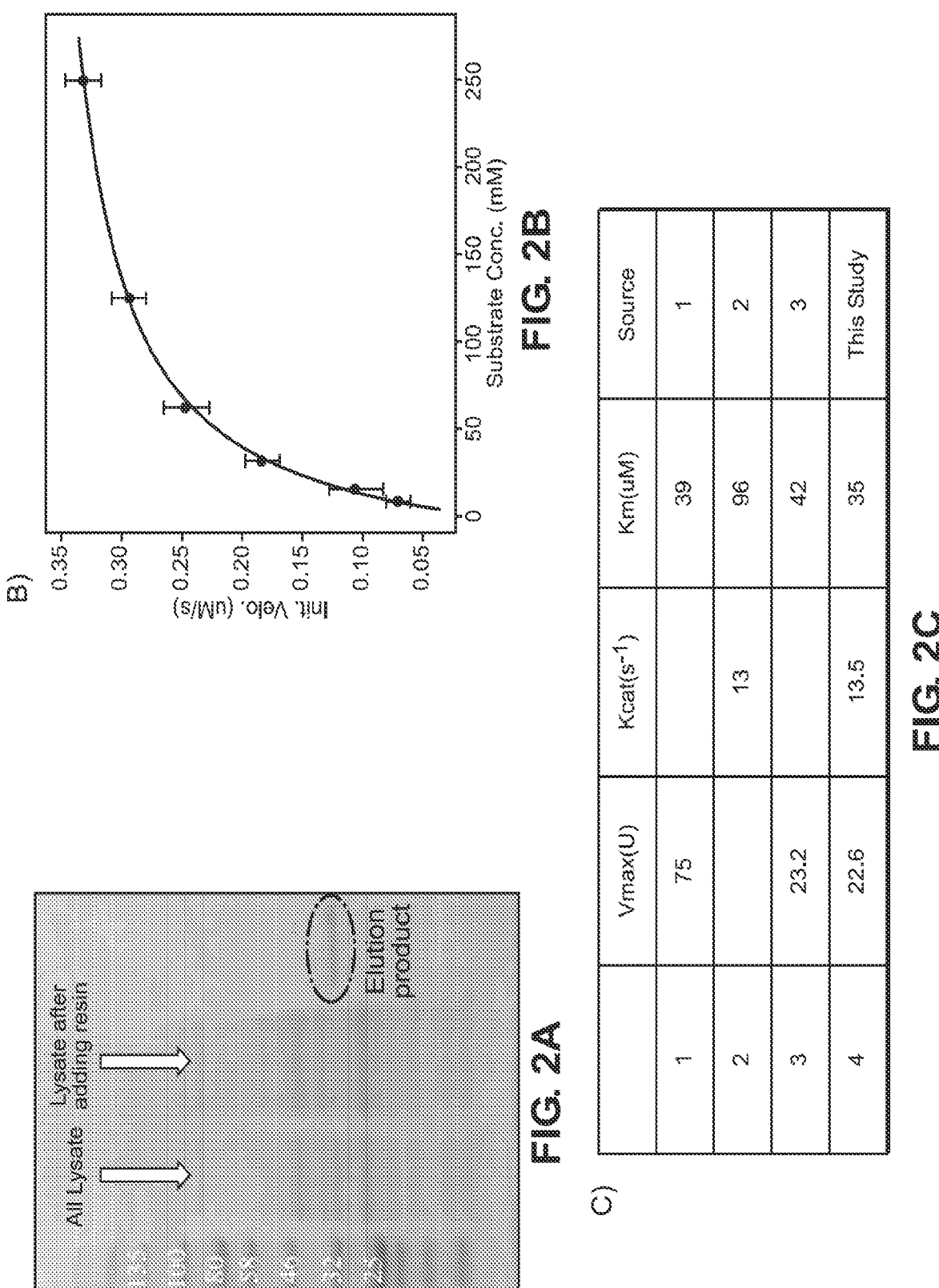
FIG. 2A-C depicts Xylose Reductase Expression and Enzyme Kinetics.

Referring now to FIG. 2(A), Expression of XyrA in BL21 using media combination of SM10++ (for growth) and SM10-No phos (for expression). After the expression, the postproduction cells were lysed by freeze-thawing cycle. Next, the xyrA protein was extracted by N-N Resin because of the His-tag on XyrA which was design into plasmid sequence. In FIG. 2(B), Activity of xyrA with NADPH as co-factor. Reaction velocity is plotted as function of xylose concentration. In these assays, NADPH was held at a constant initial level of 50 uM. FIG. 2(C) Kinetic Parameters for XyrA from this project and from other research sources as comparison. Kinetics for XyrA were measured using 50 mM sodium phosphate, pH 7.6 (containing 5 mM MgCl$_2$).[26] 50 uM NADPH. Results of the assay were measured through monitoring the absorbance of NADPH at 340 nm. Using Eadie-Hofstee equation, the parameters Vmax=22.6 U, kcat=13.5 s$^{-1}$ and km=35.12 mM were established thus confirming protein enzyme activity that could be used in the tank fermentation process. Knowing the Vmax, the minimal expression level needed to hit a desired specific production rate can then be established.

Example 2: Design of Metabolic Valves for Bioproduction of Xylitol

Figure 1:
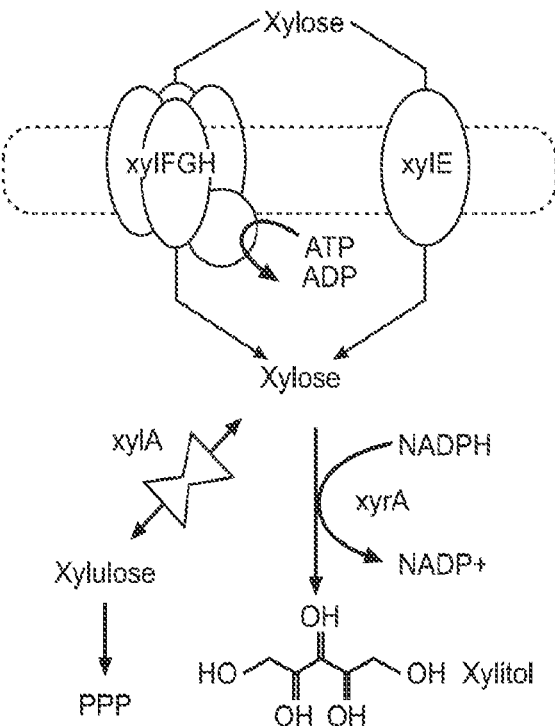
FIG. 1 depicts the design of metabolic valves for the bioproduction of xylitol. The biosynthesis process of xylitol in *E. coli* by xylose reductase (XyrA) with NADPH as cofactor (bold arrow). The main competitive pathway for the consumption of xylose is to xylose by xylose isomerase (XylA, valve).

Rationally designed strains to optimize xylitol production from xylose utilizing two stage dynamic metabolic control, in a phosphate depleted stationary phase were developed. As illustrated in FIG. 1, this design included overexpression of xylose reductase and the dynamic reduction in xylose isomerase (xylA) activity to reduce xylose metabolism which competes with xylitol production. Toward this goal we constructed strains and plasmids to enable the dynamic induction of xyrA, and dynamic reduction in XylA activity upon phosphate depletion, either through gene silencing, proteolysis of XylA or the combination. Refer to Tables 1 and 2 for plasmids and strains used. These strains were evaluated in 96 well plate micro-fermentations as reported by Moreb et al and results are given in FIG. 3.

Example 3: Xylitol Production Utilizing 2-Stage Dynamic Control

Figure 3:
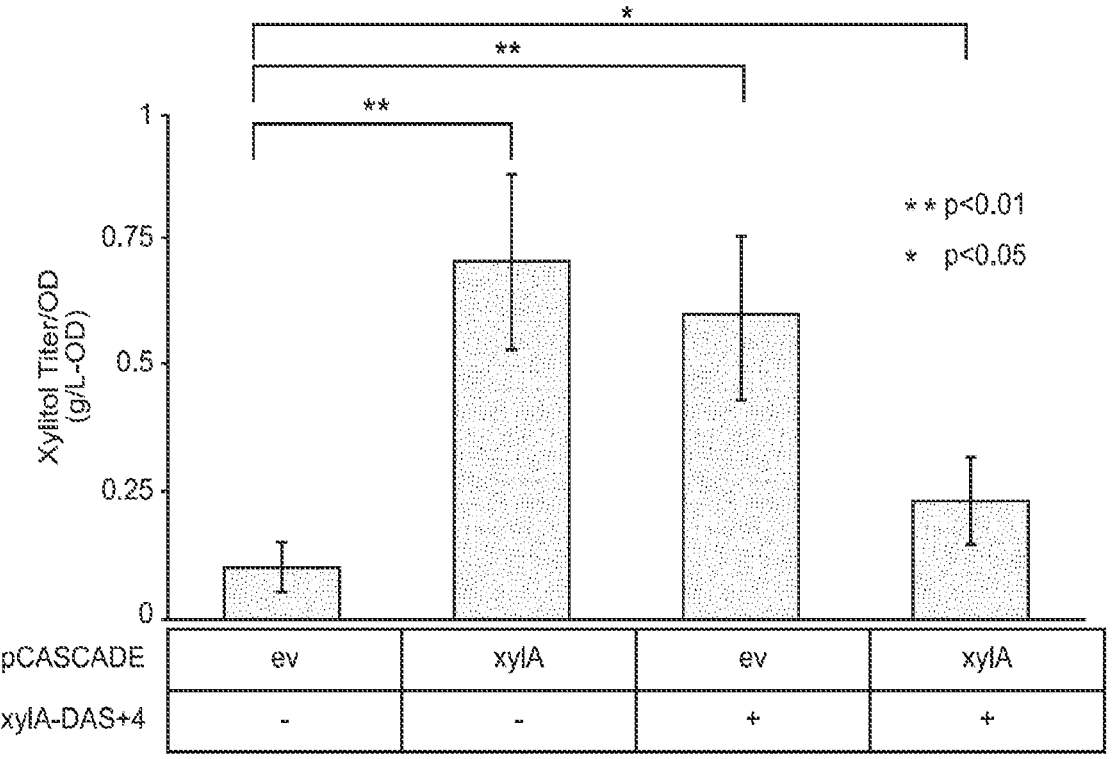
FIG. 3 depicts the xylitol titer/OD (g/L-OD) were measured under different xylA silencing and xylA proteolysis combinations. The specific productivity of different strains was significantly different with the control strain DLF-0025-EV. While all three valve combinations made statistically significant amount more than the DLF25-EV control, xylA silencing or proteolysis alone were better than the combination.

Since dynamic control over XylA ("X") activity only led to modest improvements in xylitol production, FIG. 3, we evaluated the potential impact of a larger set of valves on xylitol production. We constructed a set of strains with valves in key metabolic pathways, FIG. 4. These valves included: citrate synthase (GltA-"G"), glucose-6-phosphate dehydrogenase (Zwf-"Z"), enoyl-ACP reductase (FabI-"F") and soluble transhydrogenase (udhA-"U") which control flux through the tricarboxylic acid cycle, pentose phosphate pathway, fatty acid biosynthesis and NADPH supply respectively. Strains were constructed with combinations of X, U, G, Z and F valves and evaluated for xylitol production. As described above, dynamic metabolic control was accomplished by adding C-terminal DAS+4 degron tags to the xylA, udhA, zwf, gltA and fabI genes as well as the overexpression of guide RNAs enabling silencing of their transcription. Refer to the Methods section for detailed chromosomal modification and plasmid construction.

The panel consisted of ~370 valve combinations of X, U, G, Z and F that were evaluated for xylitol production in two stage 96 well plate micro-fermentations in at least triplicate. Results of these experiments are given in FIGS. 5A and 5B. Xylitol titers ranged from ~0 g/L-OD (600 nm) to ~9.35 g/L-OD (600 nm). Approximately ~80% of the silencing and proteolysis combinations performed better than the control strain, which only produced 0.106 g/L-OD. Significant differences in specific xylitol production (xylitol (g/L) per unit OD600 nm) between valve strains and the control strain were determined by one-way ANOVA (F(414.851)=7.598, p<0.0001).

Figure 4:
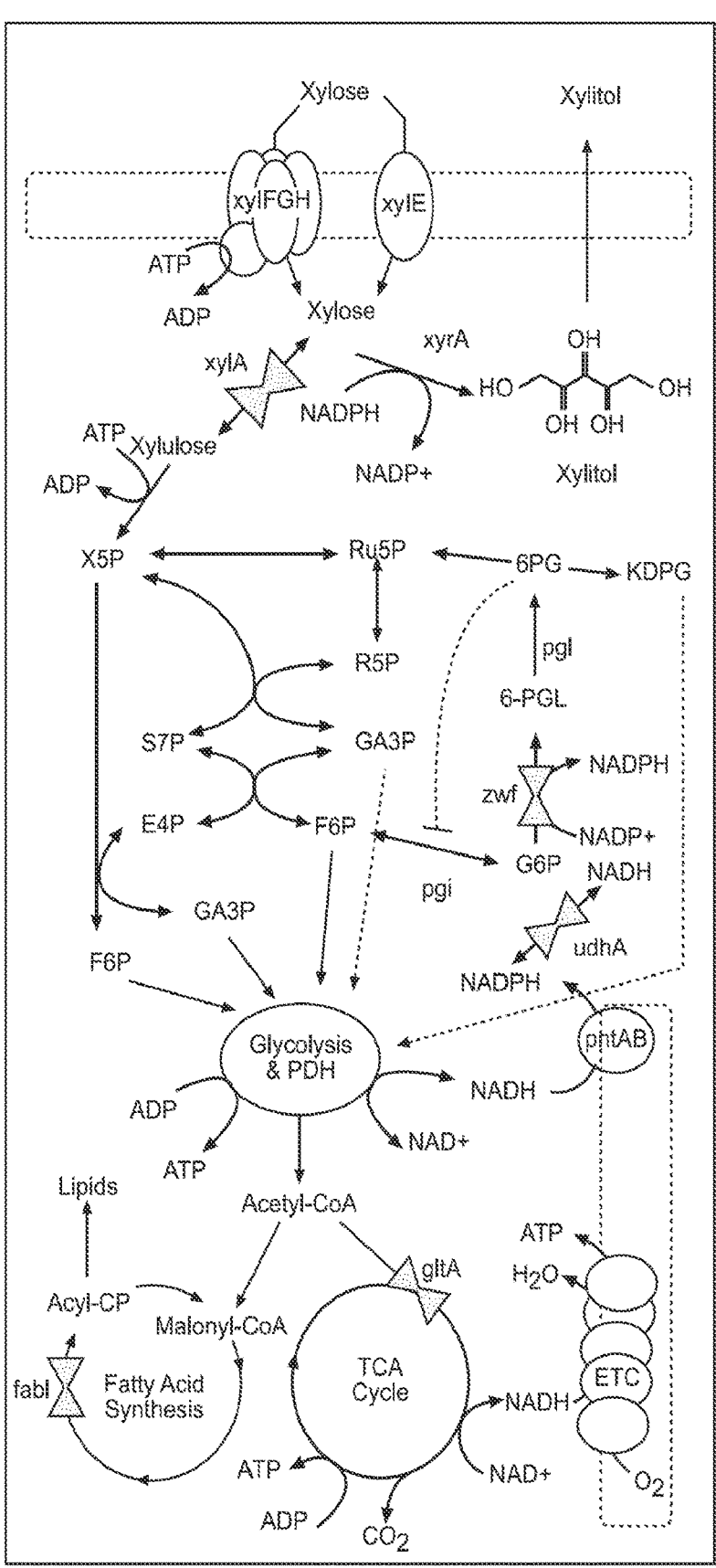
FIG. 4 depicts xylitol Production in *E. coli* utilizing 2-stage Dynamic Control. Strain metabolic network design. The main metabolic pathways include: Fatty Acid Biosynthesis, the Citric Acid Cycle (TCA), NADPH supply, the Pentose Phosphate Pathway Transhydrogenase and Glycolysis. The valves which may be 'switched off' in the metabolic system include xylose isomerase (xylA-X), the soluble transhydrogenase (udhA-U) enoyl-ACP reductase (fabI-F), citrate synthase (gltA-G) and glucose-6-phosphate dehydrogenase (zwf-Z). These valves are all highlighted by red valves. Xylose reductase (xyrA) may be dynamically 'switched on' for xylitol production with NADPH as cofactor.

P-values were used to generate a p-value heatmap (FIG. 6), where only combinations with a p value less than 0.05 are highlighted. Combinations not assayed or with less than 2 successful replicates (lack of success is due to lack of cell growth) are indicated by a gray dot since they are not qualified for statistical analysis. While the incorporation of X valves generally led to increase xylitol production, to surprisingly the two highest xylitol producers had neither X or U valves (which should increase NADPH levels) but rather combinations of F, G and Z valves. The highest producer had a combination of F and Z valves, which the xylitol specific productivity could reach 9.35 g/L-OD600 nm. The performance of this genetic combination was also synergistic above either F or Z valves alone. This was surprising since these two enzymes have no direct or predictable impact of xylitol biosynthesis as can be seen in FIG. 4.

Example 4: Xylitol Production in Instrumented Bioreactors

Based on the results from the micro-fermentations (FIGS. 5 and 6), we chose the "Z-FZ" valve strain (silencing of zwf "Z" and proteolysis of fabI and zwf "FZ") which has titer of 9.35 g/L-OD600 as well as the control for evaluation in instrumented bioreactors. Fermentations were performed according to Menacho-Melgar et al, where phosphate is limiting in the media leading to phosphate depletion and xylitol production in stationary phase as illustrated above in FIG. 5. Results of these fermentations are given in FIG. 6 below. The Z-FZ strain (FIG. 6A) enabled xylitol production up to 104+/−11.31 g/L with 160 hours, while xyrA expression in our control strain DLF_0025-EV (FIG. 6B) led to only ~3 g/L of xylitol within the same time.

Example 5: Improvement of NADPH Flux and Xylitol Biosynthesis

Most previous studies producing xylitol from xylose rely on a bioconversion requiring an additional sugar (usually glucose) as an electron donor (Albuquerque. T. L. de, da Silva, I. J., de Macedo, G. R. & Rocha, M. V. P. Biotechnological production of xylitol from lignocellulosic wastes: A review. *Process Biochem.* 49, 1779-1789 (2014); Cirino, P. C., Chin. J W. & Ingram, L. O. Engineering *Escherichia coli* for xylitol production from glucose-xylose mixtures. *Biotechnol. Bioeng.* 95, 1167-1176 (2006); and Su, B., Wu, M., Zhang. Z., Lin. J. & Yang, L. Efficient production of xylitol from hemicellulosic hydrolysate using engineered *Escherichia coli. Metab. Eng.* 31, 112-122 (2015)). Oxidation of glucose (producing the byproduct gluconic acid) generates NADPH which is then used for xylose reduction (Jin, L.-Q., Xu. W., Yang, B., Liu, Z.-Q. & Zheng. Y.-G. Efficient Biosynthesis of Xylitol from Xylose by Coexpression of Xylose Reductase and Glucose Dehydrogenase in *Escherichia coli. Appl. Biochem. Biotechnol.* 187, 1143-1157 (2019). While these processes offer high xylitol titers and a good yield when considering xylose, the requirement for glucose at equimolar levels to xylose is a significant inefficiency. More broadly, improving NADPH availability or flux, useful in the synthesis of numerous metabolites as well as cell based bioconversions, has been a long standing challenge in metabolic engineering.

We applied two-stage dynamic metabolic control (DMC) to improve NADPH flux and xylitol production using xylose as a sole feedstock (Burg, J. M., Cooper, C. B, Ye, Z., Reed, B. R. & Moreb. E. A. Large-scale bioprocess competitiveness: the potential of dynamic metabolic control in two-stage fermentations. *Current opinion in* (2016)). Dynamic control over metabolism has become a popular approach in metabolic engineering, and has been used for the production of various products from 3-hydroxypropionic acid to myoinositol and many others. We have recently reported an extension of dynamic metabolic control to two-stage bioprocesses, where products are made in a metabolically productive phosphate depleted stationary phase. The implementation of this approach relies on combined use of controlled proteolysis and gene silencing, using degron tags and CRISPR interference respectively. Importantly, in these initial studies we demonstrated that improved metabolic fluxes resulting from dynamic metabolic control, can be a consequence of reducing levels of central metabolites which are feedback regulators of other key metabolic pathways. Specifically, we have recently shown that decreasing glucose-6-phosphate dehydrogenase levels activates the SoxRS regulon increasing expression and activity of pyruvate ferredoxin/flavodoxin oxidoreductase (Pfo). Pfo leads to improved acetyl-CoA production in stationary phase. (Refer to FIG. 11(A)). In this work we report the evaluation of combinations of synthetic metabolic valves on xylitol production from xylose. Firstly, increased Pfo activity not only leads to improved acetyl-CoA flux but also NADPH production. NADPH is produced from reduced flavodoxin/ferredoxin via the action of NADPH dependent flavodoxin/ferredoxin reductase (Fpr). We also identify a key regulatory mechanism controlling NADPH fluxes, namely the inhibition of the membrane bound transhydrogenase (PntAB) by fatty acid metabolites. By dynamically disrupting fatty acid biosynthesis, we alleviate inhibition of PntAB. This mechanism is synergistic with activating Pfo and greatly increases NADPH flux and xylitol production. We compare this "regulatory." approach with a more intuitive stoichiometric strategy where the levels of key enzymes competing with xylitol production are dynamically reduced. Importantly, improved NADPH fluxes are, in part, a consequence of reduced NADPH pools. Reduced NADPH pools drive changes in expression and activity that result in increased NADPH fluxes, presumably a regulatory mechanism which has evolved to restore set point NADPH levels. These results are a reminder that pools and flux are not equivalent and not necessarily correlated.

Stoichiometric Strategy

We initially rationally designed strains to optimize xylitol production from xylose utilizing two stage dynamic metabolic control, reliant on decreasing levels of key competitive pathways. As illustrated in FIG. 1, this design included dynamic reduction in xylose isomerase (xylA) and soluble transhydrogenase (udhA) activities. These modifications were designed to reduce xylose metabolism which competes with xylitol production and increases NADPH supply NADPH can be consumed by the soluble transhydrogenase. Toward this goal we constructed strains and plasmids to enable the dynamic reduction in XylA and UdhA levels upon phosphate depletion. Refer to Supplemental Table S1 for strains and plasmids used in this study. As described above and previously reported dynamic reduction in activity was accomplished by adding C-terminal DAS+4 degron tags to the chromosomal xylA and udhA genes as well as the overexpression of guide RNAs aimed at silencing their expression. The impact of these modifications on enzyme levels in two stage cultures is given in FIG. 9A-B. In the case of XylA, proteolysis led to ~60% reduction in activity. To our surprise the silencing gRNA actually led to an increased XylA activity level. The mechanism behind this is currently unknown and requires further study. The combination of silencing and proteolysis resulted in no further reduction in activity when compared to proteolysis alone. In the case of UdhA, proteolysis resulted in a ~30% reduction in activity, whereas silencing had no detectable impact on activity levels with or without proteolysis.

The combination of proteolysis and silencing for XylA or "X valves" and proteolysis alone in the case of UdhA, a "U Valve", are evaluated for xylitol production. Specifically strains were engineered with these metabolic valves as well as for overexpression of a xylose reductase (xyrA from *A. niger*) and evaluated in two-stage minimal media microfermentations as reported by Moreb et al. Results are given in FIG. 10A-C. Additionally, a confirmatory analysis of XyrA kinetics was performed, and results are given in Supplemental FIG. 11. The combination of modifications resulted in a 16 fold increase in xylitol production compared to the control.

Regulatory Strategy

To investigate the impact of a regulatory strategy, we next sought to evaluate the potential impact of a larger set of valves on xylitol production as illustrated in FIG. 12A. We constructed a set of strains with valves in citrate synthase (GltA), glucose-6-phosphate dehydrogenase (Zwf) and enoyl-ACP reductase (FabI) which control flux through the tricarboxylic acid cycle, pentose phosphate pathway and fatty acid biosynthesis, respectively. We have previously reported the construction of metabolic valves in GltA ("G Valves"), and Zwf ("Z Valves") which comprised either proteolytic degradation (DAS+4 tags), gene silencing (either the zwf promoter or gltAp2 promoter) or both. In the case of FabI, we constructed new strains and plasmids to evaluate two-stage dynamic control on FabI levels. Toward this goal, as similarly reported by Li et al., we appended a superfolder GFP to the C-terminus of the fabI allele to enable quantification of protein levels by an ELISA. Unfortunately and unexpectedly, when plasmids silencing fabI expression were evaluated, guide RNA protospacer loss was observed (FIG. 13A-D) and as a result we could not reliably obtain results where fabI is silenced. FabI proteolysis led to a ~75% reduction in FabI levels (FIG. 14), and as a result proteolytic degradation alone will be referred to as an "F Valve". Strains were constructed with combinations of "X", "U", "G", "Z" and "F" valves and evaluated for xylitol production, again in minimal media microfermentations. Results are given in FIG. 12A-D. To our surprise the highest xylitol producer had neither "X" or "U" valves but rather a combination of "F" and "Z" valves. Xylitol production in the "FZ" valve strain was synergistic above either "F" or "Z" valves alone (FIG. 12B). This was surprising in that these two enzymes have no direct or predictable impact of xylitol biosynthesis as can be seen in FIG. 12A. We have recently reported that the "Z" valve results in increased acetyl-CoA fluxes by leading to the activation of Pfo (encoded by the ydbK gene). With increased flux through Pfo we hypothesized that NADPH could be generated from reduced ferredoxin/flavodoxin through ferredoxin reductase (Fpr). Using deletions in ydbK and fpr, as shown in FIG. 15, we confirmed that this pathway, and specifically Fpr is indeed in part responsible for the elevated xylitol production and NADPH flux observed in our "FZ" valve strain. This is, to our knowledge, the first confirmation that Fpr is reversible in vivo. This reverse flux through Fpr may be dependent on low NADPH pools (as discussed below). The synergistic impact of the "F" valves was somewhat unanticipated. However, elevated NADPH fluxes due to dynamic control over FabI (enoyl-ACP reductase) can be attributed to reduced levels of fatty acid metabolites, specifically acyl-CoAs (and potentially their precursors acyl-ACPs). Fatty acyl-CoAs are competitive inhibitors of the membrane bound transhydrogenase encoded by the pntAB genes (FIG. 12A). Palmitoyl-CoA, specifically, has a reported Ki of 1-5 µM. Control over FabI levels and/or activity has been previously shown to reduce acyl-ACP pools and as a result alleviate feedback inhibition of acetyl-CoA carboxylase and malonyl-CoA synthesis. To our knowledge this is the first study demonstrating the importance of these metabolites in controlling NADPH fluxes. While previous reports demonstrate the inhibition of PntAB by acyl-CoAs (which in minimal media are derived from fatty acid biosynthesis there remains a possibility that acyl-ACPs also act as inhibitors, although future work is needed to confirm this hypothesis.

Figures 15A, 15B, 15C, 15D:
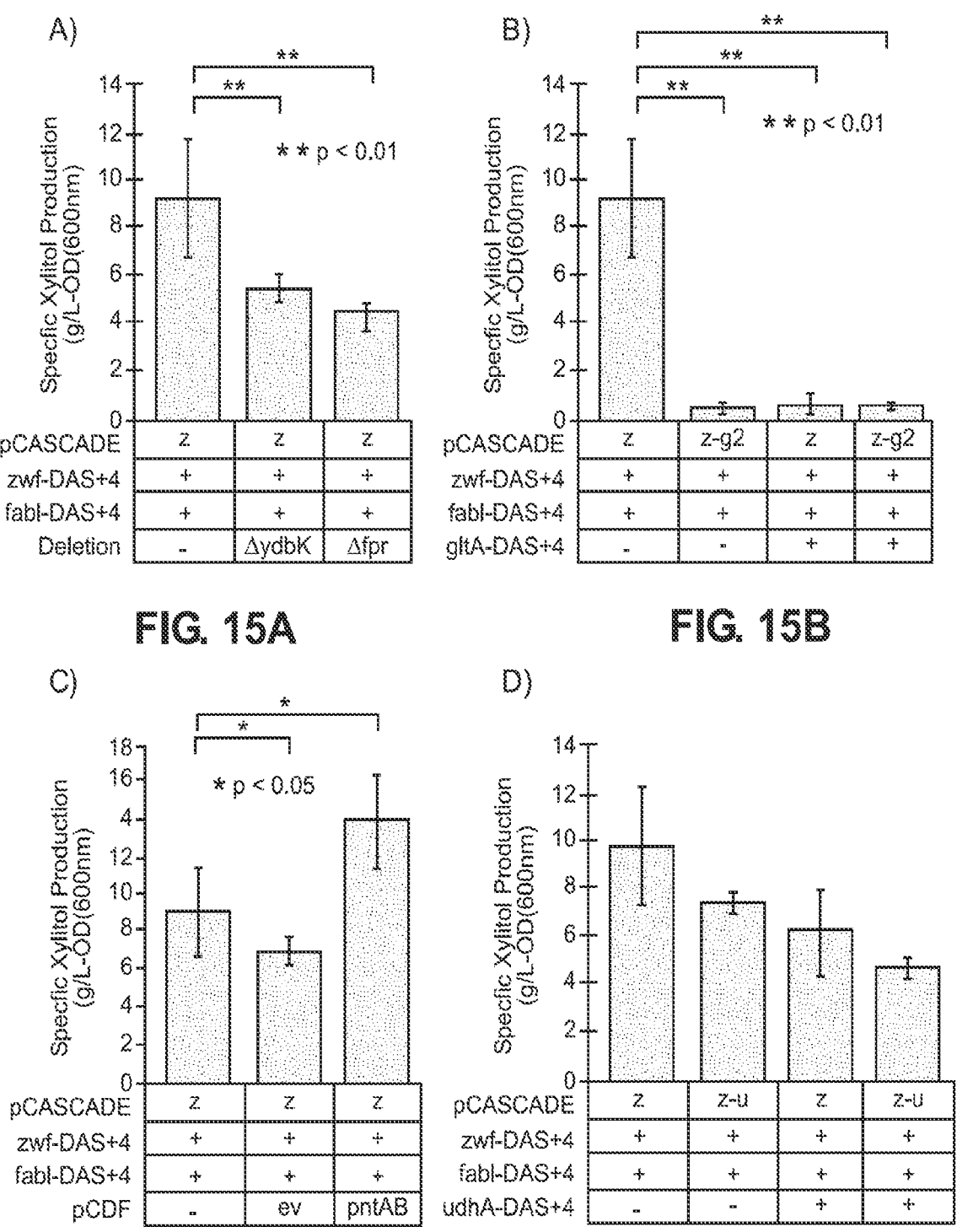

We next evaluated several additional modifications on top of the "FZ" valves, with a potential to impact xylitol production. (FIG. 15B-D). Specifically we evaluated the addition of "G" and "U" valves as well as overexpression of pntAB. Plasmid based overexpression of the pntAB genes (using a low phosphate inducible promoter led to a significant improvement in xylitol production (FIG. 15B). In contrast, the addition of either the "G" or "U" valve to the "FZ" combination did not increase xylitol synthesis but rather led to a significant decrease in xylitol production (FIG. 15C-D). This suggests that citrate synthase (GILA) activity, and flux through the TCA cycle, is required for optimal NADPH flux.

Using results from these experiments, we were able to estimate boundary conditions for several intracellular fluxes. For example from FIG. 15B, we can estimate that flux through the Pfo/Fpr pathway accounts for at most ~55% of the NADPH/xylitol production. As a result we are able to build stoichiometric metabolic models, as illustrated in FIG. 16A-B, comparing an optimal growth phase and xylitol production phase. Importantly, this model confirms that indeed TCA flux is critical for xylitol production FIG. 17A-B) and that a 4-fold increase in PntAB activity, in addition to flux through the Pfo/Fpr pathways is needed to explain increases in NADPH flux and xylitol production. The model predicts an overall maximal xylitol yield in this metabolic state of ~0.864 g/g of xylose, in line with yields measured in fed batch fermentations as discussed below.

Production in Instrumented Bioreactors

Next, we compared xylitol production in instrumented bioreactors using the "FZ" valve strain with and without pntAB overexpression with a control strain. Minimal media fed batch fermentations were performed as described by Menacho-Melgar et al., wherein the media has enough batch phosphate to support target biomass levels (~25 gCDW/L) prior to phosphate depletion and induction of xylitol biosynthesis in stationary phase. Results of these studies are given in FIG. 18. While xyrA expression in our control strain (DLF_Z0025) led to only a few grams per liter of xylitol (FIG. 18A), the incorporation of "FZ" valves led to titers over 100 g/L in 160 hours of production (FIG. 18B). The additional overexpression of pntAB (FIG. 18C) resulted in maximal titers over 200 g/L (185-204 g/L) in 170 hrs. In these duplicate fermentations the average overall xylitol yield was 0.873+/−0.026 g/g xylose, and the average production yield (in stationary phase) was 0.935+/−0.011 g/g xylose.

Improved NADPH Flux is not Correlated with NADPH Pools.

Lastly, we measured the levels of NADPH in a set of our engineered strains. Results are given in FIG. 19A. Interestingly, there was no correlation between specific xylitol production and NADPH pools. In this case, the three strains having the highest NADPH pools were the control strain and the strains with dynamic control over enoyl-ACP levels ("F" valve) or soluble transhydrogenase ("U" valve) levels. The addition of the "Z" valve (reduced levels of glucose-6-phosphate dehydrogenase) led to a decrease in NADPH pools but an increase in NADPH flux. Deletions of either ydbK and or fpr, also led to decreases in NADPH levels, and while overexpression of pntAB increased xylitol production rates and fluxes it did not improve NADPH pools in the "FZ" background.

The use of 2-stage dynamic control generated an usual metabolic state leading to enhanced NADPH fluxes and xylitol production. To our knowledge this is the highest titer and yield of xylitol produced to date in engineered E. coli, particularly with xylose as a sole carbon source. Additionally, the productive stationary phase generated with these modifications can be extended to at least 170 hours. While the focus of this work has been on xylitol production, the identification of "F" and "Z" valves impacting NADPH flux has applicability to other NADPH dependent processes including more complicated pathways, and may represent a facile method for routine NADPH dependent bioconversions. The impact of FabI activity and fatty acid metabolite pools, on transhydrogenase activity, is consistent with previous biochemical studies, and has likely evolved to balance NADPH supply with fatty acid synthesis demand Unfortunately, this feedback regulatory mechanism has been lost in the past several decades of metabolic engineering studies in *E. coli*, yet represents a powerful approach to improving NADPH fluxes. The unpredictable combination of "F" and "Z" valves is at odds with standard thinking regarding NADPH flux, where Zwf is often considered one of the primary sources of NADPH in the cell and reducing Zwf activity would not be high on a list of changes to make in order to increase NADPH supply.

In order to explain the lack of correlation between NADPH pools and our results, we developed a conceptual model as illustrated in FIG. 1. The "Z" valve leads to a decrease in NADPH pools which activate the SoxRS regulon, which is sensitive to oxidant and NADPH levels. SoxRS activation leads to increased expression of Pfo, which is required to maintain a high rate of pyruvate oxidation, generating NADPH via Fpr. Uniquely, this study identifies a previously unreported pathway for NADPH production utilizing Pfo and Fpr and supports that Fpr catalyzes a reversible reaction in vivo. Pfo expression is required, not only for pyruvate oxidation and sugar consumption but also NADH generation via the TCA cycle. Increased TCA flux produces excess NADH which is needed as a substrate for PntAB for maximal NADPH flux. Disruption of the TCA cycle ("G" Valve, FIG. 15B) eliminates NADH production and acetyl-CoA consumption, greatly reducing NADPH flux. Increased NADPH levels due to the "F" valve make sense in light of the results discussed and are attributable to increased activity of the membrane bound transhydrogenase. PntAB. Reduced soluble transhydrogenase (UdhA, FIG. 15D) levels leads to increased NADPH pools (FIG. 19) which presumably reduce SoxRS activation and Pfo expression. Simply put, the metabolic network responds to decreased NADPH and acyl-CoA pools by increasing sugar consumption and NADPH flux to compensate. If "set" point NADPH pools are regained or if continued sugar catabolism tops, continued NADPH flux is halted.

Lastly, the metabolic state leading to enhanced NADPH flux and xylitol production would be hard to identify and/or engineer in a growth coupled process as it relies on the manipulation of feedback inhibition due to central metabolites. These central metabolic regulatory circuits have evolved to balance fluxes to both optimize growth and enable adaptive responses to environmental and physiological perturbations. Dynamic metabolic control, and in particular two-stage dynamic metabolic control, is uniquely suited to manipulate central metabolite levels without impacting cell growth or survival. This approach can lead to the discovery as well as the manipulation of central regulatory mechanisms, which in turn have a high potential to enhance metabolic fluxes and drive future metabolic engineering strategies.

The invention claimed is:

1. A genetically modified *E. coli* microorganism for producing xylitol from xylose comprising:
- a first gene expression-silencing synthetic metabolic valve or an enzymatic degradation synthetic metabolic valve for overexpression of xylose reductase in a productive stationary phase;
- a second gene modification comprising chromosomal modification of the xylA gene to provide for reducing the amount of xylose isomerase enzyme in a productive stationary phase; and
- further comprising a gene-silencing synthetic metabolic valve or the enzyme degradation synthetic metabolic valve are directed to control of the gene encoding enoyl-ACP reductase, or the enoyl-ACP reductase enzyme in a productive stationary phase, wherein the genetically modified *E. coli* microorganism will produce xylitol in a biofermentation process comprising growing the genetically modified *E. coli* microorganism in a medium in a growth phase, transitioning to a productive stationary phase, the transition comprising: slowing or stopping microorganism growth, inducing the first gene modification, to effect overexpression of xylose reductase and the second gene expression-silencing synthetic metabolic valve or an enzymatic degradation synthetic metabolic valve to decrease the total amount of xylose isomerase enzyme activity, and producing xylitol in the productive stationary phase, wherein the biofermentation process occurs in a media in which xylose was substituted for glucose, 1 gram xylose for 1 gram glucose.

2. The genetically modified *E. coli* microorganism of claim 1, wherein the xylose reductase is an NADPH dependent xylose reductase.

3. The genetically modified *E. coli* microorganism of claim 1, wherein the xylose reductase is the xyrA gene of *A. niger*.

4. The genetically modified *E. coli* microorganism of claim 1, wherein the genetically modified microorganism produces xylitol from a xylose feedstock.

5. The genetically modified *E. coli* microorganism of claim 1, further comprising a gene-silencing synthetic metabolic valve or the enzyme degradation synthetic metabolic valve are directed to control of the gene encoding glucose-6-phosphate dehydrogenase (zwf) or the glucose-6-phosphate dehydrogenase (zwf) enzyme.

6. The genetically modified *E. coli* microorganism of claim 1, further comprising a gene-silencing synthetic metabolic valve or the enzyme degradation synthetic metabolic valve consist of:

silencing of a gene encoding glucose-6-phosphate dehydrogenase (zwf); and enzyme degradation of glucose-6-phosphate dehydrogenase (zwf) and enoyl-ACP reductase (fabI) enzymes.

7. The genetically modified *E. coli* microorganism of claim 1, wherein the first or second synthetic metabolic valves are induced by nutrient depletion.

8. The genetically modified *E. coli* microorganism of claim 1, wherein the first or second synthetic metabolic valves are induced by phosphate depletion.

9. The genetically modified *E. coli* microorganism of claim 1, the microorganism further comprises a chromosomal deletion.

10. The genetically modified *E. coli* microorganism of claim 1, wherein the first or second synthetic metabolic valves effect gene silencing by CRISPR interference, the and the first, second or third synthetic metabolic valves further comprising a CASCADE guide array, the array comprising two or more genes encoding small guide RNAs each specific for targeting a different gene for simultaneous silencing of multiple genes.

11. The genetically modified *E. coli* microorganism of claim 1, wherein the microorganism produces a xylitol product titer of at least 20 g/L at twenty-four hours in a biofermentation process.

12. The genetically modified *E. coli* microorganism of claim 1, further comprises modification to the *E. coli* microorganism so that:

activity of a membrane bound transhydrogenase activity is induced;

activity of a pyruvate ferredoxin oxidoreductase is induced; and activity of a NADPH dependent ferredoxin reductase is induced.

13. A multi-stage fermentation bioprocess for producing xylitol from a genetically modified *E. coli* microorganism of claim 1, comprising:

(a) providing the genetically modified *E. coli* microorganism;

(b) growing the genetically modified *E. coli* microorganism in a media with a xylose feedstock;

(c) transitioning from a growth phase to a xylitol producing stage by slowing or stopping the growth of the *E. coli* microorganism; and inducing the first or second synthetic metabolic valves to effect overexpression of xylose reductase and reducing expression of xylose isomerase, thereby (d) producing xylitol.

14. A genetically modified *E. coli* microorganism for producing xylitol from xylose comprising:

a first gene expression-silencing synthetic metabolic valve or an enzymatic degradation synthetic metabolic valve for overexpression of xylose reductase in a productive stationary phase;

a second gene modification comprising chromosomal modification of the xylA gene to provide for reducing the amount of xylose isomerase enzyme in a productive stationary phase and wherein the genetically modified *E. coli* microorganism will produce xylitol in a biofermentation process comprising growing the genetically modified *E. coli* microorganism in a medium in a growth phase, transitioning to a productive stationary phase, the transition comprising: slowing or stopping microorganism growth, inducing the first gene modification, to effect overexpression of xylose reductase and the second gene expression silencing synthetic metabolic valve or an enzymatic degradation synthetic metabolic valve to decrease the total amount of xylose isomerase enzyme activity, and producing xylitol in the productive stationary phase, wherein the biofermentation process occurs in a media in which xylose was substituted for glucose, 1 gram xylose for 1 gram glucose.

15. The genetically modified *E. coli* microorganism of claim 14, wherein the xylose reductase is an NADPH dependent xylose reductase or the xyrA gene of *A. niger*.

16. The genetically modified *E. coli* microorganism of claim 14, wherein the *E. coli* microorganism further comprises a gene expression-silencing synthetic metabolic valve or an enzymatic degradation synthetic metabolic valve to regulate expression of a third gene or third enzyme that is glucose-6-phosphate dehydrogenase (zwf), enoyl-ACP reductase (fabI), soluble transhydrogenase (udhA) or citrate synthase (gltA).

17. The genetically modified *E. coli* microorganism of claim 14, wherein the induction occurs via nutrient depletion or phosphate depletion.

18. The genetically modified *E. coli* microorganism of claim 14, further comprising a chromosomal deletion.

19. The genetically modified *E. coli* microorganism of claim 14, wherein the silencing of gene expression comprises CRISPR interference, and the genetically modified microorganism further comprises a CASCADE guide array, the array comprising two or more genes encoding small guide RNAs each specific for targeting a different gene for simultaneous silencing of multiple genes.

20. The genetically modified *E. coli* microorganism of claim 14, wherein the microorganism produces a xylitol product titer of at least 20 g/L at twenty-four hours in a biofermentation process.

21. The genetically modified *E. coli* microorganism of claim 14, further comprising:

activity of a membrane bound transhydrogenase activity is induced;

activity of a pyruvate ferredoxin oxidoreductase is induced;

activity of a NADPH dependent ferredoxin reductase is induced and wherein the microorganism produces at least one chemical product whose biosynthesis requires NADPH.

22. A multi-stage fermentation bioprocess for producing xylitol from a genetically modified *E. coli* microorganism of claim 14, comprising:

(a) providing the genetically modified *E. coli* microorganism, (b) growing the genetically modified *E. coli* microorganism in a media with a xylose feedstock;

(c) transitioning from a growth phase to a xylitol producing stage by slowing or stopping the growth of the *E. coli* microorganism; and inducing the first or second synthetic metabolic valves to effect overexpression of xylose reductase or reducing expression of xylose isomerase, thereby (d) producing xylitol.

* * * * *